US012796942B2

(12) United States Patent
Valdez

(10) Patent No.: US 12,796,942 B2
(45) Date of Patent: Nov. 17, 2026

(54) IMPLANT DEVICES WITH SHUNT CHANNEL SENSORS

(71) Applicant: EDWARDS LIFESCIENCES CORPORATION, Irvine, CA (US)

(72) Inventor: Michael G. Valdez, Riverside, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 476 days.

(21) Appl. No.: 18/450,780

(22) Filed: Aug. 16, 2023

(65) Prior Publication Data

US 2023/0389811 A1 Dec. 7, 2023

Related U.S. Application Data

(63) Continuation of application No. PCT/US2022/014858, filed on Feb. 2, 2022.

(60) Provisional application No. 63/150,031, filed on Feb. 16, 2021.

(51) Int. Cl.
*A61B 5/0215* (2006.01)
*A61B 5/00* (2006.01)

(52) U.S. Cl.
CPC .......... *A61B 5/0215* (2013.01); *A61B 5/0031* (2013.01); *A61B 5/6862* (2013.01); *A61B 5/6869* (2013.01); *A61B 5/6882* (2013.01)

(58) Field of Classification Search
CPC ............. A61B 2017/1139; A61B 2017/00252; A61B 2017/00247; A61B 2017/3484; A61B 2017/3488; A61B 5/6862; A61B 5/6869; A61B 5/6882
See application file for complete search history.

(56) References Cited

U.S. PATENT DOCUMENTS

| | | | |
|---|---|---|---|
| 3,538,917 | A | 11/1970 | Selker |
| 3,675,656 | A | 7/1972 | Hakim |
| 3,730,186 | A | 5/1973 | Edmunds, Jr. et al. |
| 3,853,126 | A | 12/1974 | Schulte |
| 3,882,862 | A | 5/1975 | Berend |
| 3,882,882 | A | 5/1975 | Preisig |
| 3,903,894 | A | 9/1975 | Rosen et al. |

(Continued)

FOREIGN PATENT DOCUMENTS

| | | | | |
|---|---|---|---|---|
| WO | WO-2020123338 A1 * | 6/2020 | ........... | A61B 5/6862 |
| WO | 2020215090 A1 | 10/2020 | | |

(Continued)

OTHER PUBLICATIONS

Emil Mantini, MD, et al., Title: Congenital Anomalies Involving the Coronary Sinus, Circulation, Journal of the American Heart Association, vol. XXXIII, Feb. 1966, pp. 317-327.

(Continued)

*Primary Examiner* — Karen E Toth
(74) *Attorney, Agent, or Firm* — Klarquist Sparkman LLP

(57) ABSTRACT

A sensor implant device includes a shunt body that forms a fluid conduit, the fluid conduit having an axis, a first anchor structure associated with a first end of the shunt body, and a first sensor device coupled to the first anchor structure such that a sensor transducer of the first sensor device projects into a channel area defined by a radial boundary around the axis of the fluid conduit, the radial boundary being defined by the fluid conduit.

7 Claims, 27 Drawing Sheets

(56) References Cited

U.S. PATENT DOCUMENTS

| | | | |
|---|---|---|---|
| 4,256,094 | A | 3/1981 | Kapp et al. |
| 4,428,365 | A | 1/1984 | Hakky |
| 4,556,050 | A | 12/1985 | Hodgson et al. |
| 4,578,061 | A | 3/1986 | Lemelson |
| 4,586,501 | A | 5/1986 | Claracq |
| 4,601,718 | A | 7/1986 | Possis et al. |
| 4,655,777 | A | 4/1987 | Dunn et al. |
| 4,708,140 | A | 11/1987 | Baron |
| 4,712,551 | A | 12/1987 | Rayhanabad |
| 4,739,762 | A | 4/1988 | Palmaz |
| 4,762,128 | A | 8/1988 | Rosenbluth |
| 4,774,949 | A | 10/1988 | Fogarty |
| 4,828,544 | A | 5/1989 | Lane et al. |
| 4,861,336 | A | 8/1989 | Helzel |
| 4,881,939 | A | 11/1989 | Newman |
| 4,946,457 | A | 8/1990 | Elliott |
| 4,950,227 | A | 8/1990 | Savin et al. |
| 4,961,729 | A | 10/1990 | Vaillancourt |
| 4,997,431 | A | 3/1991 | Isner et al. |
| 5,026,377 | A | 6/1991 | Burton et al. |
| 5,054,492 | A | 10/1991 | Scribner et al. |
| 5,108,420 | A | 4/1992 | Marks |
| 5,109,420 | A | 4/1992 | Nonaka |
| 5,167,239 | A | 12/1992 | Cohen et al. |
| 5,190,528 | A | 3/1993 | Fonger et al. |
| 5,193,546 | A | 3/1993 | Shaknovich |
| 5,201,757 | A | 4/1993 | Heyn et al. |
| 5,242,397 | A | 9/1993 | Barath et al. |
| 5,242,410 | A | 9/1993 | Melker |
| 5,258,042 | A | 11/1993 | Mehta |
| 5,267,940 | A | 12/1993 | Moulder |
| 5,287,861 | A | 2/1994 | Wilk |
| 5,330,496 | A | 7/1994 | Alferness |
| 5,334,217 | A | 8/1994 | Das |
| 5,345,940 | A | 9/1994 | Seward et al. |
| 5,354,279 | A | 10/1994 | Hofling |
| 5,366,490 | A | 11/1994 | Edwards et al. |
| 5,373,849 | A | 12/1994 | Maroney et al. |
| 5,419,777 | A | 5/1995 | Hofling |
| 5,423,878 | A | 6/1995 | Franz |
| 5,429,634 | A | 7/1995 | Narciso, Jr. |
| 5,431,700 | A | 7/1995 | Sloan |
| 5,443,497 | A | 8/1995 | Venbrux |
| 5,445,600 | A | 8/1995 | Abdulla |
| 5,445,646 | A | 8/1995 | Euteneuer et al. |
| 5,456,284 | A | 10/1995 | Ryan et al. |
| 5,456,712 | A | 10/1995 | Maginot |
| 5,462,523 | A | 10/1995 | Samson et al. |
| 5,464,395 | A | 11/1995 | Faxon et al. |
| 5,491,224 | A | 2/1996 | Bittner et al. |
| 5,496,311 | A | 3/1996 | Abele et al. |
| 5,499,630 | A | 3/1996 | Hiki et al. |
| 5,507,724 | A | 4/1996 | Hofmann et al. |
| 5,507,725 | A | 4/1996 | Savage et al. |
| 5,538,504 | A | 7/1996 | Linden et al. |
| 5,551,954 | A | 9/1996 | Buscemi et al. |
| 5,554,182 | A | 9/1996 | Dinh et al. |
| 5,570,693 | A | 11/1996 | Jang et al. |
| 5,571,086 | A | 11/1996 | Kaplan et al. |
| 5,571,151 | A | 11/1996 | Gregory |
| 5,588,960 | A | 12/1996 | Edwards et al. |
| 5,597,378 | A | 1/1997 | Jervis |
| 5,599,300 | A | 2/1997 | Weaver et al. |
| 5,614,204 | A | 3/1997 | Cochrum |
| 5,628,784 | A | 5/1997 | Strecker |
| 5,661,133 | A | 8/1997 | Leiden et al. |
| 5,662,609 | A | 9/1997 | Slepian |
| 5,662,711 | A | 9/1997 | Douglas |
| 5,665,077 | A | 9/1997 | Rosen et al. |
| 5,669,880 | A | 9/1997 | Solar |
| 5,682,906 | A | 11/1997 | Sterman et al. |
| 5,690,670 | A | 11/1997 | Davidson |
| 5,693,029 | A | 12/1997 | Leonhardt |
| 5,704,361 | A | 1/1998 | Seward et al. |
| 5,704,926 | A | 1/1998 | Sutton |
| 5,713,363 | A | 2/1998 | Seward et al. |
| 5,713,853 | A | 2/1998 | Clark et al. |
| 5,718,725 | A | 2/1998 | Sterman et al. |
| 5,724,975 | A | 3/1998 | Negus et al. |
| 5,724,977 | A | 3/1998 | Yock et al. |
| 5,728,123 | A | 3/1998 | Lemelson et al. |
| 5,735,847 | A | 4/1998 | Gough et al. |
| 5,738,658 | A | 4/1998 | Maus et al. |
| 5,743,874 | A | 4/1998 | Fischell et al. |
| 5,755,682 | A | 5/1998 | Knudson et al. |
| 5,756,696 | A | 5/1998 | Gray et al. |
| 5,771,895 | A | 6/1998 | Slager |
| 5,772,629 | A | 6/1998 | Kaplan |
| 5,772,632 | A | 6/1998 | Forman |
| 5,807,258 | A | 9/1998 | Cimochowski et al. |
| 5,807,306 | A | 9/1998 | Shapland et al. |
| 5,810,780 | A | 9/1998 | Brimhall et al. |
| 5,814,005 | A | 9/1998 | Barra et al. |
| 5,827,216 | A | 10/1998 | Igo et al. |
| 5,830,222 | A | 11/1998 | Makower |
| 5,830,224 | A | 11/1998 | Cohn et al. |
| 5,836,913 | A | 11/1998 | Orth et al. |
| 5,843,090 | A | 12/1998 | Schuetz |
| 5,843,170 | A | 12/1998 | Ahn |
| 5,944,738 | A | 8/1999 | Amplatz et al. |
| 5,951,569 | A | 9/1999 | Tuckey et al. |
| 5,989,280 | A | 11/1999 | Euteneuer et al. |
| 6,019,788 | A | 2/2000 | Butters et al. |
| 6,042,589 | A | 3/2000 | Marianne |
| 6,053,891 | A | 4/2000 | DeCampli |
| 6,081,738 | A | 6/2000 | Hinohara et al. |
| 6,086,553 | A | 7/2000 | Akbik |
| 6,092,526 | A | 7/2000 | LaFontaine et al. |
| 6,095,878 | A | 8/2000 | Van Balen |
| 6,113,612 | A | 9/2000 | Swanson et al. |
| 6,120,494 | A | 9/2000 | Jonkman |
| 6,120,522 | A | 9/2000 | Vrba et al. |
| 6,120,534 | A | 9/2000 | Ruiz |
| 6,152,937 | A | 11/2000 | Peterson et al. |
| 6,165,185 | A | 12/2000 | Shennib et al. |
| 6,168,620 | B1 | 1/2001 | Kerr |
| 6,168,820 | B1 | 1/2001 | Garwood et al. |
| 6,174,681 | B1 | 1/2001 | Halling et al. |
| 6,190,353 | B1 | 2/2001 | Makower et al. |
| 6,193,734 | B1 | 2/2001 | Bolduc et al. |
| 6,196,230 | B1 | 3/2001 | Hall et al. |
| 6,241,743 | B1 | 6/2001 | Levin et al. |
| 6,248,117 | B1 | 6/2001 | Blatter |
| 6,251,116 | B1 | 6/2001 | Shennib et al. |
| 6,254,631 | B1 | 7/2001 | Thompson |
| 6,280,412 | B1 | 8/2001 | Pederson, Jr. et al. |
| 6,283,951 | B1 | 9/2001 | Flaherty et al. |
| 6,287,332 | B1 | 9/2001 | Bolz et al. |
| 6,290,728 | B1 | 9/2001 | Phelps et al. |
| 6,302,875 | B1 | 10/2001 | Makower et al. |
| 6,302,892 | B1 | 10/2001 | Wilk |
| 6,302,905 | B1 | 10/2001 | Goldsteen et al. |
| 6,309,415 | B1 | 10/2001 | Pulnev et al. |
| 6,315,752 | B1 | 11/2001 | DiMatteo |
| 6,325,798 | B1 | 12/2001 | Edwards et al. |
| 6,361,545 | B1 | 3/2002 | Macoviak et al. |
| 6,375,615 | B1 | 4/2002 | Flaherty et al. |
| 6,387,116 | B1 | 5/2002 | McKenzie et al. |
| 6,387,119 | B2 | 5/2002 | Wolf et al. |
| 6,391,036 | B1 | 5/2002 | Berg et al. |
| 6,402,767 | B1 | 6/2002 | Nash et al. |
| 6,443,158 | B1 | 9/2002 | LaFontaine et al. |
| 6,451,048 | B1 | 9/2002 | Berg et al. |
| 6,458,140 | B2 | 10/2002 | Akin et al. |
| 6,464,665 | B1 | 10/2002 | Heuser |
| 6,468,303 | B1 | 10/2002 | Amplatz et al. |
| 6,475,226 | B1 | 11/2002 | Belef et al. |
| 6,494,889 | B1 | 12/2002 | Fleischman et al. |
| 6,503,247 | B2 | 1/2003 | Swartz et al. |
| 6,506,201 | B2 | 1/2003 | Di Caprio et al. |
| 6,508,824 | B1 | 1/2003 | Flaherty et al. |
| 6,561,998 | B1 | 5/2003 | Roth et al. |
| 6,562,066 | B1 | 5/2003 | Martin |
| 6,565,542 | B2 | 5/2003 | Kumar et al. |

(56) References Cited

U.S. PATENT DOCUMENTS 6,575,168 B2 6/2003 LaFontaine et al.
6,579,311 B1 6/2003 Makower
6,589,251 B2 7/2003 Yee et al.
6,595,941 B1 7/2003 Blatter
6,602,241 B2 8/2003 Makower et al.
6,613,074 B1 9/2003 Mitelberg et al.
6,616,624 B1 9/2003 Kieval
6,616,675 B1 9/2003 Evard et al.
6,620,202 B2 9/2003 Bottcher et al.
6,623,494 B1 9/2003 Blatter
6,626,920 B2 9/2003 Whayne
6,638,293 B1 10/2003 Makower et al.
6,692,482 B2 2/2004 Heller et al.
6,695,878 B2 2/2004 McGuckin, Jr. et al.
6,699,256 B1 3/2004 Logan et al.
6,702,828 B2 3/2004 Whayne
6,709,414 B2 3/2004 Weitzel et al.
6,709,444 B1 3/2004 Makower
6,712,836 B1 3/2004 Berg et al.
6,719,804 B2 4/2004 St. Pierre
6,726,659 B1 4/2004 Stocking et al.
6,726,677 B1 4/2004 Flaherty et al.
6,736,825 B2 5/2004 Blatter et al.
6,740,426 B2 5/2004 Kawachi et al.
6,743,244 B2 6/2004 Blatter et al.
6,743,259 B2 6/2004 Ginn
6,746,426 B1 6/2004 Flaherty et al.
6,748,484 B1 6/2004 Henderson et al.
6,758,854 B1 7/2004 Butler et al.
6,776,785 B1 8/2004 Yencho et al.
6,797,083 B2 9/2004 Peterson
6,802,858 B2 10/2004 Gambale et al.
6,805,706 B2 10/2004 Solovay et al.
6,808,498 B2 10/2004 Laroya et al.
6,827,698 B1 12/2004 Kleinekofort
6,847,348 B2 1/2005 Rojewski
6,854,172 B2 2/2005 Kaese et al.
6,858,035 B2 2/2005 Whayne
6,869,437 B1 3/2005 Hausen et al.
6,893,413 B2 5/2005 Martin
6,913,600 B2 7/2005 Valley et al.
6,913,607 B2 7/2005 Ainsworth et al.
6,915,154 B1 7/2005 Docherty et al.
6,926,690 B2 8/2005 Renati
6,972,023 B2 12/2005 Whayne et al.
6,979,351 B2 12/2005 Forsell et al.
6,985,774 B2 1/2006 Kieval et al.
7,002,491 B2 2/2006 Robbins
7,008,397 B2 3/2006 Tweden et al.
7,011,094 B2 3/2006 Rapacki et al.
7,011,678 B2 3/2006 Tenerz et al.
7,025,741 B2 4/2006 Cull
7,025,746 B2 4/2006 Tal
7,037,329 B2 5/2006 Martin
7,056,294 B2 6/2006 Khairkhahan et al.
7,056,320 B2 6/2006 Utley et al.
7,056,325 B1 6/2006 Makower et al.
7,077,860 B2 7/2006 Yan et al.
7,083,631 B2 8/2006 Houser et al.
7,108,701 B2 9/2006 Evens et al.
7,115,136 B2 10/2006 Park et al.
7,118,546 B2 10/2006 Blatter
7,128,750 B1 10/2006 Stergiopulos
7,175,644 B2 2/2007 Cooper et al.
7,182,771 B1 2/2007 Houser et al.
7,235,095 B2 6/2007 Haverkost et al.
7,294,115 B1 11/2007 Wilk
7,316,706 B2 1/2008 Bloom et al.
7,317,951 B2 1/2008 Schneider et al.
7,318,804 B2 1/2008 Weitzel et al.
7,326,221 B2 2/2008 Sakamoto et al.
7,331,985 B2 2/2008 Thompson et al.
7,335,220 B2 2/2008 Khosravi et al.
7,351,247 B2 4/2008 Kupiecki et al.
7,361,181 B2 4/2008 Hindrichs et al.
7,374,567 B2 5/2008 Heuser
D581,054 S 11/2008 Moore
7,462,162 B2 12/2008 Phan et al.
7,476,200 B2 1/2009 Tal
7,530,963 B2 5/2009 Albright
7,563,277 B2 7/2009 Case et al.
7,623,926 B2 11/2009 Rossing et al.
7,625,593 B2 12/2009 Mandrusov et al.
7,628,768 B2 12/2009 Faul et al.
D612,499 S 3/2010 Ondracek et al.
7,691,110 B2 4/2010 Secrest et al.
7,699,863 B2 4/2010 Marco et al.
7,722,549 B2 5/2010 Nakao
7,722,665 B2 5/2010 Anwar et al.
7,744,621 B2 6/2010 Paul et al.
7,780,686 B2 8/2010 Park et al.
7,794,495 B2 9/2010 Gale et al.
7,807,191 B2 10/2010 Iyer et al.
7,815,590 B2 10/2010 Cooper
7,815,656 B2 10/2010 Rust et al.
7,815,852 B2 10/2010 Sternby
7,828,814 B2 11/2010 Brenneman et al.
7,846,179 B2 12/2010 Belef et al.
7,846,194 B2 12/2010 Hartley et al.
7,850,705 B2 12/2010 Bachinski et al.
7,867,547 B2 1/2011 Tochterman et al.
7,879,367 B2 2/2011 Heublein et al.
7,892,246 B2 2/2011 Akin et al.
7,892,247 B2 2/2011 Conston et al.
7,923,022 B2 4/2011 Wang et al.
7,951,194 B2 5/2011 Gueriguian et al.
7,959,603 B2 6/2011 Wahr et al.
7,964,210 B2 6/2011 Wang et al.
7,967,769 B2 6/2011 Faul et al.
7,972,346 B2 7/2011 Bachmann et al.
8,002,821 B2 8/2011 Stinson
8,016,782 B2 9/2011 Brenneman et al.
8,029,470 B2 10/2011 Whiting et al.
8,048,150 B2 11/2011 Weber et al.
8,052,751 B2 11/2011 Aklog et al.
8,057,534 B2 11/2011 Boismier et al.
8,070,708 B2 12/2011 Rottenberg et al.
8,088,171 B2 1/2012 Brenneman
8,089,029 B2 1/2012 Flanagan
8,091,556 B2 1/2012 Keren et al.
8,128,689 B2 3/2012 Weber et al.
8,152,773 B2 4/2012 Albrecht et al.
8,182,527 B2 5/2012 Llanos et al.
8,214,015 B2 7/2012 Macaulay et al.
8,221,495 B2 7/2012 Shrivastava et al.
8,226,592 B2 7/2012 Brenneman et al.
D665,500 S 8/2012 Martin et al.
8,282,591 B2 10/2012 Khan et al.
8,308,682 B2 11/2012 Kramer et al.
8,357,193 B2 1/2013 Phan et al.
8,376,979 B2 2/2013 Kapadia
8,382,697 B2 2/2013 Brenneman et al.
D679,015 S 3/2013 Nakaji
8,409,167 B2 4/2013 Roschak
8,500,697 B2 8/2013 Kurth et al.
8,506,984 B2 8/2013 Cook et al.
8,518,062 B2 8/2013 Cole et al.
8,518,662 B2 8/2013 Ritzen et al.
8,545,552 B2 10/2013 Garrison et al.
8,641,724 B2 2/2014 Brenneman et al.
8,657,790 B2 2/2014 Tal et al.
8,696,611 B2 4/2014 Nitzan et al.
D705,427 S 5/2014 Jagger et al.
8,768,487 B2 7/2014 Farnan et al.
8,784,860 B2 7/2014 Falotico et al.
8,882,830 B2 11/2014 Cartledge et al.
8,920,449 B2 12/2014 Wilkinson
8,926,545 B2 1/2015 Brenneman et al.
8,932,341 B2 1/2015 Brenneman
D723,166 S 2/2015 Igaki et al.
8,951,276 B2 2/2015 Kellerman et al.
9,005,155 B2 4/2015 Sugimoto
9,044,588 B2 6/2015 Conn
9,061,115 B2 6/2015 Ward et al.

(56) References Cited

U.S. PATENT DOCUMENTS 9,067,050 B2 6/2015 Gallagher et al.
9,198,756 B2 12/2015 Aklog et al.
9,232,997 B2 1/2016 Sugimoto et al.
9,277,995 B2 3/2016 Celermajer et al.
9,345,485 B2 5/2016 Dakin et al.
9,439,746 B2 9/2016 Bell et al.
9,456,812 B2 10/2016 Finch et al.
9,550,022 B2 1/2017 Brenneman et al.
9,649,480 B2 5/2017 Sugimoto et al.
9,681,948 B2 6/2017 Levi et al.
9,693,800 B2 7/2017 Aman et al.
9,775,636 B2 10/2017 Fazio et al.
9,789,294 B2 10/2017 Taft et al.
9,814,483 B2 11/2017 Vardi
9,827,404 B2 11/2017 Nance et al.
9,839,517 B2 12/2017 Centola et al.
9,872,981 B2 1/2018 Sparks et al.
9,980,815 B2 5/2018 Nitzan et al.
10,039,905 B1 8/2018 Taft et al.
10,076,403 B1 9/2018 Eigler et al.
10,130,371 B2 11/2018 Dehdashtian et al.
10,232,098 B2 3/2019 Brenneman et al.
10,272,230 B2 4/2019 Malek et al.
10,292,690 B2 5/2019 Celermajer et al.
10,327,746 B2 6/2019 Glimsdale et al.
10,413,284 B2 9/2019 McNamara et al.
10,426,482 B2 10/2019 Rafiee et al.
10,426,497 B2 10/2019 Chou et al.
10,433,851 B2 10/2019 Adams et al.
10,456,259 B2 10/2019 Subramanian et al.
10,543,113 B2 1/2020 Vong et al.
10,561,423 B2 2/2020 Sharma
10,565,835 B2 2/2020 Harrington et al.
10,568,751 B2 2/2020 McNamara
10,595,999 B2 3/2020 Vettukattil et al.
10,709,451 B2 7/2020 Gronberg et al.
10,835,394 B2 11/2020 Nae et al.
10,898,698 B1 1/2021 Eigler et al.
10,925,731 B2 2/2021 Bishop et al.
10,925,756 B2 2/2021 Perszyk
10,940,296 B2 3/2021 Keren
11,135,054 B2 10/2021 Nitzan et al.
11,135,410 B2 10/2021 Finch et al.
11,234,702 B1 * 2/2022 Eigler .................. A61B 5/6862
11,291,807 B2 4/2022 Eigler et al.
11,298,117 B2 4/2022 Hariton et al.
11,304,698 B2 4/2022 Sharma
11,395,644 B2 7/2022 Alanbaei
11,420,034 B2 8/2022 Solomon et al.
2001/0000041 A1 3/2001 Selmon et al.
2001/0025643 A1 10/2001 Foley
2001/0045698 A1 11/2001 Lo
2002/0013616 A1 1/2002 Carter et al.
2002/0029079 A1 3/2002 Kim et al.
2002/0062146 A1 5/2002 Makower et al.
2002/0169466 A1 11/2002 Peterson et al.
2002/0193751 A1 12/2002 Theeuwes et al.
2003/0017150 A1 1/2003 Torphy
2003/0060876 A1 3/2003 Loshakove et al.
2003/0065345 A1 4/2003 Weadock
2003/0120292 A1 6/2003 Park et al.
2003/0181928 A1 9/2003 Vidlund et al.
2003/0225425 A1 12/2003 Kupiecki et al.
2004/0064081 A1 4/2004 Stanish
2004/0087984 A1 5/2004 Kupiecki et al.
2004/0087997 A1 5/2004 Brenneman
2004/0092879 A1 5/2004 Kraus et al.
2004/0098105 A1 5/2004 Stinson et al.
2004/0215168 A1 10/2004 Verrier et al.
2004/0215220 A1 10/2004 Dolan et al.
2004/0215323 A1 10/2004 Stiger
2004/0230156 A1 11/2004 Schreck et al.
2004/0249335 A1 12/2004 Faul et al.
2004/0260318 A1 12/2004 Hunter et al.
2005/0021085 A1 1/2005 Abrams et al.
2005/0038501 A1 2/2005 Moore et al.
2005/0043708 A1 2/2005 Gleeson et al.
2005/0049675 A1 3/2005 Wallace
2005/0060041 A1 3/2005 Phan et al.
2005/0075655 A1 4/2005 Bumbalough et al.
2005/0075656 A1 4/2005 Beaupre
2005/0082226 A1 4/2005 Bene et al.
2005/0107723 A1 5/2005 Wehman et al.
2005/0149096 A1 7/2005 Hilal et al.
2005/0165344 A1 7/2005 Dobak
2005/0228402 A1 10/2005 Hofmann
2005/0249770 A1 11/2005 Hunter
2005/0249776 A1 11/2005 Chen et al.
2005/0272806 A1 12/2005 Falotico et al.
2006/0024359 A1 2/2006 Walker et al.
2006/0034466 A1 2/2006 Form et al.
2006/0047337 A1 3/2006 Brenneman
2006/0111704 A1 5/2006 Brenneman et al.
2006/0130591 A1 6/2006 Perkins
2006/0130767 A1 6/2006 Herchen
2006/0182536 A1 8/2006 Rice et al.
2006/0198869 A1 9/2006 Furst et al.
2006/0241342 A1 10/2006 Macaulay et al.
2006/0264801 A1 11/2006 Bolling et al.
2006/0264986 A1 11/2006 Park et al.
2006/0271196 A1 11/2006 Saal et al.
2006/0293701 A1 12/2006 Ainsworth et al.
2007/0083258 A1 4/2007 Falotico et al.
2007/0173787 A1 7/2007 Huang et al.
2007/0179426 A1 8/2007 Selden
2007/0213750 A1 9/2007 Weadock
2008/0021485 A1 1/2008 Catanese et al.
2008/0051883 A1 2/2008 Llanos et al.
2008/0091264 A1 4/2008 Machold et al.
2008/0109069 A1 5/2008 Coleman et al.
2008/0161904 A1 7/2008 Heuser et al.
2008/0167595 A1 7/2008 Porter et al.
2008/0234842 A1 9/2008 Zhang
2009/0125097 A1 5/2009 Bruszewski et al.
2009/0143713 A1 6/2009 Van Dam et al.
2009/0149947 A1 6/2009 Frohwitter
2009/0187116 A1 7/2009 Noishiki et al.
2009/0281379 A1 11/2009 Binmoeller et al.
2010/0030321 A1 2/2010 Mach
2010/0106171 A1 4/2010 Arepally et al.
2010/0198041 A1 8/2010 Christian et al.
2010/0217382 A1 8/2010 Chau et al.
2010/0268316 A1 10/2010 Brenneman et al.
2010/0298930 A1 11/2010 Orlov
2011/0096036 A1 4/2011 McIntosh et al.
2011/0106118 A1 5/2011 Son et al.
2011/0251482 A1 10/2011 Kellerman et al.
2012/0041544 A1 2/2012 Wolf
2012/0053686 A1 3/2012 McNamara et al.
2012/0143141 A1 6/2012 Verkaik et al.
2012/0265229 A1 10/2012 Rottenberg et al.
2013/0022214 A1 1/2013 Dickins et al.
2013/0030521 A1 1/2013 Nitzan et al.
2013/0178784 A1 7/2013 McNamara et al.
2013/0253342 A1 9/2013 Griswold et al.
2013/0281988 A1 10/2013 Magnin et al.
2014/0183828 A1 7/2014 Xu et al.
2014/0203939 A1 7/2014 Harrington et al.
2014/0222040 A1 8/2014 Park et al.
2014/0276395 A1 9/2014 Wilson et al.
2014/0277054 A1 9/2014 McNamara et al.
2014/0278442 A1 9/2014 Hong et al.
2015/0039084 A1 * 2/2015 Levi ...................... A61F 2/2409
623/2.38
2015/0119796 A1 4/2015 Finch
2015/0148731 A1 5/2015 Mcnamara et al.
2015/0151101 A1 6/2015 Bonnette et al.
2015/0238729 A1 8/2015 Jenson et al.
2016/0022293 A1 1/2016 Dubrul et al.
2016/0022970 A1 1/2016 Forcucci et al.
2016/0058452 A1 3/2016 Brenneman et al.
2016/0120550 A1 5/2016 McNamara et al.
2016/0220357 A1 8/2016 Anand et al.
2016/0270810 A1 9/2016 Vardi et al.

(56) References Cited

U.S. PATENT DOCUMENTS

| | | | |
|---|---|---|---|
| 2016/0296317 A1 | 10/2016 | Timmermans et al. | |
| 2016/0323977 A1 | 11/2016 | Sun et al. | |
| 2017/0090865 A1 | 3/2017 | Armstrong-Muntner et al. | |
| 2017/0106176 A1* | 4/2017 | Taft | A61M 27/008 |
| 2017/0113026 A1 | 4/2017 | Finch | |
| 2017/0128705 A1 | 5/2017 | Forcucci et al. | |
| 2017/0281339 A1 | 10/2017 | Levi et al. | |
| 2017/0303959 A1 | 10/2017 | Feng et al. | |
| 2017/0319823 A1 | 11/2017 | Yacoby et al. | |
| 2017/0340460 A1 | 11/2017 | Rosen et al. | |
| 2018/0177516 A1 | 6/2018 | Vardi et al. | |
| 2019/0008628 A1 | 1/2019 | Eigler et al. | |
| 2019/0269392 A1 | 9/2019 | Celermajer et al. | |
| 2019/0298909 A1 | 10/2019 | Cully et al. | |
| 2020/0054867 A1 | 2/2020 | Schwartz et al. | |
| 2020/0085600 A1 | 3/2020 | Schwartz et al. | |
| 2020/0101270 A1 | 4/2020 | Sutherland | |
| 2020/0170662 A1 | 6/2020 | Vardi et al. | |
| 2020/0187945 A1 | 6/2020 | Rowe et al. | |
| 2020/0254228 A1 | 8/2020 | Taft et al. | |
| 2020/0261704 A1 | 8/2020 | Wang et al. | |
| 2020/0289196 A1 | 9/2020 | Arevalos et al. | |
| 2020/0315599 A1 | 10/2020 | Nae et al. | |
| 2020/0368505 A1 | 11/2020 | Nae et al. | |
| 2020/0391016 A1 | 12/2020 | Passman et al. | |
| 2021/0007790 A1 | 1/2021 | Takahashi et al. | |
| 2021/0007791 A1 | 1/2021 | Takahashi et al. | |
| 2021/0007800 A1 | 1/2021 | Takahashi et al. | |
| 2021/0045691 A1 | 2/2021 | Zou et al. | |
| 2021/0059650 A1 | 3/2021 | Eidenschink et al. | |
| 2021/0077186 A1 | 3/2021 | Pate et al. | |
| 2021/0085935 A1 | 3/2021 | Fahey et al. | |
| 2021/0092522 A1 | 3/2021 | Draper et al. | |
| 2021/0121179 A1 | 4/2021 | Ben-David et al. | |
| 2021/0153776 A1 | 5/2021 | Minar et al. | |
| 2021/0161637 A1 | 6/2021 | Eigler et al. | |
| 2021/0177508 A1 | 6/2021 | Kellerman | |
| 2021/0236138 A1 | 8/2021 | Perszyk et al. | |
| 2021/0290214 A1 | 9/2021 | Cole et al. | |
| 2021/0369321 A1 | 12/2021 | Yang et al. | |
| 2021/0401494 A1 | 12/2021 | Passman et al. | |
| 2022/0001154 A1 | 1/2022 | Rowe et al. | |
| 2022/0008014 A1 | 1/2022 | Rowe et al. | |
| 2022/0031327 A1 | 2/2022 | Manash et al. | |
| 2022/0039667 A1 | 2/2022 | Schmitt et al. | |
| 2022/0039671 A1 | 2/2022 | Fahey | |
| 2022/0039833 A1 | 2/2022 | Thai et al. | |
| 2022/0088355 A1 | 3/2022 | Rabito et al. | |
| 2022/0096087 A1 | 3/2022 | Valdez | |
| 2022/0110679 A1 | 4/2022 | Wang et al. | |
| 2022/0142652 A1 | 5/2022 | Alexander et al. | |
| 2022/0151618 A1* | 5/2022 | Eigler | A61B 5/6862 |
| 2022/0151784 A1 | 5/2022 | Eigler et al. | |
| 2022/0168015 A1 | 6/2022 | Murray et al. | |
| 2022/0184356 A1 | 6/2022 | Nae et al. | |
| 2022/0202443 A1 | 6/2022 | Thai et al. | |
| 2022/0203078 A1 | 6/2022 | May | |
| 2022/0211380 A1 | 7/2022 | Pate | |
| 2022/0218352 A1 | 7/2022 | O'Halloran et al. | |
| 2022/0218964 A1 | 7/2022 | Fahey et al. | |
| 2022/0241564 A1 | 8/2022 | Shang et al. | |
| 2022/0241565 A1 | 8/2022 | Nae et al. | |
| 2022/0257904 A1 | 8/2022 | Passman et al. | |
| 2022/0273279 A1 | 9/2022 | Valdez et al. | |
| 2022/0280160 A1 | 9/2022 | Sharma | |
| 2022/0280760 A1 | 9/2022 | Thai et al. | |
| 2022/0296865 A1 | 9/2022 | Rafiee et al. | |
| 2022/0313234 A1 | 10/2022 | Mcnamara et al. | |
| 2022/0323012 A1 | 10/2022 | Pool et al. | |
| 2022/0323196 A1 | 10/2022 | Rafiee et al. | |
| 2022/0346936 A1 | 11/2022 | Scutti et al. | |
| 2022/0347446 A1 | 11/2022 | Fahey et al. | |
| 2022/0370120 A1 | 11/2022 | Yang et al. | |
| 2022/0379100 A1 | 12/2022 | Gutierrez et al. | |
| 2022/0387009 A1 | 12/2022 | Bukhdruker et al. | |
| 2023/0099410 A1 | 3/2023 | Primeaux | |
| 2023/0165672 A1 | 6/2023 | Fahey et al. | |
| 2023/0181214 A1 | 6/2023 | Vardi et al. | |
| 2023/0191093 A1 | 6/2023 | Nae et al. | |
| 2023/0263949 A1 | 8/2023 | Passman et al. | |
| 2023/0285133 A1 | 9/2023 | Eigler et al. | |
| 2023/0330398 A1 | 10/2023 | Nae et al. | |
| 2023/0371902 A1* | 11/2023 | Valdez | A61B 5/0215 |
| 2024/0081743 A1* | 3/2024 | Pool | A61B 5/0215 |

FOREIGN PATENT DOCUMENTS

| | | |
|---|---|---|
| WO | 2021091566 A1 | 5/2021 |
| WO | 2022031317 A1 | 2/2022 |
| WO | 2022060630 A1 | 3/2022 |
| WO | 2022133070 A1 | 6/2022 |
| WO | 2022169865 A1 | 8/2022 |
| WO | 2022177737 A1 | 8/2022 |
| WO | 2022197454 A1 | 9/2022 |
| WO | 2022197455 A1 | 9/2022 |
| WO | 2022232133 A1 | 11/2022 |
| WO | 2022246158 A1 | 11/2022 |
| WO | 2022246166 A1 | 11/2022 |
| WO | 2022271473 A1 | 12/2022 |
| WO | 2023022883 A1 | 2/2023 |
| WO | 2023027926 A1 | 3/2023 |
| WO | 2023079498 A1 | 5/2023 |
| WO | 2023081127 A1 | 5/2023 |
| WO | 2023081129 A1 | 5/2023 |
| WO | 2023154235 A1 | 8/2023 |
| WO | 2023154308 A1 | 8/2023 |
| WO | 2023172435 A1 | 9/2023 |
| WO | 2023172436 A1 | 9/2023 |
| WO | 2023196243 A1 | 10/2023 |
| WO | 2023239784 A1 | 12/2023 |
| WO | 2023239785 A1 | 12/2023 |
| WO | 2023239788 A2 | 12/2023 |

OTHER PUBLICATIONS

Kong, et al.—Creation Of An Intra-atrial Communication With A New Amplatzer Shunt Prosthesis, Catheterization and Cardiovascular Interventions 56:267-271 (2002).

P.K. Kong, et al., Title: Unroofed Coronary Sinus and Persistent Left Superior Vena Cava, The European Society of Cardiology, 2006, pp. 398401.

Ruebben et al., "Arteriovenous fistulas induced by femoral arterial catheterization: percutaneous treatment," Radiology, 209:729, 1998.

Vandhana Scheller, et al., Title: Coronary Sinus to Left Atrial Communication, Case Report in Medicine, Ohio Heart and Vascular Center, vol. 2009, Article ID 790715, pp. 13.

* cited by examiner

IMPLANT DEVICES WITH SHUNT CHANNEL SENSORS

RELATED APPLICATIONS

This application is a continuation of International Patent Application No. PCT/US2022/014858, filed Feb. 2, 2022, and entitled IMPLANT DEVICES WITH SHUNT CHANNEL SENSORS, which claims priority to United States Provisional Patent Application No. 63/150,031, filed Feb. 16, 2021 and entitled IMPLANT DEVICES WITH SHUNT CHANNEL SENSORS, the complete disclosures of which are hereby incorporated herein by reference in their entirety.

BACKGROUND

Field

The present disclosure generally relates to the field of medical implant devices.

Description of Related Art

Various medical procedures involve the implantation of a medical implant devices within the anatomy of the heart. Certain physiological parameters associated with such anatomy, such as fluid pressure, can have an impact on patient health prospects.

SUMMARY

Described herein are one or more methods and/or devices to facilitate monitoring of physiological parameter(s) associated with certain chambers and/or vessels of the heart, such as the left atrium, using one or more sensor implant devices.

In some implementations, the present disclosure relates to a sensor implant device comprising a shunt body that forms a fluid conduit, the fluid conduit having an axis, a first anchor structure associated with a first end of the shunt body, and a first sensor device coupled to the first anchor structure such that a sensor transducer of the first sensor device projects into a channel area defined by a radial boundary around the axis of the fluid conduit, the radial boundary being defined by the fluid conduit.

The first anchor structure can comprise an arm configured to extend radially outward from the axis of the fluid conduit.

In some embodiments, the first sensor device has a cylindrical form and, when the sensor implant device is in a deployed configuration in which the first anchor structure projects radially away from the axis of the fluid conduit, an axis of the first sensor device is substantially orthogonal to the axis of the fluid conduit.

The sensor implant device can further comprise a second anchor structure associated with a second end of the shunt body opposite the first end and a second sensor device coupled to the second anchor structure such that a sensor transducer of the second sensor device projects into the channel area. For example, the second anchor structure may emanate from an opposite area of the shunt body from an area of the shunt body from which the first anchor structure emanates. In some embodiments, the sensor transducer of the second sensor device faces in a substantially opposite direction from a direction in which the sensor transducer of the first sensor device faces.

The sensor implant device can further comprise a plurality of sensor retention fingers configured to hold the first sensor device to the first anchor structure.

In some embodiments, the first anchor structure is configured to extend axially with respect to the axis of the fluid conduit in a delivery configuration of the sensor implant device. For example, when the sensor implant device is in the delivery configuration, the sensor transducer of the first sensor device may be disposed within the fluid conduit. For example, the sensor transducer of the first sensor device can be disposed axially outside of the fluid conduit when the sensor implant device is in a deployed configuration.

In some implementations, the present disclosure relates to a sensor implant device comprising a shunt body that forms a fluid conduit, the fluid conduit having an axis, a first anchor means associated with a first end of the shunt body, and a first sensor device coupled to the first anchor means such that a sensor transducer of the first sensor device projects into a channel area defined by a radial boundary around the axis of the fluid conduit, the radial boundary being defined by the fluid conduit.

In some embodiments, the first anchor means comprises an arm configured to extend radially outward from the axis of the fluid conduit. For example, the arm can have a curved clamp form.

In some implementations, the present disclosure relates to a sensor implant device comprising a tubular frame having first and second diametrical sides and first and second axial ends, a first anchor arm associated with the first side and the first end of the tubular frame, a second anchor arm associated with the second side and the first end of the tubular frame, a third anchor arm associated with the first side and the second end of the tubular frame, a fourth anchor arm associated the second side and the second end of the tubular frame, each of the first, second, third, and fourth anchor arms having a base coupled to the tubular frame and a distal end, and a first sensor device coupled to the first anchor arm, the first sensor device including a sensor transducer associated with a sensor end of the first sensor device that is opposite a base end of the first sensor device. The sensor end of the first sensor device is associated with the base of the first anchor arm and the base end of the first sensor device is associated with the distal end of the first anchor arm.

In some embodiments, the sensor implant device is configured to assume a deployed configuration in which the first, second, third, and fourth anchor arms project radially away from the tubular frame. The sensor implant device can further comprise a second sensor device coupled to the fourth anchor arm, the second sensor device, wherein a sensor end of the second sensor device is associated with the base of the fourth anchor arm and the base end of the second sensor device is associated with the distal end of the fourth anchor arm. For example, the sensor end of the second sensor device and the sensor end of the first sensor device can both project radially over the tubular frame with respect to an axis of the tubular frame. In some embodiments, when the sensor implant device is in the deployed configuration, the sensor end of the first sensor device projects radially past the base of the first sensor arm with respect to an axis of the tubular frame.

The sensor implant device can be configured to assume a delivery configuration in which the first, second, third, and fourth anchor arms project axially away from the tubular frame. For example, when the sensor implant device is in the delivery configuration, the sensor end of the first sensor device and the sensor end of the second sensor device may be disposed within the tubular frame between the first and second axial ends of the tubular frame.

In some implementations, the present disclosure relates to a method of shunting fluid. The method comprises advancing a shunt implant device to a tissue wall within a delivery catheter, forming an opening in the tissue wall, deploying a first anchor structure of the shunt implant device on a distal side of the tissue wall, the first anchor structure having coupled thereto a sensor device, deploying a body of the shunt implant device in the opening in the tissue wall, and deploying a second anchor structure of the shunt implant device on a proximal side of the tissue wall. A sensor transducer of the sensor device projects into a channel area defined by a radial boundary around an axis of the body, the radial boundary being defined by the body.

For purposes of summarizing the disclosure, certain aspects, advantages, and novel features have been described. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

FIG. 9-1 illustrates a side view of a sensor implant device in accordance with one or more embodiments.

FIG. 9-2 illustrates a sensor assembly/device in accordance with one or more embodiments.

FIGS. 10-1, 10-2, and 10-3 show example channel areas associated with respective shunt body fluid conduits in accordance with one or more embodiments.

FIGS. 16-1, 16-2, 16-3, and 16-4 show a sensor implant device implanted in a coronary sinus tissue wall in various positions, respectively, in accordance with one or more embodiments.

FIGS. 23-1, 23-2, 23-3, 23-4, and 23-5 provide a flow diagram illustrating a process for implanting a sensor implant device in accordance with one or more embodiments.

FIGS. 24-1, 24-2, 24-3, 24-4, and 24-5 provide images of cardiac anatomy and certain devices/systems corresponding to operations of the process of FIGS. 23-1, 23-2, 23-3, 23-4, and 23-5 in accordance with one or more embodiments.

DETAILED DESCRIPTION

Figure 1:
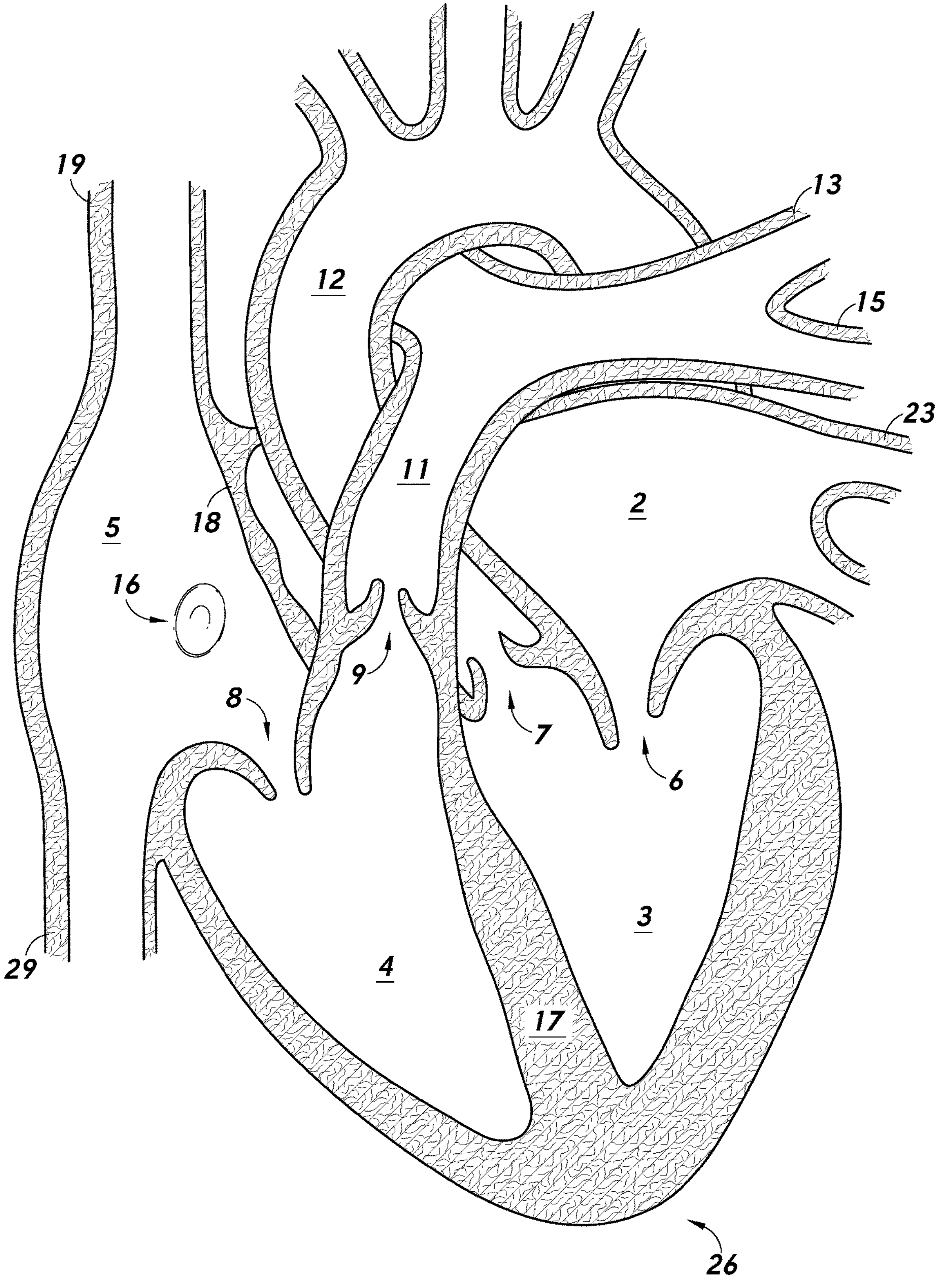
FIG. 1 illustrates an example representation of a human heart in accordance with one or more embodiments.

The headings provided herein are for convenience only and do not necessarily affect the scope or meaning of the claimed invention.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain reference numbers are re-used across different figures of the figure set of the present disclosure as a matter of convenience for devices, components, systems, features, and/or modules having features that may be similar in one or more respects. However, with respect to any of the embodiments disclosed herein, re-use of common reference numbers in the drawings does not necessarily indicate that such features, devices, components, or modules are identical or similar. Rather, one having ordinary skill in the art may be informed by context with respect to the degree to which usage of common reference numbers can imply similarity between referenced subject matter. Use of a particular reference number in the context of the description of a particular figure can be understood to relate to the identified device, component, aspect, feature, module, or system in that particular figure, and not necessarily to any devices, components, aspects, features, modules, or systems identified by the same reference number in another figure. Furthermore, aspects of separate figures identified with common reference numbers can be interpreted to share characteristics or to be entirely independent of one another.

Certain standard anatomical terms of location are used herein to refer to the anatomy of animals, and namely humans, with respect to the preferred embodiments. Although certain spatially relative terms, such as “outer,” “inner,” “upper,” “lower,” “below,” “above,” “vertical,” “horizontal,” “top,” “bottom,” and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as “above” another element/structure may represent a position that is below or beside such other element/structure with respect to alternate orientations of the subject patient or element/structure, and vice-versa.

The present disclosure relates to systems, devices, and methods for monitoring of one or more physiological parameters of a patient (e.g., blood pressure) using sensor-integrated cardiac shunts and/or other medical implant devices. In some implementations, the present disclosure relates to cardiac shunts and/or other cardiac implant devices that incorporate or are associated with pressure sensors or other sensor devices. The term “associated with” is used herein according to its broad and ordinary meaning. For example, where a first feature, element, component, device, or member is described as being “associated with” a second feature, element, component, device, or member, such description should be understood as indicating that the first feature, element, component, device, or member is physically coupled, attached, or connected to, integrated with, embedded at least partially within, or otherwise physically related to the second feature, element, component, device, or member, whether directly or indirectly. Certain embodiments are disclosed herein in the context of cardiac implant devices. However, although certain principles disclosed herein are particularly applicable to the anatomy of the heart, it should be understood that sensor implant devices in accordance with the present disclosure may be implanted in, or configured for implantation in, any suitable or desirable anatomy.

Cardiac Physiology

The anatomy of the heart is described below to assist in the understanding of certain inventive concepts disclosed herein. In humans and other vertebrate animals, the heart generally comprises a muscular organ having four pumping chambers, wherein the flow thereof is at least partially controlled by various heart valves, namely, the aortic, mitral (or bicuspid), tricuspid, and pulmonary valves. The valves may be configured to open and close in response to a pressure gradient present during various stages of the cardiac cycle (e.g., relaxation and contraction) to at least partially control the flow of blood to a respective region of the heart and/or to blood vessels (e.g., pulmonary, aorta, etc.).

FIG. 1 illustrates an example representation of a heart 1 having various features relevant to certain embodiments of the present inventive disclosure. The heart 1 includes four chambers, namely the left atrium 2, the left ventricle 3, the right ventricle 4, and the right atrium 5. In terms of blood flow, blood generally flows from the right ventricle 4 into the pulmonary artery 11 via the pulmonary valve 9, which separates the right ventricle 4 from the pulmonary artery 11 and is configured to open during systole so that blood may be pumped toward the lungs and close during diastole to prevent blood from leaking back into the heart from the pulmonary artery 11. The pulmonary artery 11 carries deoxygenated blood from the right side of the heart to the lungs.

In addition to the pulmonary valve 9, the heart 1 includes three additional valves for aiding the circulation of blood therein, including the tricuspid valve 8, the aortic valve 7, and the mitral valve 6. The tricuspid valve 8 separates the right atrium 5 from the right ventricle 4. The tricuspid valve 8 generally has three cusps or leaflets and may generally close during ventricular contraction (i.e., systole) and open during ventricular expansion (i.e., diastole). The mitral valve 6 generally has two cusps/leaflets and separates the left atrium 2 from the left ventricle 3. The mitral valve 6 is configured to open during diastole so that blood in the left atrium 2 can flow into the left ventricle 3, and, when functioning properly, closes during systole to prevent blood from leaking back into the left atrium 2. The aortic valve 7 separates the left ventricle 3 from the aorta 12. The aortic valve 7 is configured to open during systole to allow blood leaving the left ventricle 3 to enter the aorta 12, and close during diastole to prevent blood from leaking back into the left ventricle 3.

The heart valves may generally comprise a relatively dense fibrous ring, referred to herein as the annulus, as well as a plurality of leaflets or cusps attached to the annulus. Generally, the size of the leaflets or cusps may be such that when the heart contracts the resulting increased blood pressure produced within the corresponding heart chamber forces the leaflets at least partially open to allow flow from the heart chamber. As the pressure in the heart chamber subsides, the pressure in the subsequent chamber or blood vessel may become dominant and press back against the leaflets. As a result, the leaflets/cusps come in apposition to each other, thereby closing the flow passage. Disfunction of a heart valve and/or associated leaflets (e.g., pulmonary valve disfunction) can result in valve leakage and/or other health complications.

The atrioventricular (i.e., mitral and tricuspid) heart valves may further comprise a collection of chordae tendineae and papillary muscles (not shown) for securing the leaflets of the respective valves to promote and/or facilitate proper coaptation of the valve leaflets and prevent prolapse thereof. The papillary muscles, for example, may generally comprise finger-like projections from the ventricle wall. The valve leaflets are connected to the papillary muscles by the chordae tendineae. A wall of muscle, referred to as the septum, separates the left-side chambers from the right-side chambers. In particular, an atrial septum wall portion 18 (referred to herein as the “atrial septum,” “atrial septum,” or “septum”) separates the left atrium 2 from the right atrium 5, whereas a ventricular septum wall portion 17 (referred to herein as the “ventricular septum,” “interventricular septum,” or “septum”) separates the left ventricle 3 from the right ventricle 4. The inferior tip of the heart 1 is referred to as the apex and is generally located on or near the midclavicular line, in the fifth intercostal space.

The coronary sinus 16 comprises a collection of veins joined together to form a large vessel that collects blood from the heart muscle (myocardium). The ostium of the coronary sinus, which can be guarded at least in part by a Thebesian valve in some patients, is open to the right atrium 5, as shown. The coronary sinus runs along a posterior aspect of the left atrium 2 and delivers less-oxygenated blood to the right atrium 5. The coronary sinus generally runs transversely in the left atrioventricular groove on the posterior side of the heart.

Health Conditions Associated with Cardiac Pressure and Other Parameters

As referenced above, certain physiological conditions or parameters associated with the cardiac anatomy can impact the health of a patient. For example, congestive heart failure is a condition associated with the relatively slow movement of blood through the heart and/or body, which causes the fluid pressure in one or more chambers of the heart to increase. As a result, the heart does not pump sufficient oxygen to meet the body’s needs. The various chambers of the heart may respond to pressure increases by stretching to hold more blood to pump through the body or by becoming relatively stiff and/or thickened. The walls of the heart can eventually weaken and become unable to pump as efficiently. In some cases, the kidneys may respond to cardiac inefficiency by causing the body to retain fluid. Fluid build-up in arms, legs, ankles, feet, lungs, and/or other organs can cause the body to become congested, which is referred to as congestive heart failure. Acute decompensated congestive heart failure is a leading cause of morbidity and mortality, and therefore treatment and/or prevention of congestive heart failure is a significant concern in medical care.

The treatment and/or prevention of heart failure (e.g., congestive heart failure) can advantageously involve the monitoring of pressure in one or more chambers or regions of the heart or other anatomy. As described above, pressure buildup in one or more chambers or areas of the heart can be associated with congestive heart failure. Without direct or indirect monitoring of cardiac pressure, it can be difficult to infer, determine, or predict the presence or occurrence of congestive heart failure. For example, treatments or approaches not involving direct or indirect pressure monitoring may involve measuring or observing other present physiological conditions of the patient, such as measuring body weight, thoracic impedance, right heart catheterization, or the like. In some solutions, pulmonary capillary wedge pressure can be measured as a surrogate of left atrial pressure. For example, a pressure sensor may be disposed or implanted in the pulmonary artery, and readings associated therewith may be used as a surrogate for left atrial pressure. However, with respect to catheter-based pressure measurement in the pulmonary artery or certain other chambers or regions of the heart, use of invasive catheters may be required to maintain such pressure sensors, which may be uncomfortable or difficult to implement. Furthermore, certain lung-related conditions may affect pressure readings in the pulmonary artery, such that the correlation between pulmonary artery pressure and left atrial pressure may be undesirably attenuated. As an alternative to pulmonary artery pressure measurement, pressure measurements in the right ventricle outflow tract may relate to left atrial pressure as well. However, the correlation between such pressure readings and left atrial pressure may not be sufficiently strong to be utilized in congestive heart failure diagnostics, prevention, and/or treatment.

Additional solutions may be implemented for deriving or inferring left atrial pressure. For example, the E/A ratio, which is a marker of the function of the left ventricle of the heart representing the ratio of peak velocity blood flow from gravity in early diastole (the E wave) to peak velocity flow in late diastole caused by atrial contraction (the A wave), can be used as a surrogate for measuring left atrial pressure. The F/A ratio may be determined using echocardiography or other imaging technology; generally, abnormalities in the E/A ratio may suggest that the left ventricle cannot fill with blood properly in the period between contractions, which may lead to symptoms of heart failure, as explained above. However, E/A ratio determination generally does not provide absolute pressure measurement values.

Various methods for identifying and/or treating congestive heart failure involve the observation of worsening congestive heart failure symptoms and/or changes in body weight. However, such signs may appear relatively late and/or be relatively unreliable. For example, daily body-weight measurements may vary significantly (e.g., up to 9% or more) and may be unreliable in signaling heart-related complications. Furthermore, treatments guided by monitoring signs, symptoms, weight, and/or other biomarkers have not been shown to substantially improve clinical outcomes. In addition, for patients that have been discharged, such treatments may necessitate remote telemedicine systems.

The present disclosure provides systems, devices, and methods for guiding the administration of medication relating to the treatment of congestive heart failure at least in part by directly monitoring pressure in the left atrium, or other chamber or vessel for which pressure measurements are indicative of left atrial pressure and/or pressure levels in one or more other vessels/chambers, such as for congestive heart failure patients in order to reduce hospital readmissions, morbidity, and/or otherwise improve the health prospects of the patient.

Cardiac Pressure Monitoring

Cardiac pressure monitoring in accordance with embodiments of the present disclosure may provide a proactive intervention mechanism for preventing or treating congestive heart failure and/or other physiological conditions. Generally, increases in ventricular filling pressures associated with diastolic and/or systolic heart failure can occur prior to the occurrence of symptoms that lead to hospitalization. For example, cardiac pressure indicators may present weeks prior to hospitalization with respect to some patients. Therefore, pressure monitoring systems in accordance with embodiments of the present disclosure may advantageously be implemented to reduce instances of hospitalization by guiding the appropriate or desired titration and/or administration of medications before the onset of heart failure.

Dyspnea represents a cardiac pressure indicator characterized by shortness of breath or the feeling that one cannot breathe well enough. Dyspnea may result from elevated atrial pressure, which may cause fluid buildup in the lungs from pressure back-up. Pathological dyspnea can result from congestive heart failure. However, a significant amount of time may elapse between the time of initial pressure elevation and the onset of dyspnea, and therefore symptoms of dyspnea may not provide sufficiently-early signaling of elevated atrial pressure. By monitoring pressure directly according to embodiments of the present disclosure, normal ventricular filling pressures may advantageously be maintained, thereby preventing or reducing effects of heart failure, such as dyspnea.

Figure 2:
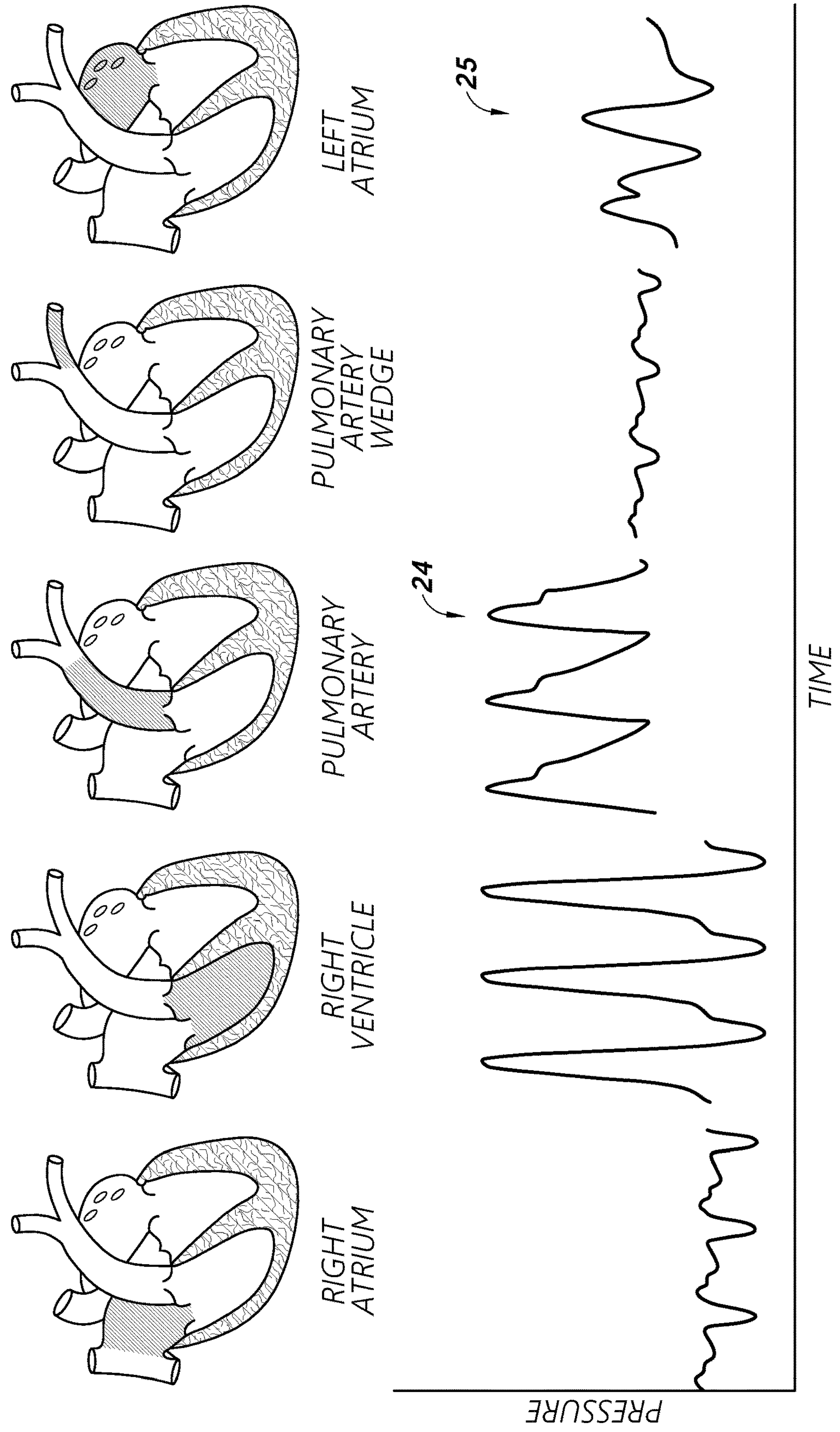
FIG. 2 illustrates example pressure waveforms associated with various chambers and vessels of the heart according to one or more embodiments.

As referenced above, with respect to cardiac pressures, pressure elevation in the left atrium may be particularly correlated with heart failure. FIG. 2 illustrates example pressure waveforms associated with various chambers and vessels of the heart according to one or more embodiments. The various waveforms illustrated in FIG. 2 may represent waveforms obtained using right heart catheterization to advance one or more pressure sensors to the respective illustrated and labeled chambers or vessels of the heart. As illustrated in FIG. 2, the waveform 25, which represents left atrial pressure, may be considered to provide the best feedback for early detection of congestive heart failure. Furthermore, there may generally be a relatively strong correlation between increases and left atrial pressure and pulmonary congestion.

Left atrial pressure may generally correlate well with left ventricular end-diastolic pressure. However, although left atrial pressure and end-diastolic pulmonary artery pressure can have a significant correlation, such correlation may be weakened when the pulmonary vascular resistance becomes elevated. That is, pulmonary artery pressure generally fails to correlate adequately with left ventricular end-diastolic pressure in the presence of a variety of acute conditions, which may include certain patients with congestive heart failure. For example, pulmonary hypertension, which affects approximately 25% to 83% of patients with heart failure, can affect the reliability of pulmonary artery pressure measurement for estimating left-sided filling pressure. Therefore, pulmonary artery pressure measurement alone, as represented by the waveform 24, may be an insufficient or inaccurate indicator of left ventricular end-diastolic pressure, particularly for patients with co-morbidities, such as lung disease and/or thromboembolism. Left atrial pressure may further be correlated at least partially with the presence and/or degree of mitral regurgitation.

Left atrial pressure readings may be relatively less likely to be distorted or affected by other conditions, such as respiratory conditions or the like, compared to the other pressure waveforms shown in FIG. 2. Generally, left atrial pressure may be significantly predictive of heart failure, such as up two weeks before manifestation of heart failure. For example, increases in left atrial pressure, and both diastolic and systolic heart failure, may occur weeks prior to hospitalization, and therefore knowledge of such increases may be used to predict the onset of congestive heart failure, such as acute debilitating symptoms of congestive heart failure.

Cardiac pressure monitoring, such as left atrial pressure monitoring, can provide a mechanism to guide administration of medication to treat and/or prevent congestive heart failure. Such treatments may advantageously reduce hospital readmissions and morbidity, as well as provide other benefits. An implanted pressure sensor in accordance with embodiments of the present disclosure may be used to predict heart failure up two weeks or more before the manifestation of symptoms or markers of heart failure (e.g., dyspnea). When heart failure predictors are recognized using cardiac pressure sensor embodiments in accordance with the present disclosure, certain prophylactic measures may be implemented, including medication intervention, such as modification to a patient's medication regimen, which may help prevent or reduce the effects of cardiac dysfunction. Direct pressure measurement in the left atrium can advantageously provide an accurate indicator of pressure buildup that may lead to heart failure or other complications. For example, trends of atrial pressure elevation may be analyzed or used to determine or predict the onset of cardiac dysfunction, wherein drug or other therapy may be augmented to cause reduction in pressure and prevent or reduce further complications.

Figure 3:
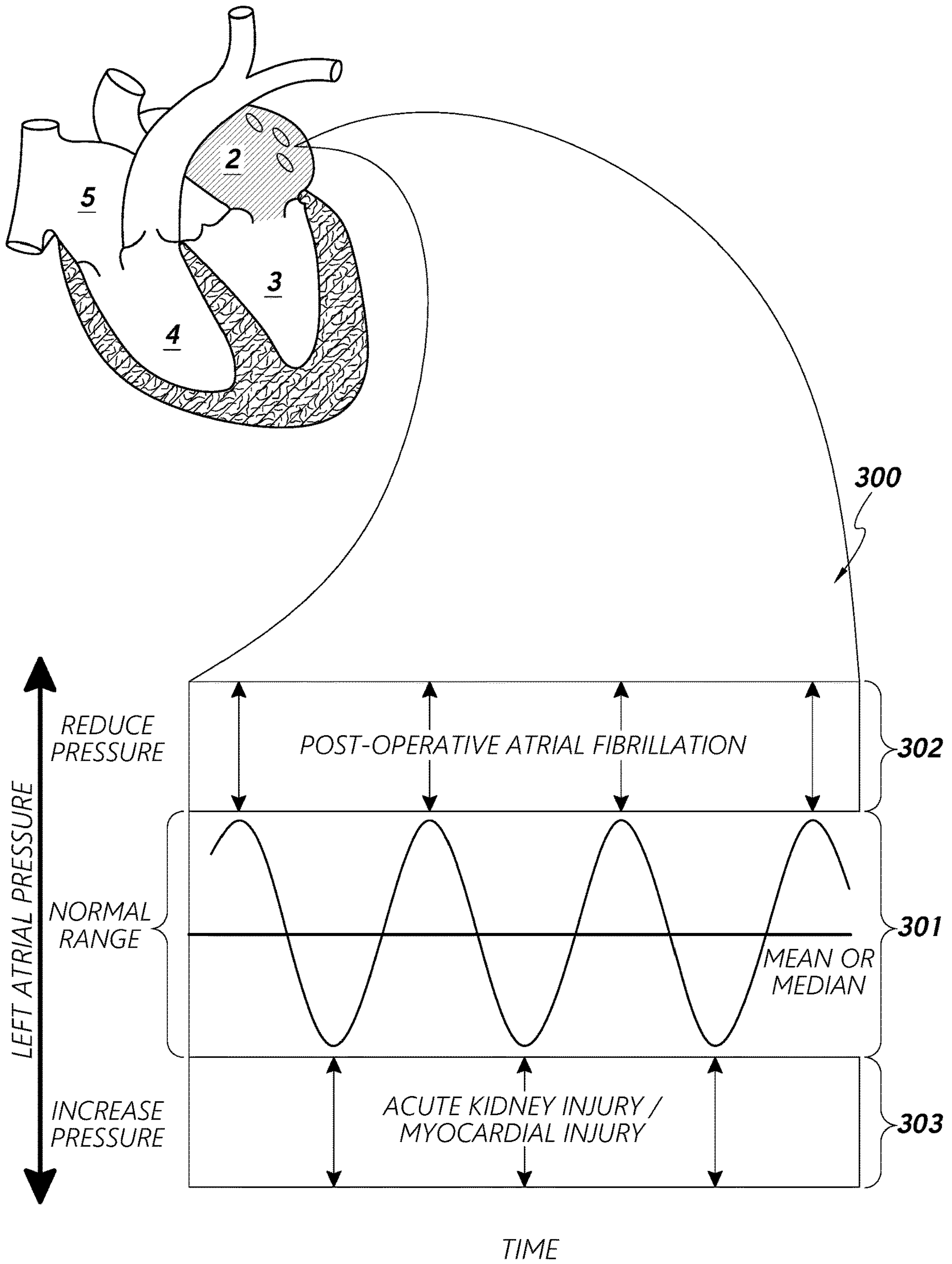
FIG. 3 illustrates a graph showing left atrial pressure ranges.

FIG. 3 illustrates a graph 300 showing left atrial pressure ranges including a normal range 301 of left atrial pressure that is not generally associated with substantial risk of postoperative atrial fibrillation, acute kidney injury, myocardial injury, heart failure and/or other health conditions. Embodiments of the present disclosure provide systems, devices, and methods for determining whether a patient's left atrial pressure is within the normal range 301, above the normal range 303, or below the normal range 302 through the use of certain sensor implant devices. For detected left atrial pressure above the normal range, which may be correlated with an increased risk of heart failure, embodiments of the present disclosure as described in detail below can inform efforts to reduce the left atrial pressure until it is brought within the normal range 301. Furthermore, for detected left atrial pressure that is below the normal range 301, which may be correlated with increased risks of acute kidney injury, myocardial injury, and/or other health complications, embodiments of the present disclosure as described in detail below can serve to facilitate efforts to increase the left atrial pressure to bring the pressure level within the normal range 301.

Implant Devices with Integrated Sensors

Figure 4:
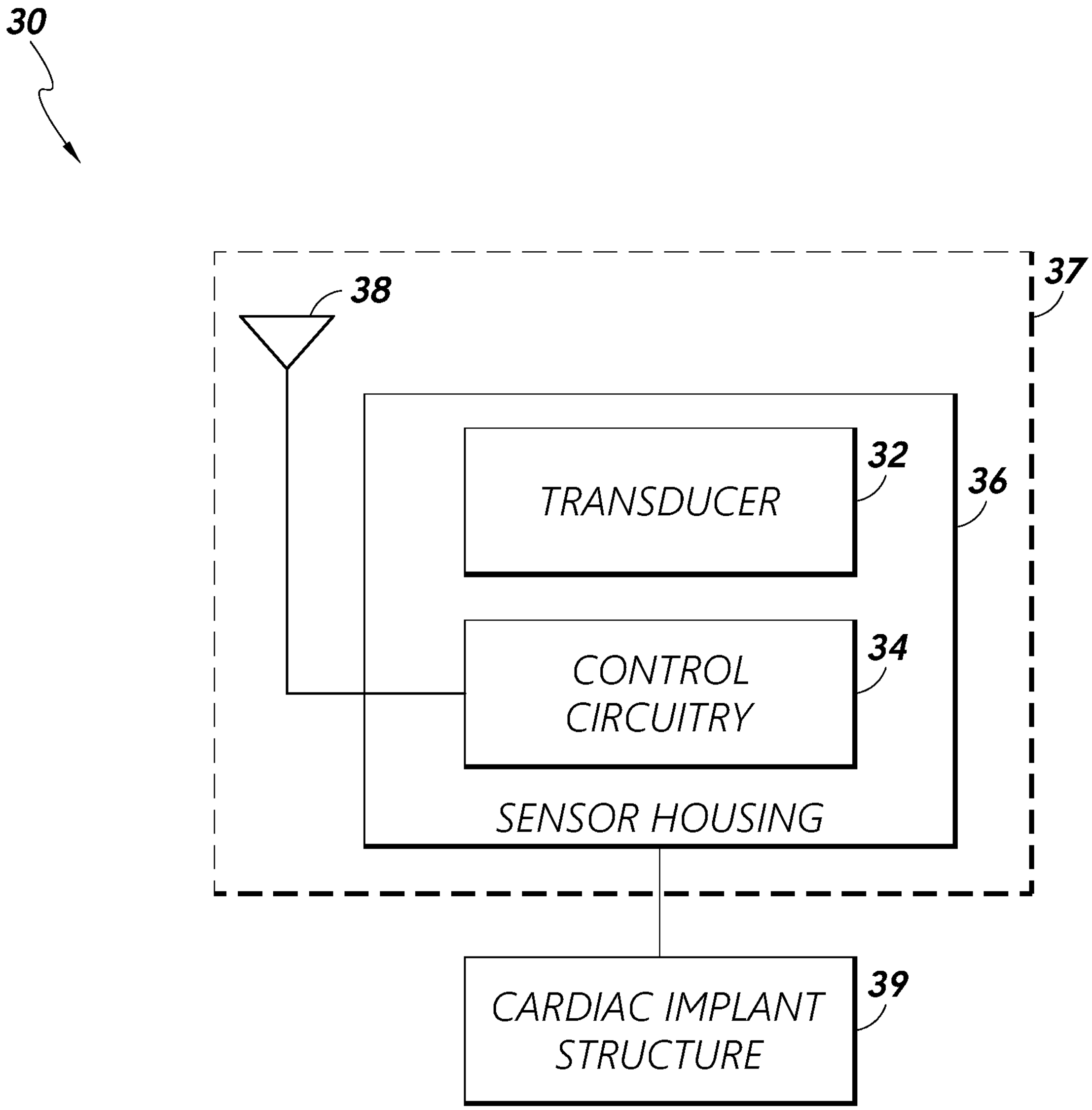
FIG. 4 is a block diagram representing an implant device in accordance with one or more embodiments.

In some implementations, the present disclosure relates to sensors associated or integrated with cardiac shunts or other implant devices. Such integrated devices may be used to provide controlled and/or more effective therapies for treating and preventing heart failure and/or other health complications related to cardiac function. FIG. 4 is a block diagram illustrating an implant device 30 comprising a shunt (or other type of implant) structure 39. In some embodiments, the shunt structure 39 is physically integrated with and/or connected to a sensor device 37. The sensor device 37 may be, for example, a pressure sensor, or other type of sensor. In some embodiments, the sensor 37 comprises a transducer 32, such as a pressure transducer, as well as certain control circuitry 34, which may be embodied in, for example, an application-specific integrated circuit (ASIC).

The control circuitry 34 may be configured to process signals received from the transducer 32 and/or communicate signals associated therewith wirelessly through biological tissue using the antenna 38. The term "control circuitry" is used herein according to its broad and ordinary meaning, and may refer to any collection of processors, processing circuitry, processing modules/units, chips, dies (e.g., semiconductor dies including come or more active and/or passive devices and/or connectivity circuitry), microprocessors, micro-controllers, digital signal processors, microcomputers, central processing units, field programmable gate arrays, programmable logic devices, state machines (e.g., hardware state machines), logic circuitry, analog circuitry, digital circuitry, and/or any device that manipulates signals (analog and/or digital) based on hard coding of the circuitry and/or operational instructions. Control circuitry referenced herein may further comprise one or more, storage devices, which may be embodied in a single memory device, a plurality of memory devices, and/or embedded circuitry of a device. Such data storage may comprise read-only memory, random access memory, volatile memory, non-volatile memory, static memory, dynamic memory, flash memory, cache memory, data storage registers, and/or any device that stores digital information. It should be noted that in embodiments in which control circuitry comprises a hardware and/or software state machine, analog circuitry, digital circuitry, and/or logic circuitry, data storage device(s)/register(s) storing any associated operational instructions may be embedded within, or external to, the circuitry comprising the state machine, analog circuitry, digital circuitry, and/or logic circuitry. The transducer(s) 32 and/or antenna(s) 38 can be considered part of the control circuitry 34.

The antenna 38 may comprise one or more coils or loops of conductive material, such as copper wire or the like. In some embodiments, at least a portion of the transducer 32, control circuitry 34, and/or the antenna 38 are at least partially disposed or contained within a sensor housing 36, which may comprise any type of material, and may advantageously be at least partially hermetically sealed. For example, the housing 36 may comprise glass or other rigid material in some embodiments, which may provide mechanical stability and/or protection for the components housed therein. In some embodiments, the housing 36 is at least partially flexible. For example, the housing may comprise polymer or other flexible structure/material, which may advantageously allow for folding, bending, or collapsing of the sensor 37 to allow for transportation thereof through a catheter or other introducing means.

The transducer 32 may comprise any type of sensor means or mechanism. For example, the transducer 32 may be a force-collector-type pressure sensor. In some embodiments, the transducer 32 comprises a diaphragm, piston, bourdon tube, bellows, or other strain- or deflection-measuring component(s) to measure strain or deflection applied over an area/surface thereof. The transducer 32 may be associated with the housing 36, such that at least a portion thereof is contained within or attached to the housing 36. With respect to sensor devices/components being "associated with" a stent or other implant structure, such terminology may refer to a sensor device or component being physically coupled, attached, or connected to, or integrated with, the implant structure.

In some embodiments, the transducer 32 comprises or is a component of a piezoresistive strain gauge, which may be configured to use a bonded or formed strain gauge to detect strain due to applied pressure, wherein resistance increases as pressure deforms the component/material. The transducer 32 may incorporate any type of material, including but not limited to silicon (e.g., monocrystalline), polysilicon thin film, bonded metal foil, thick film, silicon-on-sapphire, sputtered thin film, and/or the like.

In some embodiments, the transducer 32 comprises or is a component of a capacitive pressure sensor including a diaphragm and pressure cavity configured to form a variable capacitor to detect strain due to pressure applied to the diaphragm. The capacitance of the capacitive pressure sensor may generally decrease as pressure deforms the diaphragm. The diaphragm may comprise any material(s), including but not limited to metal, ceramic, silicon, and the like. In some embodiments, the transducer 32 comprises or is a component of an electromagnetic pressure sensor, which may be configured to measure the displacement of a diaphragm by means of changes in inductance, linear variable displacement transducer (LVDT) functionality. Hall Effect, or eddy current sensing. In some embodiments, the transducer 32 comprises or is a component of a piezoelectric strain sensor. For example, such a sensor may determine strain (e.g., pressure) on a sensing mechanism based on the piezoelectric effect in certain materials, such as quartz.

In some embodiments, the transducer 32 comprises or is a component of a strain gauge. For example, a strain gauge embodiment may comprise a pressure sensitive element on or associated with an exposed surface of the transducer 32. In some embodiments, a metal strain gauge is adhered to a surface of the sensor, or a thin-film gauge may be applied on the sensor by sputtering or other technique. The measuring element or mechanism may comprise a diaphragm or metal foil. The transducer 32 may comprise any other type of sensor or pressure sensor, such as optical, potentiometric, resonant, thermal, ionization, or other types of strain or pressure sensors.

Figure 5:
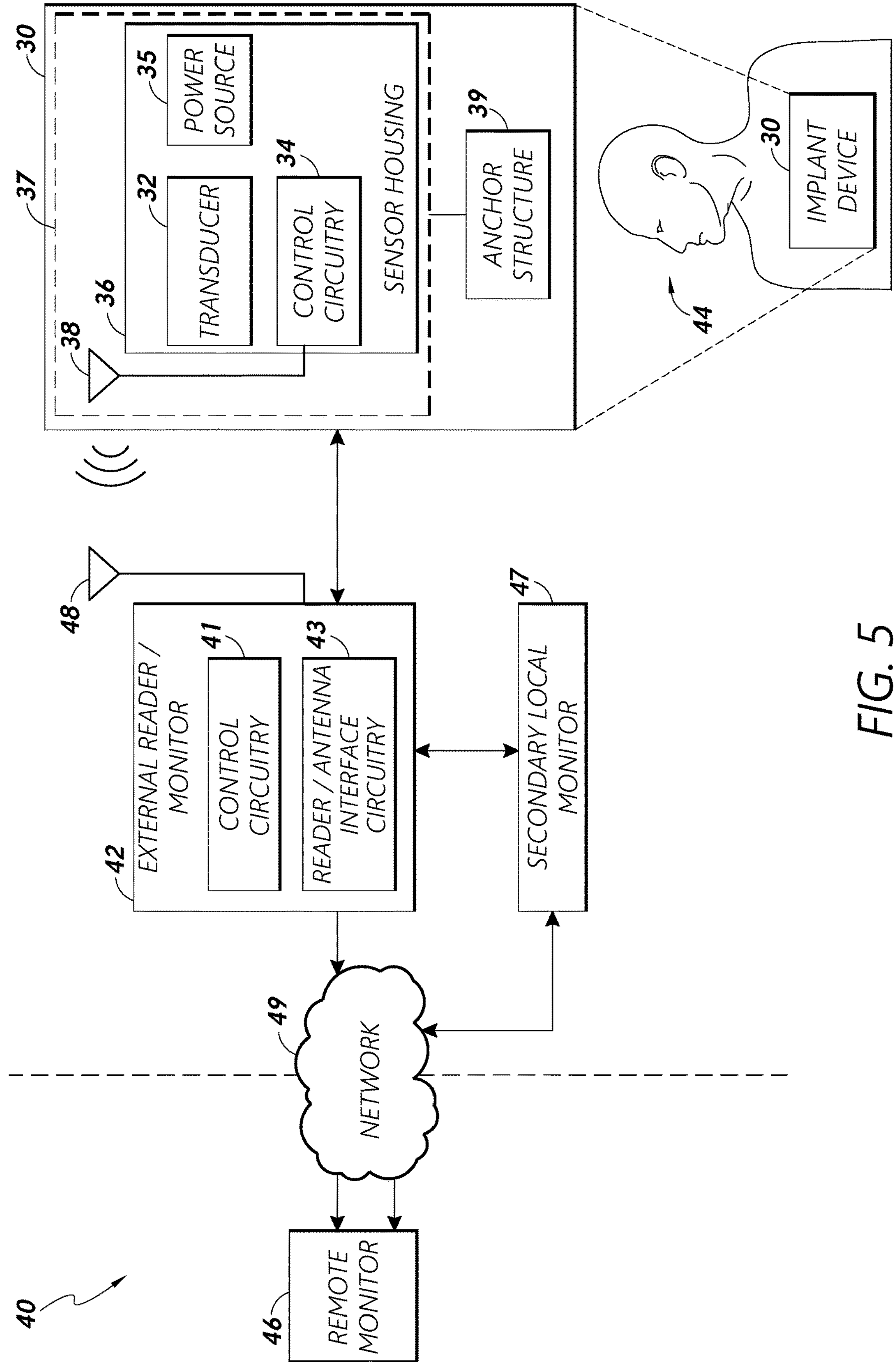
FIG. 5 is a block diagram representing a system for monitoring one or more physiological parameters associated with a patient according to one or more embodiments.

FIG. 5 shows a system 40 for monitoring one or more physiological parameters (e.g., left atrial pressure and/or volume) in a patient 44 according to one or more embodiments. The patient 44 can have a medical implant device 30 implanted in, for example, the heart (not shown), or associated physiology, of the patient 44. For example, the implant device 30 can be implanted at least partially within the left atrium and/or coronary sinus of the patient's heart. The implant device 30 can include one or more sensor transducers 32, such as one or more microelectromechanical system (M EMS) devices (e.g., MEMS pressure sensors, or other type of sensor transducer).

In certain embodiments, the monitoring system 40 can comprise at least two subsystems, including an implantable internal subsystem or device 30 that includes the sensor transducer(s) 32, as well as control circuitry 34 comprising one or more microcontroller(s), discrete electronic component(s), and one or more power and/or data transmitter(s) 38 (e.g., antennae coil). The monitoring system 40 can further include an external (e.g., non-implantable) subsystem that includes an external reader 42 (e.g., coil), which may include a wireless transceiver that is electrically and/or communicatively coupled to certain control circuitry 41. In certain embodiments, both the internal 30 and external 42 subsystems include a corresponding coil antenna for wireless communication and/or power delivery through patient tissue disposed therebetween. The sensor implant device 30 can be any type of implant device. For example, in some embodiments, the implant device 30 comprises a pressure sensor integrated with another functional implant structure 39, such as a prosthetic shunt or stent device/structure.

Certain details of the implant device 30 are illustrated in the enlarged block 30 shown. The implant device 30 can comprise an implant/anchor structure 39 as described herein. For example, the implant/anchor structure 39 can include a percutaneously-deliverable shunt device configured to be secured to and/or in a tissue wall to provide a flow path between two chambers and/or vessels of the heart, as described in detail throughout the present disclosure. Although certain components are illustrated in FIG. 5 as part of the implant device 30, it should be understood that the sensor implant device 30 may only comprise a subset of the illustrated components/modules and can comprise additional components/modules not illustrated. The implant device may represent an embodiment of the implant device shown in FIG. 4, and vice versa. The implant device 30 can advantageously include one or more sensor transducers 32, which can be configured to provide a response indicative of one or more physiological parameters of the patient 44, such as atrial pressure. Although pressure transducers are described, the sensor transducer(s) 32 can comprise any suitable or desirable types of sensor transducer(s) for providing signals relating to physiological parameters or conditions associated with the implant device 30 and/or patient 44.

The sensor transducer(s) 32 can comprise one or more MEMS sensors, optical sensors, piezoelectric sensors, electromagnetic sensors, strain sensors/gauges, accelerometers, gyroscopes, diaphragm-based sensors, and/or other types of sensors, which can be positioned in the patient 44 to sense one or more parameters relevant to the health of the patient. The transducer 32 may be a force-collector-type pressure sensor. In some embodiments, the transducer 32 comprises a diaphragm, piston, bourdon tube, bellows, or other strain- or deflection-measuring component(s) to measure strain or deflection applied over an area/surface thereof. The transducer 32 may be associated with the sensor housing 36, such that at least a portion thereof is contained within, or attached to, the housing 36.

In some embodiments, the transducer 32 comprises or is a component of a strain gauge, which may be configured to use a bonded or formed strain gauge to detect strain due to applied pressure. For example, the transducer 32 may comprise or be a component of a piezoresistive strain gauge, wherein resistance increases as pressure deforms the component/material of the strain gauge. The transducer 32 may incorporate any type of material, including but not limited to silicone, polymer, silicon (e.g., monocrystalline), polysilicon thin film, bonded metal foil, thick film, silicon-on-sapphire, sputtered thin film, and/or the like. In some embodiments, a metal strain gauge is adhered to the sensor surface, or a thin-film gauge may be applied on the sensor by sputtering or other technique. The measuring element or mechanism may comprise a diaphragm or metal foil. The transducer 32 may comprise any other type of sensor or pressure sensor, such as optical, potentiometric, resonant, thermal, ionization, or other types of strain or pressure sensors.

In some embodiments, the transducer 32 comprises or is a component of a capacitive pressure sensor including a diaphragm and pressure cavity configured to form a variable capacitor to detect strain due to pressure applied to the diaphragm. The capacitance of the capacitive pressure sensor may generally decrease as pressure deforms the diaphragm. The diaphragm may comprise any material(s), including but not limited to metal, ceramic, silicone, silicon or other semiconductor, and the like. In some embodiments, the transducer 32 comprises or is a component of an electromagnetic pressure sensor, which may be configured to measures the displacement of a diaphragm by means of changes in inductance, linear variable displacement transducer (LVDT) functionality, Hall Effect. or eddy current sensing. In some embodiments, the transducer 32 comprises or is a component of a piezoelectric strain sensor. For example, such a sensor may determine strain (e.g., pressure) on a sensing mechanism based on the piezoelectric effect in certain materials, such as quartz.

In some embodiments, the transducer(s) 32 is/are electrically and/or communicatively coupled to the control circuitry 34, which may comprise one or more application-specific integrated circuit (ASIC) microcontrollers or chips. The control circuitry 34 can further include one or more discrete electronic components, such as tuning capacitors, resistors, diodes, inductors, or the like.

In certain embodiments, the sensor transducer(s) 32 can be configured to generate electrical signals that can be wirelessly transmitted to a device outside the patient's body, such as the illustrated local external monitor system 42. In order to perform such wireless data transmission, the implant device 30 can include radio frequency (RF) (or other frequency band) transmission circuitry, such as signal processing circuitry and an antenna 38. The antenna 38 can comprise an antenna coil implanted within the patient. The control circuitry 34 may comprise any type of transceiver circuitry configured to transmit an electromagnetic signal, wherein the signal can be radiated by the antenna 38, which may comprise one or more conductive wires, coils, plates, or the like. The control circuitry 34 of the implant device 30 can comprise, for example, one or more chips or dies configured to perform some amount of processing on signals generated and/or transmitted using the device 30. However, due to size, cost, and/or other constraints, the implant device 30 may not include independent processing capability in some embodiments.

The wireless signals generated by the implant device 30 can be received by the local external monitor device or subsystem 42, which can include a reader/antenna-interface circuitry module 43 configured to receive the wireless signal transmissions from the implant device 30, which is disposed at least partially within the patient 44. For example, the module 43 may include transceiver device(s)/circuitry.

The external local monitor 42 can receive the wireless signal transmissions from the implant device 30 and/or provide wireless power to the implant device 30 using an external antenna 48, such as a wand device. The reader/antenna-interface circuitry 43 can include radio-frequency (RF) (or other frequency band) front-end circuitry configured to receive and amplify the signals from the implant device 30, wherein such circuitry can include one or more filters (e.g., band-pass filters), amplifiers (e.g., low-noise amplifiers), analog-to-digital converters (ADC) and/or digital control interface circuitry, phase-locked loop (PLL) circuitry, signal mixers, or the like. The reader/antenna-interface circuitry 43 can further be configured to transmit signals over a network 49 to a remote monitor subsystem or device 46. The RF circuitry of the reader/antenna-interface circuitry 43 can further include one or more of digital-to-analog converter (DAC) circuitry, power amplifiers, low-pass filters, antenna switch modules, antennas or the like for treatment/processing of transmitted signals over the network 49 and/or for receiving signals from the implant device 30. In certain embodiments, the local monitor 42 includes control circuitry 41 for performing processing of the signals received from the implant device 30. The local monitor 42 can be configured to communicate with the network 49 according to a known network protocol, such as Ethernet, Wi-Fi, or the like. In certain embodiments, the local monitor 42 comprises a smartphone, laptop computer, or other mobile computing device, or any other type of computing device.

In certain embodiments, the implant device 30 includes some amount of volatile and/or non-volatile data storage. For example, such data storage can comprise solid-state memory utilizing an array of floating-gate transistors, or the like. The control circuitry 34 may utilize data storage for storing sensed data collected over a period of time, wherein the stored data can be transmitted periodically to the local monitor 42 or another external subsystem. In certain embodiments, the implant device 30 does not include any data storage. The control circuitry 34 may be configured to facilitate wireless transmission of data generated by the sensor transducer(s) 32, or other data associated therewith. The control circuitry 34 may further be configured to receive input from one or more external subsystems, such as from the local monitor 42, or from a remote monitor 46 over, for example, the network 49. For example, the implant device 30 may be configured to receive signals that at least partially control the operation of the implant device 30, such as by activating/deactivating one or more components or sensors, or otherwise affecting operation or performance of the implant device 30.

The one or more components of the implant device 30 can be powered by one or more power sources 35. Due to size, cost and/or electrical complexity concerns, it may be desirable for the power source 35 to be relatively minimalistic in nature. For example, high-power driving voltages and/or currents in the implant device 30 may adversely affect or interfere with operation of the heart or other body part associated with the implant device. In certain embodiments, the power source 35 is at least partially passive in nature, such that power can be received from an external source wirelessly by passive circuitry of the implant device 30, such as through the use of short-range, or near-field wireless power transmission, or other electromagnetic coupling mechanism. For example, the local monitor 42 may serve as an initiator that actively generates an RF field that can provide power to the implant device 30, thereby allowing the power circuitry of the implant device to take a relatively simple form factor. In certain embodiments, the power source 35 can be configured to harvest energy from environmental sources, such as fluid flow, motion, or the like. Additionally or alternatively, the power source 35 can comprise a battery, which can advantageously be configured to provide enough power as needed over the monitoring period (e.g., 3, 5, 10, 20, 30, 40, or 90 days, or other period of time).

In some embodiments, the local monitor device 42 can serve as an intermediate communication device between the implant device 30 and the remote monitor 46. The local monitor device 42 can be a dedicated external unit designed to communicate with the implant device 30. For example, the local monitor device 42 can be a wearable communication device, or other device that can be readily disposed in proximity to the patient 44 and implant device 30. The local monitor device 42 can be configured to continuously, periodically, or sporadically interrogate the implant device 30 in order to extract or request sensor-based information therefrom. In certain embodiments, the local monitor 42 comprises a user interface, wherein a user can utilize the interface to view sensor data, request sensor data, or otherwise interact with the local monitor system 42 and/or implant device 30.

The system 40 can include a secondary local monitor 47, which can be, for example, a desktop computer or other computing device configured to provide a monitoring station or interface for viewing and/or interacting with the monitored cardiac pressure data. In an embodiment, the local monitor 42 can be a wearable device or other device or system configured to be disposed in close physical proximity to the patient and/or implant device 30, wherein the local monitor 42 is primarily designed to receive/transmit signals to and/or from the implant device 30 and provide such signals to the secondary local monitor 47 for viewing, processing, and/or manipulation thereof. The external local monitor system 42 can be configured to receive and/or process certain metadata from or associated with the implant device 30, such as device ID or the like, which can also be provided over the data coupling from the implant device 30.

The remote monitor subsystem 46 can be any type of computing device or collection of computing devices configured to receive, process and/or present monitor data received over the network 49 from the local monitor device 42, secondary local monitor 47, and/or implant device 30. For example, the remote monitor subsystem 46 can advantageously be operated and/or controlled by a healthcare entity, such as a hospital, doctor, or other care entity associated with the patient 44. Although certain embodiments disclosed herein describe communication with the remote monitor subsystem 46 from the implant device indirectly through the local monitor device 42, in certain embodiments, the implant device 30 can comprise a transmitter capable of communicating over the network 49 with the remote monitor subsystem 46 without the necessity of relaying information through the local monitor device 42.

In some embodiments, at least a portion of the transducer 32, control circuitry 34, power source 35 and/or the antenna 38 are at least partially disposed or contained within the sensor housing 36, which may comprise any type of material, and may advantageously be at least partially hermetically sealed. For example, the housing 36 may comprise glass or other rigid material in some embodiments, which may provide mechanical stability and/or protection for the components housed therein. In some embodiments, the housing 36 is at least partially flexible. For example, the housing may comprise polymer or other flexible structure/material, which may advantageously allow for folding, bending, or collapsing of the sensor 30 to allow for transportation thereof through a catheter or other percutaneous introducing means.

Cardiac Shunt Implants

Figure 6:
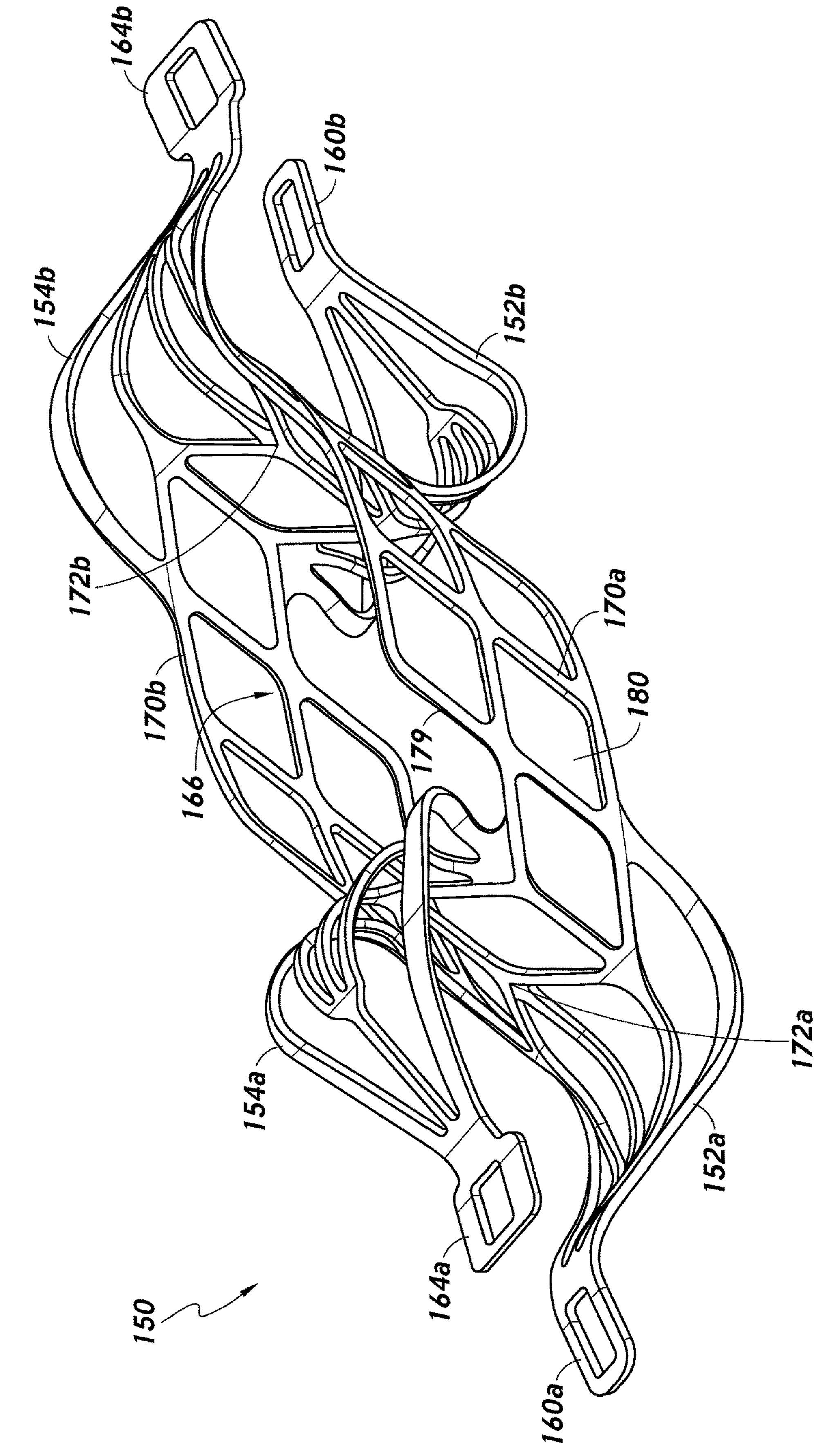
FIG. 6 illustrates an example shunt structure in accordance with one or more embodiments.

FIG. 6 illustrates an example shunt/anchor structure 150 in accordance with one or more embodiments. The shunt structure 150 may represent an embodiment of a cardiac implant (e.g., anchor and/or cardiac implant structure 39 associated with FIG. 4 or 5) that may be integrated with pressure sensor functionality in accordance with certain embodiments disclosed herein. The shunt structure 150 may be an expandable shunt. When expanded, a central flow channel 166 of the shunt 150 may define a generally circular or oval opening. The channel 166 may be configured to hold the sides of a puncture opening in a tissue wall to form a blood flow path between chamber(s) or vessel(s) of the heart that are separated by the tissue wall. For example, the shunt 150 may be configured to be implanted in the wall separating the coronary sinus and the left atrium. The central flow channel 166 may be partly formed by a pair of side walls 170*a*, 170*b* defined by a generally parallel arrangement of thin struts 179 that forms an array of parallelogram-shaped cells or openings 180. In some embodiments, substantially the entire shunt 150 is formed by super-elastic struts that are configured to be compressed and fit into a catheter (not shown) and subsequently expanded back to the relaxed shape as shown in FIG. 6.

Formation of the shunt 150 using a plurality of interconnected struts forming cells therebetween may serve to at least partially increase the flexibility of the shunt, thereby enabling compression thereof and expansion at the implant site. The interconnected struts around the central flow channel 166 advantageously provide a cage having sufficient rigidity and structure to hold the tissue at the puncture in an open position. End walls 172*a*, 172*b* of the central flow channel 166 can serve to connect the side walls 170*a*, 170*b* and extend between distal and proximal flanges, or arms, 152, 154 on each side. The side walls 170*a*, 170*b* and end walls 172*a*, 172*b* together may define a tubular lattice, as shown. The end walls 172*a*, 172*b* can comprise thin struts 179 extending at a slight angle from a central flow axis of the shunt 150.

Although the illustrated shunt 150 comprises struts that define a tubular or circular lattice of open cells forming the central flow channel 166, in some embodiments, the structure that makes up the channel forms a substantially contiguous wall surface through at least a portion of the channel 166. In the illustrated embodiment, the tilt of the shunt structure 150 may facilitate collapse of the shunt into a delivery catheter (not shown), as well as the expansion of the flanges/arm 152, 154 on both sides of a target tissue wall. The central flow channel 166 may remain essentially unchanged between the collapsed and expanded states of the shunt 150, whereas the flanges/arms 152, 154 may transition in and out of alignment with the angled flow channel.

Although certain embodiments of shunts disclosed herein comprise flow channels having substantially circular cross-sections, in some embodiments, shunt structures in accordance with the present disclosure have oval-shaped, rectangular, diamond-shaped, or elliptical flow channel configuration. For example, relatively elongated side walls compared to the illustrated configuration of FIG. 6 may produce a rectangular or oval-shaped flow channel. Such shapes of shunt flow channels may be desirable for larger punctures, while still being configured to collapse down to a relatively small delivery profile.

In some embodiments, each of the distal and proximal flanges/arms 152, 154 is configured to curl outward from the end walls 172*a*, 172*b* and be set to point approximately radially away from the central flow channel 166 in the expanded configuration. The expanded flanges/arms may serve to secure the shunt 150 to a target tissue wall. Additional aspects and features of shunt, implant, and/or anchor structures that may be integrated with sensor devices/functionality of embodiments of the present disclosure are disclosed in U.S. Pat. No. 9,789,294, entitled "Expandable Cardiac Shunt," issued on Oct. 17, 2017, the disclosure of which is hereby expressly incorporated by reference in its entirety. Although certain embodiments are disclosed herein in the context of shunt structures similar to that shown in FIG. 6 and described above, it should be understood that shunt structures or other implant devices integrated with pressure sensor functionality in accordance with embodiments of the present disclosure may have any type, form, structure, configuration, and/or may be used or configured to be used for any purpose, whether for shunting or other purpose or functionality.

Figure 7:
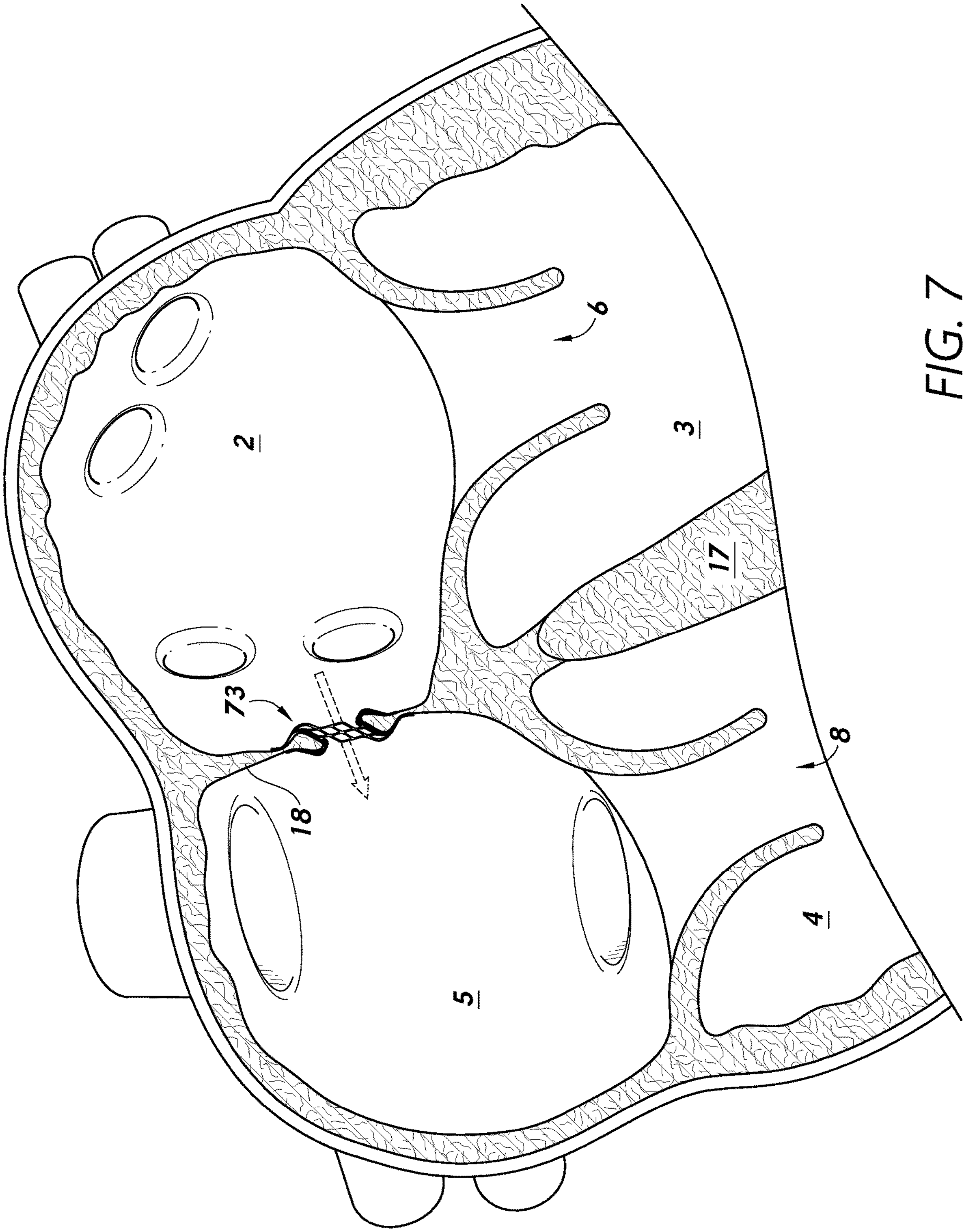
FIG. 7 shows a shunt structure implanted in an atrial septum in accordance with one or more embodiments.

FIG. 7 shows a shunt implant/anchor device/structure 73 implanted in an atrial septum 18 in accordance with one or more embodiments. The particular position in the atrial septum wall 18 may be selected or determined to provide a relatively secure anchor location for the shunt structure 73. Furthermore, the shunt device/structure 73 may be implanted at a position that is desirable in consideration of future re-crossing of the septal wall 18 for future interventions. Implantation of the shunt device/structure 73 in the atrial septum wall 18 may advantageously allow for fluid communication between the left 2 and right 5 atria.

Interatrial shunting using the shunt device/structure 73 may be well-suited for patients that are relatively highly sensitive to atrial pressure increases. For example, as pressure increases in the ventricles and/or atria and is applied against the myocardial cells, the muscles of the heart may generally be prone to contract relatively harder to process the excess blood. Therefore, as the ventricle dilates or stretches, for patients with compromised contractility of the ventricle, such patients may become more sensitive to higher pressures in the ventricle and/or atria because the heart may be unable to adequately respond or react thereto. Furthermore, increases in left atrial pressure can results in dyspnea, and therefore reduction in left atrial pressure to reduce dyspnea and/or reduce incidences of hospital readmission may be desirable through interatrial shunting. For example, when the ventricle experiences dysfunction such that is unable to accommodate build-up in fluid pressure, such fluid may backup into the atria, thereby increasing atrial pressure. With respect to heart failure, minimization of left ventricular end-diastolic pressure may be paramount. Because left ventricular end-diastolic pressure can be related to left atrial pressure, backup of fluid in the atrium can cause backup of fluid in the lungs, thereby causing undesirable and/or dangerous fluid buildup in the lungs. Interatrial shunting, such as using shunt devices in accordance with embodiments of the present disclosure, can divert extra fluid in the left atrium to the right atrium, which may be able to accommodate the additional fluid due to the relatively high compliance in the right atrium.

Figure 8:
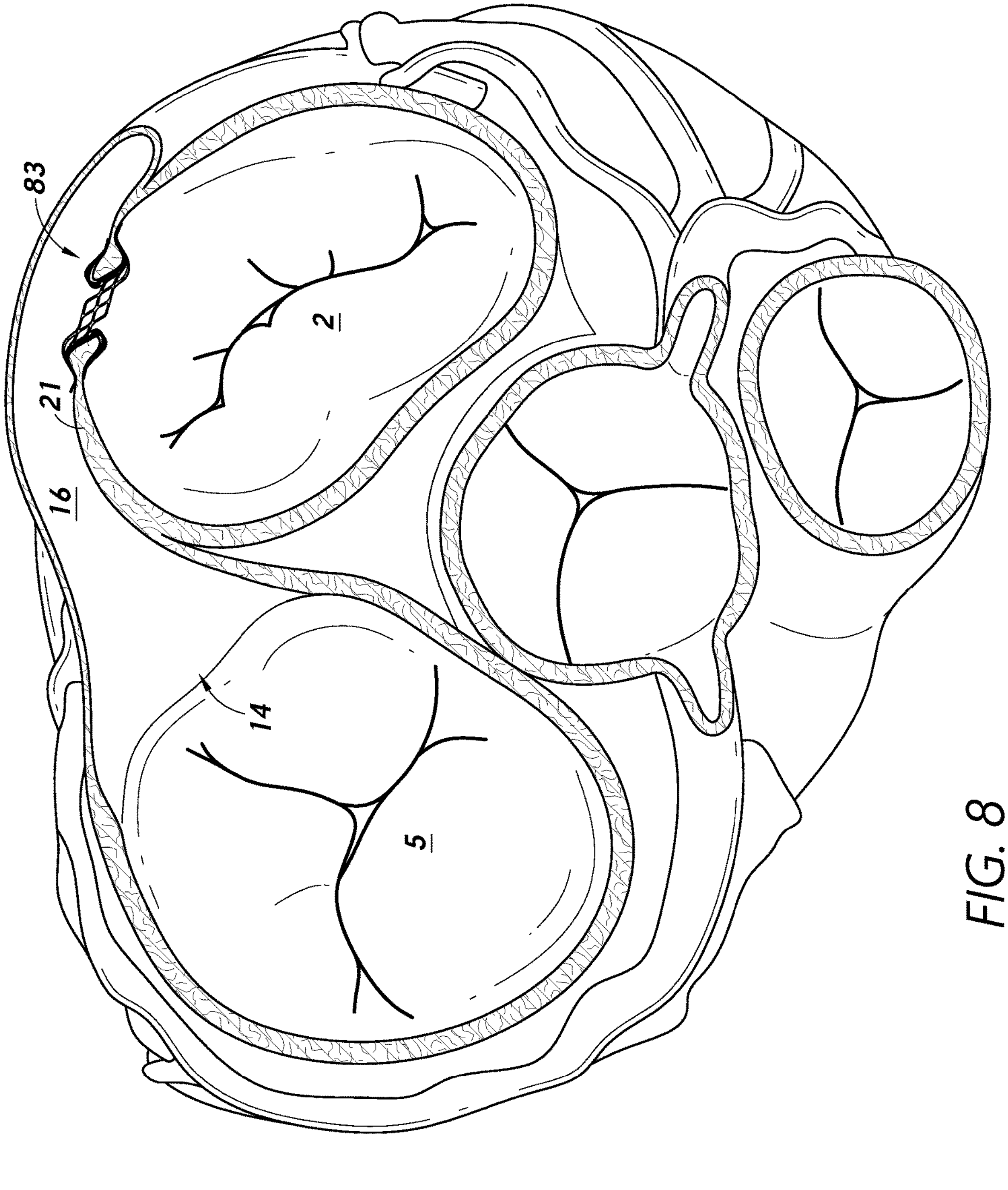
FIG. 8 shows a sensor implant device implanted in a tissue wall between a coronary sinus and a left atrium in accordance with one or more embodiments.

In some implementations, shunt devices/structures in accordance with embodiments of the present disclosure may be implanted in a wall separating the coronary sinus from the left atrium, such that interatrial shunting may be achieved through the coronary sinus. FIG. 8 shows a shunt device/structure 83 implanted in a tissue wall 21 between the coronary sinus 16 and the left atrium 2. FIG. 8, as well as a number of the following figures, shows a section of the heart from a top-down, superior perspective with the posterior aspect oriented at the top of the page.

In some cases, left-to-right shunting through implantation of the shunt device 83 in the wall 21 between the left atrium 2 and the coronary sinus 16 can be preferable to shunting through the atrial septum. For example, shunting through the coronary sinus 16 can provide reduced risk of thrombus and embolism. The coronary sinus is less likely to have thrombus/emboli present for several reasons. First, the blood draining from the coronary vasculature into the right atrium 5 has just passed through capillaries, so it is essentially filtered blood. Second, the ostium 14 of the coronary sinus in the right atrium is often partially covered by a pseudo-valve called the Thebesian Valve (not shown). The Thebesian Valve is not always present, but some studies show it is present in most hearts and can block thrombus or other emboli from entering in the event of a spike in right atrium pressure. Third, the pressure gradient between the coronary sinus and the right atrium into which it drains is generally relatively low, such that thrombus or other emboli in the right atrium is likely to remain there. Fourth, in the event that thrombus/emboli do enter the coronary sinus, there will be a much greater gradient between the right atrium and the coronary vasculature than between the right atrium and the left atrium. Most likely, thrombus/emboli would travel further down the coronary vasculature until right atrium pressure returned to normal and then the emboli would return directly to the right atrium.

Some additional advantages to locating the shunt structure 83 between the left atrium and the coronary sinus is that this anatomy is generally more stable than the interatrial septal tissue. By diverting left atrial blood into the coronary sinus, sinus pressures may increase by a small amount. This would cause blood in the coronary vasculature to travel more slowly through the heart, increasing perfusion and oxygen transfer, which can be more efficient and also can help a dying heart muscle to recover. In addition, by implanting the shunt device/structure 83 in the wall of the coronary sinus 83, damage to the atrial septum 18 may be prevented. Therefore, the atrial septum 18 may be preserved for later transseptal access for alternate therapies. The preservation of transseptal access may be advantageous for various reasons. For example, heart failure patients often have a number of other comorbidities, such as atrial fibrillation and/or mitral regurgitation; certain therapies for treating these conditions require a transseptal access.

It should be noted, that in addition to the various benefits of placing the implant/structure 83 between the coronary sinus 16 and the left atrium 2, certain drawbacks may be considered. For example, by shunting blood from the left atrium 2 to the coronary sinus 16, oxygenated blood from the left atrium 2 may be passed to the right atrium 5 and/or non-oxygenated blood from the right atrium 5 may be passed to the left atrium 2, both of which may be undesirable with respect to proper functioning of the heart.

Sensor-Integrated Implant Devices

As referenced above, shunt and/or other implant devices/structures may be integrated with sensor, antenna/transceiver, and/or other components to facilitate in vivo monitoring of pressure and/or other physiological parameter(s). Sensor devices in accordance with embodiments of the present disclosure may be integrated with cardiac shunt structures/devices or other implant devices using any suitable or desirable attachment or integration mechanism or configuration.

Figures 1, 9:
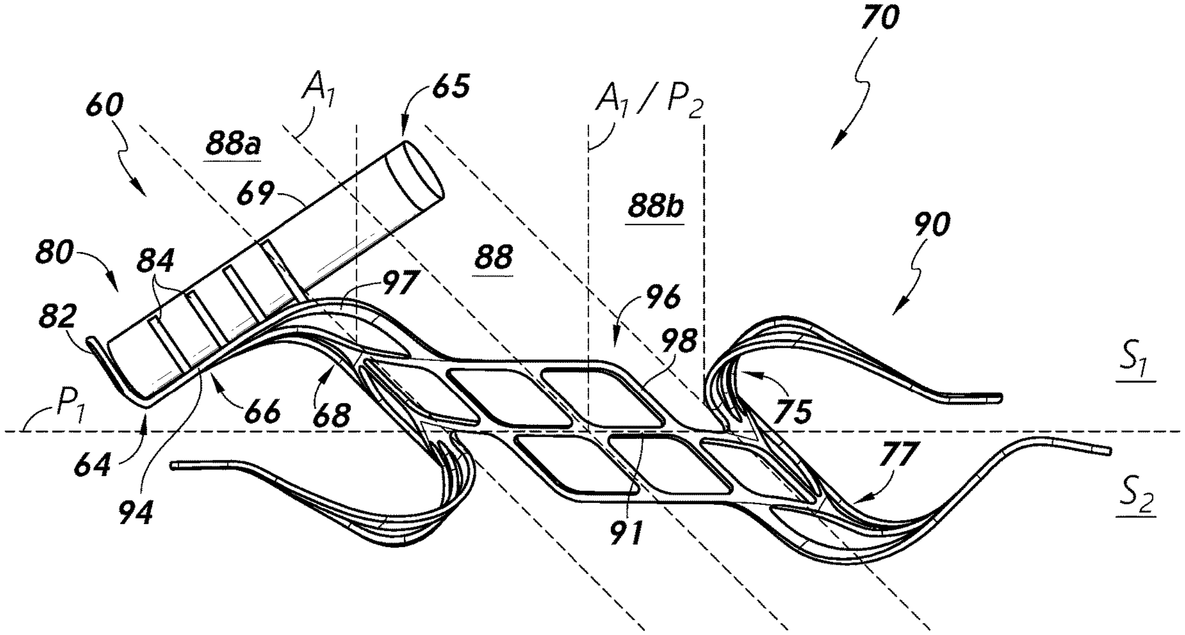
Figures 2, 9:
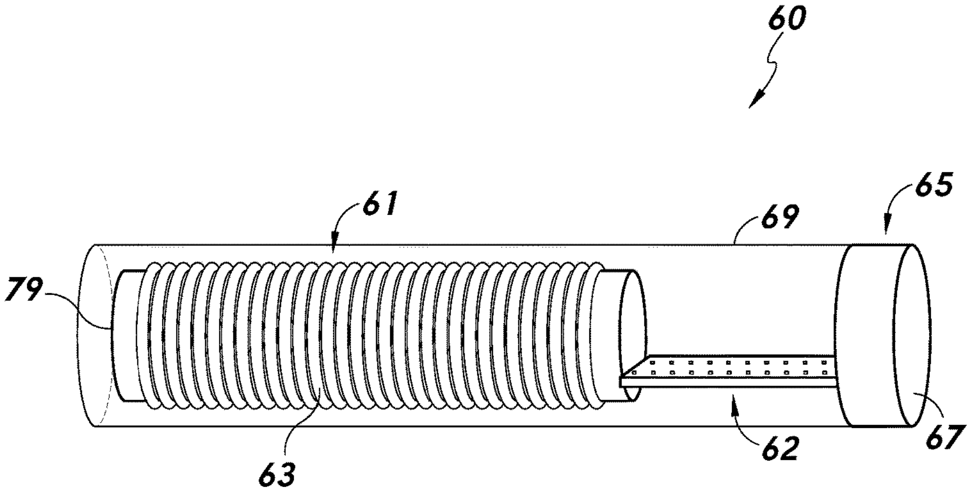

FIG. 9-1 illustrates a side view of a sensor implant device 70 in accordance with one or more embodiments. FIG. 9-2 illustrates an example sensor device/assembly 60 that may be used in sensor implant devices, such as in the sensor implant device 70 shown in FIG. 9-1, in accordance with one or more embodiments of the present disclosure.

In some embodiments, the sensor device/assembly 60 includes a sensor transducer component 65 and an antenna component 61. The sensor transducer component 65 may comprise any type of sensor transducer as described in detail above. In some embodiments, the sensor device 60 may be attached to or integrated with an arm member 94 of the shunt structure 90, as shown. For example, the arm 94 with which the sensor device 60 is associated may be generally associated with a distal or proximal axial portion/end of the shunt structure 90. That is, when the shunt structure 90 is implanted, one or more arms of the shunt structure 90 may be associated with an inlet/distal portion of the shunt structure 90, whereas one or more other anchor arms may be associated with an outlet/proximal portion of the shunt structure 90. Although distal and proximal sides/portions are in some contexts herein, it should be understood that identified distal portions/sides may be outlet or inlet sides of the relevant shunt structure, as with identified proximal portions/sides. Furthermore, the terms "distal" and "proximal" are used for convenience and may or may not refer to relative orientation with respect to a delivery system/device used to implant the relevant sensor implant device and/or shunt structure.

The sensor transducer component 65 includes a sensor element 67, such as a pressure sensor transducer/membrane. Relative to the arm member 94 of the shunt structure 90, the sensor device 60 may be attached/positioned at/on a distal 64, medial 66, or proximal 68 portion or area of the arm/anchor 94, or any portion therebetween. For example, the illustrated embodiment of FIG. 9-1 includes the sensor device 60 disposed primarily on the medial area 66 and distal area 64 of the arm/anchor 94. In some embodiments, readings acquired by the sensor device 60 may be used to guide titration of medication for treatment of a patient in whom the implant device 70 is implanted.

As described herein, the sensor device 60 may be configured to implement wireless data and/or power transmission. The sensor device 60 may include the antenna component 61 for such purpose. The antenna 61, as well as one or more other components of the sensor device 60, may be contained at least partially within a sensor housing 69, which may further have disposed therein certain control circuitry 62 configured to facilitate wireless data and/or power communication functionality. In some embodiments, the antenna component 61 comprises one or more conductive coils 63, which may facilitate inductive powering and/or data transmission. In embodiments comprising conductive coil(s), such coil(s) may be wrapped/disposed at least partially around a magnetic (e.g., ferrite, iron) core 79.

In some embodiments, the arm 94 includes an elongated strut/arm feature to which the sensor device 60 is secured. The sensor device 60 may be secured to the anchor arm 94 using any suitable means or mechanism. For example, securement/attachment means/mechanisms that may be suitable for attaching the sensor device 60 to any of the arms of the shunt structure 90 may be any of the features disclosed in PCT Application No. PCT/US20/56746, Filed on Oct. 22, 2020, and entitled "Sensor Integration in Cardiac Implant Devices," the contents of which are hereby expressly incorporated by reference in their entirety. For example, the shunt structure 90 and/or arm(s) thereof may include one or more sensor-retention fingers, clamps, wraps, bands, belts, clips, pouches, housings, encasements, and/or the like configured to secure the sensor device 60 to an arm, strut, or other structural feature of the shunt structure 90.

The sensor device 60 may be associated with either axial side/end of the shunt structure 90, wherein the different axial sides/ends of the shunt structure 90 are exposed on opposite sides ($S_1$, $S_2$) of a tissue wall when the implant device 70 is implanted in the tissue wall. As described herein, references to axial sides of a shunt structure may refer to opposite sides of a plane $P_1$ axially (and/or diagonally, as in FIG. 9-1) bisecting the shunt structure 90 and/or barrel portion thereof 98. The plane $P_1$ may be orthogonal to an axis of the barrel portion 98 of the shunt structure 90 and/or may be substantially parallel with (e.g., on/within) a tissue wall in which the shunt structure 90 is implanted. That is, when the shunt structure 90 is implanted in a tissue wall (not shown in FIG. 9-1; see FIGS. 15-22), the axis $A_1$ of the barrel 98 may be askew/angled with respect to a line/plane $A_2$ that is normal to the tissue wall surface; it should be understood that description herein of shunt axes may be understood to refer to an axis/line that is substantially normal to a tissue-engagement plane (e.g., plane $P_1$ shown in FIG. 9-1), even in embodiments/cases in which the shunt barrel has a true axis $A_1$ that is angled with respect to the tissue-engagement plane $P_1$, as in FIG. 9-1. Description herein of axial sides of an implant structure can be understood to refer to different sides of the tissue-engagement plane $P_1$. The plane $P_1$ may be aligned (e.g., within 5° or 10° of exact alignment) with at least some of the struts 91 (e.g., circumferentially-arranged struts) of the barrel/conduit portion 98 of the shunt structure 90.

Furthermore, description herein of sensor device being disposed on different radial sides of a shunt structure may refer to diametrically opposite sides of a diametrical plane $P_2$, as shown in FIG. 9-1. For example, where a shunt structure includes arms on a given axial side of the shunt structure that emanate from substantially opposite circumferential portions of a barrel/conduit portion of the shunt structure and/or project in substantially opposite radial directions with respect to an axis of the barrel/conduit of the shunt structure, such arms may be considered to be on different and/or opposite radial sides of the shunt structure.

The sensor device 60 may advantageously be biocompatible. For example, the housing 69 may advantageously be biocompatible, such as a housing comprising glass or other biocompatible material. However, at least a portion of the sensor transducer element/membrane 67, such as a diaphragm or other component, may be exposed to the external environment in some embodiments in order to allow for pressure readings, or other parameter sensing, to be implemented. The housing 69 may comprise an at least partially rigid cylindrical or tube-like form, such as a glass cylinder form. In some embodiments, the sensor transducer component 65/67 is approximately 3 mm or less in diameter. The antenna 61 may be approximately 20 mm or less in length.

The sensor device 60 may be configured to communicate with an external system when implanted in a heart or other area of a patient's body. For example, the antenna 61 may receive power wirelessly from the external system and/or communicate sensed data or waveforms to and/or from the external system. The sensor device 60 may be attached to, or integrated with, the shunt structure 90 in any suitable or desirable way. For example, in some implementations, the sensor device 60 may be attached or integrated with the shunt structure 90 using mechanical attachment means. In some embodiments, the sensor device 60 may be contained in a pouch or other receptacle that is attached to the shunt structure 90.

The sensor element 67 may comprise a pressure transducer. For example, the pressure transducer may be a microelectromechanical system (MEMS) transducer comprising a semiconductor diaphragm component. In some embodiments, the transducer may include an at least partially flexible or compressible diaphragm component, which may be made from silicone or other flexible material. The diaphragm component may be configured to be flexed or compressed in response to changes in environmental pressure. The control circuitry 62 may be configured to process signals generated in response to said flexing/compression to provide pressure readings. In some embodiments, the diaphragm component is associated with a biocompatible layer on the outside surface thereof, such as silicon nitride (e.g., doped silicon nitride) or the like. The diaphragm component and/or other components of the pressure transducer 67 may advantageously be fused or otherwise sealed to/with the housing 69 of the sensor device 60 in order to provide hermetic sealing of at least some of the sensor components.

The control circuitry 62 may comprise one or more electronic application-specific integrated circuit (ASIC) chips or die, which may be programmed and/or customized or configured to perform monitoring functionality as described herein and/or facilitate transmission of sensor signals wirelessly. The antenna 61 may comprise a ferrite core 79 wrapped with conductive material in the form of a plurality of coils 63 (e.g., wire coil). In some embodiments, the coils comprise copper or other metal. The antenna 61 may advantageously be configured with coil geometry that does not result in substantial displacement or heating in the presence of magnetic resonance imaging. In some implementations, the sensor implant device 70 may be delivered to a target implant site using a delivery catheter (not shown), wherein the delivery catheter includes a cavity or channel configured to accommodate the advancement of the sensor device 60 therethrough.

The sensor implant device 70 includes a shunt structure 90, which may include a central barrel structure 98, which may comprise one or more struts 91 or other structural features forming an oval, circular, oblong, and/or elliptical cylindrical fluid conduit. It should be understood that references herein to fluid conduits, cylinders, and/or barrel structures of and/or formed by a shunt structure may have any axial cross-sectional shape.

The shunt structure 90 may generally have first 75 and second 77 axial ends of the barrel/conduit structure 98, wherein certain tissue anchor features may emanate therefrom, at least in part, as shown in FIG. 9-1. For example, as described in detail herein, one or more anchor arms 97 may emanate from the barrel 98, wherein, in a deployment configuration as shown in FIG. 9-1, the arm(s) extend radially outward from the fluid conduit 98. Conversely, in a delivery configuration, as described in greater detail below, the arm(s) 97 may extend generally axially with respect to the barrel/conduit axis $A_1$.

In some embodiments, one or more of the arms 97 may include certain sensor-retention features configured to hold, secure, or otherwise retain the sensor device 60, as shown. For example, the sensor device 60 may comprise a generally cylindrical housing or form 69, which may house one or more internal sensor components and may advantageously be hermetically sealed at least in part. In some embodiments, the housing 69 comprises glass or other at least partially rigid material.

The sensor retention feature(s) 80 associated with the anchor arm 94 may have any suitable or desirable form. For example, the sensor-retention feature(s) 80 may comprise one or more sensor retention fingers 84 or other bands, straps, wraps, coils, wires, adhesives, clamps, clips, apertures, engagement projections or forms, locks, or other retention features. In some embodiments, the anchor arm 94 includes a distal stopper feature 82, such as a tab or similar form/structure, configured to limit distal movement of the sensor device 60 beyond the distal end 64 of the shunt arm 94. For example, the stopper feature 82 may be a tab that is folded to cover the radial profile of the sensor device 60 in a manner as to restrict axial movement in at least one direction of the sensor device 60. In some embodiments, the sensor device 60 is integrated with the arm 94, such that separate retention features are not necessary to secure the sensor device 60 to the shunt structure 90. For example, the anchor arm 94 may be integral with the housing 69 of the sensor device 60. In some embodiments, the barrel/conduit form/body 98 that defines the shunt orifice may be covered internally and/or externally, at least in part, with fabric or other covering, which may provide sealing for the device.

The sensor device 60 may advantageously be disposed, position, secured, oriented, and/or otherwise situated in a configuration in which the sensor transducer component 65 thereof is disposed within a channel area 88 of the shunt structure 90. The term "channel area" is used herein according to its broad and ordinary meaning and may refer to a three-dimensional space defined by a radial boundary of a fluid conduit and extending from the fluid conduit. For example, with respect to a given fluid conduit structure, such as the fluid conduit/barrel structure 98 of the shunt structure 90, a channel area associated therewith may be considered to be defined according to any of the illustrated and described channel areas 88 shown in FIGS. 10-1 through 10-3.

Figures 1, 10:
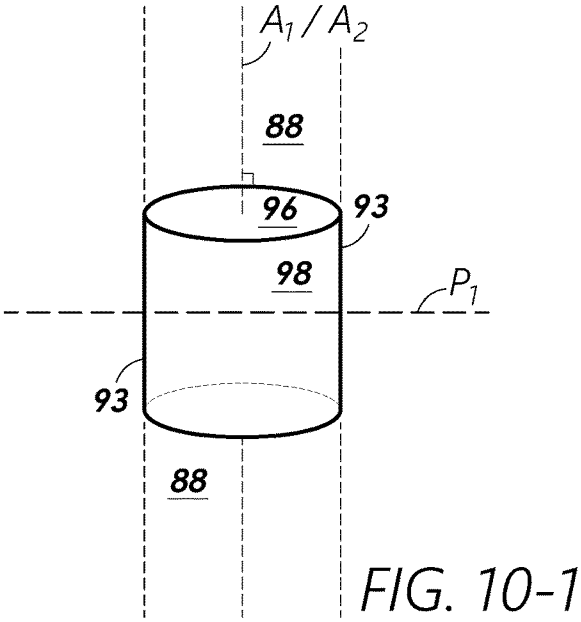
Figures 2, 10:
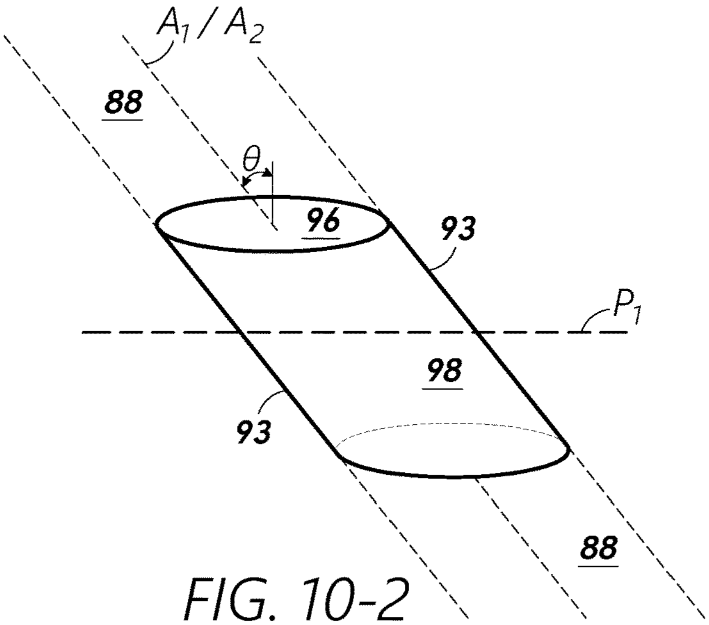
Figures 3, 10:
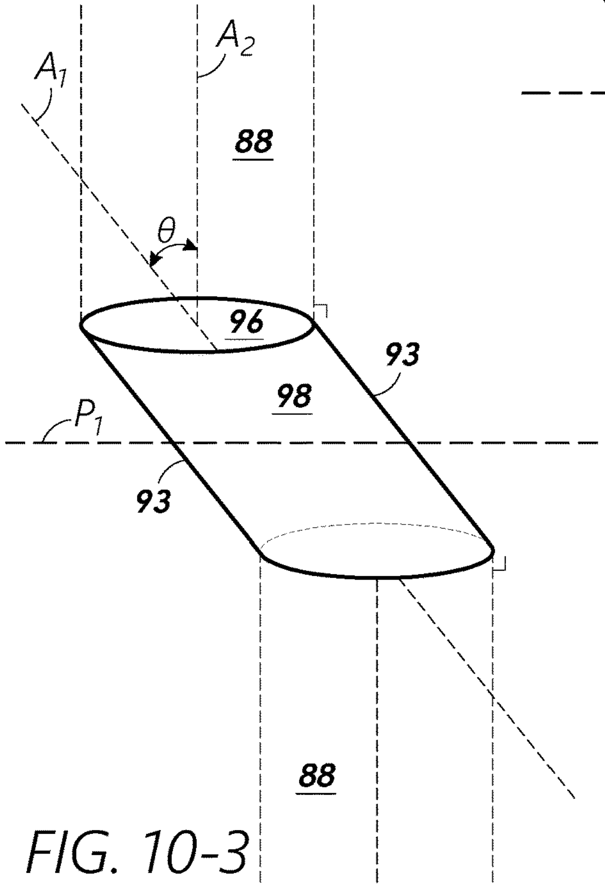

FIG. 10-1 shows an example fluid conduit 98 formed by one or more outer walls 93, wherein the fluid conduit 98 is associated with a tissue plane $P_1$. For example, as described above, the tissue plane $P_1$ may generally represent a plane that lies in or parallel to a tissue wall in which the fluid conduit 98 is configured to be implanted/disposed. For example, the fluid conduit 98 may represent a conduit structure of a shunt implant device as described herein. In the particular embodiment of FIG. 10-1, the fluid conduit 98 has an axis $A_1$ that is generally orthogonal, perpendicular, and/or normal to the tissue plane $P_1$. In such an embodiment/configuration, the channel area 88 associated with the fluid conduit 98 can be considered to be a three-dimensional projection/extension of the area of the fluid conduit around the axis $A_1$, and bounded by the wall(s) 93, in one or more directions, as shown. Therefore, the channel area 88 may be a three-dimensional area enclosed by a cylinder having the same axial cross-sectional area as the fluid conduit 98 and being disposed about the axis $A_1$ of the fluid conduit 98. Therefore, a sensor transducer disposed within the channel area 88 of the fluid conduit 98 shown in FIG. 10-1 may be considered to be disposed in an area defined by the radial boundary of the fluid conduit 98 around the axis $A_1$ of the fluid conduit 98. Furthermore, the sensor transducer may be disposed in an area of the channel area 88 that is axially outside of the fluid conduit structure 98, as with the illustrated sensor implant device 70 shown in FIG. 9-1, wherein the sensor transducer 65 is disposed in the channel area 88 axially outside of the shunt barrel structure 98.

FIG. 10-2 shows another example fluid conduit 98 formed by one or more outer walls 93, wherein the fluid conduit 98 is associated with a tissue plane $P_1$, which may be defined/represented in a manner as described in detail above. The fluid conduit 98 of the embodiment of FIG. 10-2 may be configured to be implanted in a tissue wall (e.g., tissue wall coplanar with the tissue plane $P_1$), wherein an axis $A_1$ of the fluid conduit 98 is angled with respect to the tissue plane $P_1$ (i.e., the axis $A_1$ of the conduit 98 is not perpendicular, orthogonal, or normal to the tissue plane $P_1$). That is, the fluid conduit 98 may be an oblique cylinder, as shown. Therefore, in some embodiments, with respect to an oblique/angled fluid conduit 98 as shown in FIG. 10-2, a channel area 88 associated therewith may be considered a three-dimensional area defined by the radial boundary of the fluid conduit 98 about the axis $A_1$ of the fluid conduit extending in one or more directions axially away from the fluid conduit 98, such that the boundary of the channel area 88 is defined by a cylinder that has an axis that is angled with respect to the tissue plane $P_1$, as shown. For example, with respect to the embodiment shown in FIG. 9-1, where the channel area 88 of the fluid conduit 98 of the shunt structure 90 is defined according to the scheme shown in FIG. 10-2, the sensor transducer 65 may be considered to be within the channel area 88 of the fluid conduit 98 in that it is within the angled channel area 88*a* that is coaxial with the oblique/angled conduit/barrel 98.

FIG. 10-3 shows another example fluid conduit 98 formed by one or more outer walls 93, wherein the fluid conduit 98 is associated with a tissue plane $P_1$, which may be defined/represented in a manner as described in detail above. The fluid conduit 98 of the embodiment of FIG. 10-3 may be configured to be implanted in a tissue wall (e.g., tissue wall coplanar with the tissue plane $P_1$) wherein an axis $A_1$ of the conduit 98 is angled with respect to the tissue plane $P_1$ (i.e., the axis $A_1$ of the conduit 98 is not perpendicular, orthogonal, or normal to the tissue plane $P_1$). However, it may be desirable to identify the channel area 88 associated with the fluid conduit 98 as being a channel area having an axis $A_2$ (with respect to FIGS. 10-1, 10-2, and 10-3, $A_1$ represents the axis of the respective fluid conduit, whereas $A_2$ represents the axis (or axes) of the channel area 88 of the fluid conduit; in some cases $A_1$ and $A_2$ may be the same) that is parallel, orthogonal, and/or normal to the plane $P_1$, as shown. Therefore, the channel area 88 of FIG. 10-3 may not be coaxial with the conduit 98, but rather may be defined on one end by the radial boundary of the opening 96 of the conduit 98, wherein the channel area 88 extends therefrom in an orientation/direction that is perpendicular, orthogonal, and/or normal to the plane $P_1$, as shown in FIG. 10-3. For example, with respect to the embodiment shown in FIG. 9-1, where the channel area 88 of the fluid conduit 98 of the shunt structure 90 is defined according to the scheme shown in FIG. 10-3, the sensor transducer 65 may be considered to be within the channel area 88 of the fluid conduit in that it is within the orthogonal/normal channel area 88*b* that is defined by the radial boundary of the opening 96 of the conduit/barrel structure 98 that extends/projects therefrom in an orthogonal/normal orientation/direction that is not coaxial with the oblique/angled conduit structure 98 of the shunt structure 90.

Figure 11:
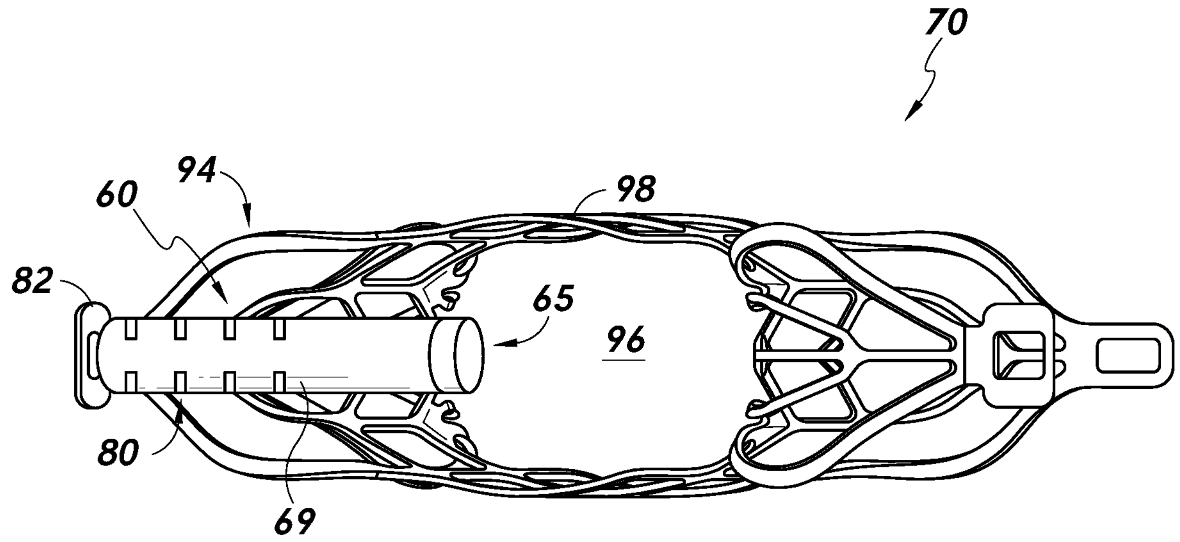
FIGS. 11 and 12 illustrate axial views an embodiment of a shunt-type sensor implant device in accordance with one or more embodiments.

FIG. 11 illustrates an axial view of the implant device 70 of FIG. 9-1 in accordance with one or more embodiments of the present disclosure. Specifically, FIG. 11 shows an axial view that corresponds to an axial side of the implant device 70 associated with the sensor device 60. That is, the sensor component 65 is attached to, integrated with, or otherwise associated with the arm 94, the side of which is shown facing out of the page in FIG. 11. The side shown facing out of the page in FIG. 11 may be a distal or proximal side.

The sensor device 60 can be mechanically attached or fastened to a portion of the arm 94 by any suitable or desirable attachment means, including adhesive attachment or mechanical engagement. For example, the arm 94 may comprise or be associated with one or more retention features, which may comprise one or more clamps, straps, ties, sutures, collars, clips, tabs, or the like. Such retention features may circumferentially encase or retain the sensor device 60, or a portion thereof. In some embodiments, the sensor device 60 may be attached to the arm 94 through the application of mechanical force, either through sliding the sensor 60 through certain retention features or through clipping, locking, or otherwise engaging the sensor 60 with the arm 94 by pressing or applying other mechanical force thereto. In some embodiments, the shunt structure 90 may comprise one or more tabs that may be configured to pop-up or extend on one or more sides of the sensor device 60 for mechanical fastening. Such tabs may comprise memory metal (e.g., Nitinol) or other at least partially rigid material. In some embodiments, the sensor device 60 is pre-attached to the arm 94 and/or integrated therewith prior to implantation. In some embodiments, the sensor 60 may be built or manufactured into the shunt structure 90 to form a unitary structure. For example, in some embodiments, the sensor 60 may be attached to or integrated with the arm member 94 of the shunt structure 90.

Figure 12:
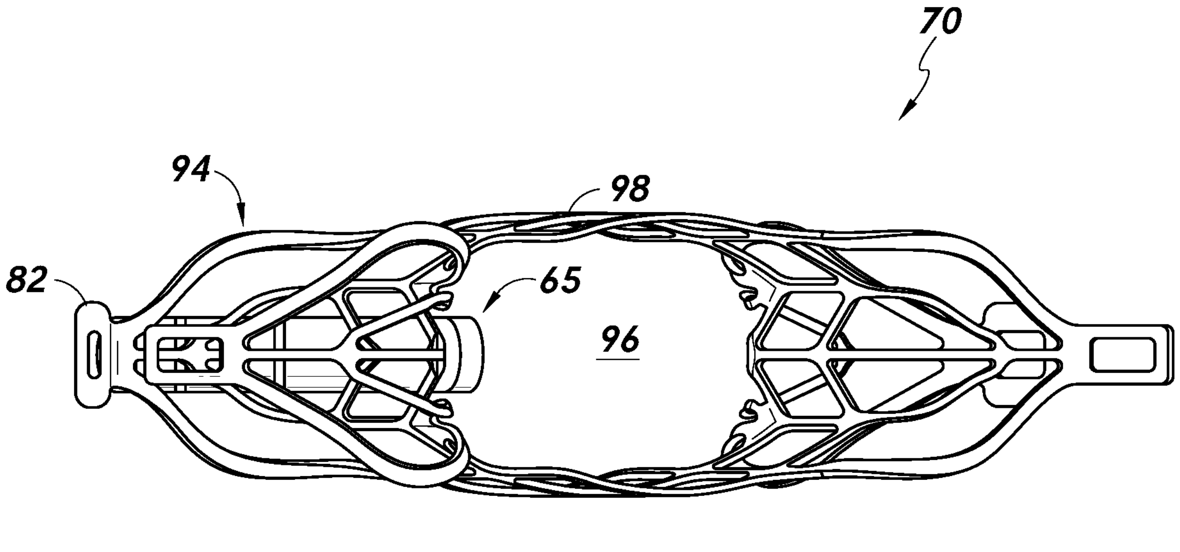

FIG. 12 illustrates another axial view of the implant device 70 of FIG. 9-1 in accordance with one or more embodiments of the present disclosure. Specifically, FIG. 11 shows an axial view that corresponds to an axial side of the implant device 70 that is opposite the sensor device 60. The side shown facing out of the page in FIG. 12 may be a distal or proximal side.

Figure 13:
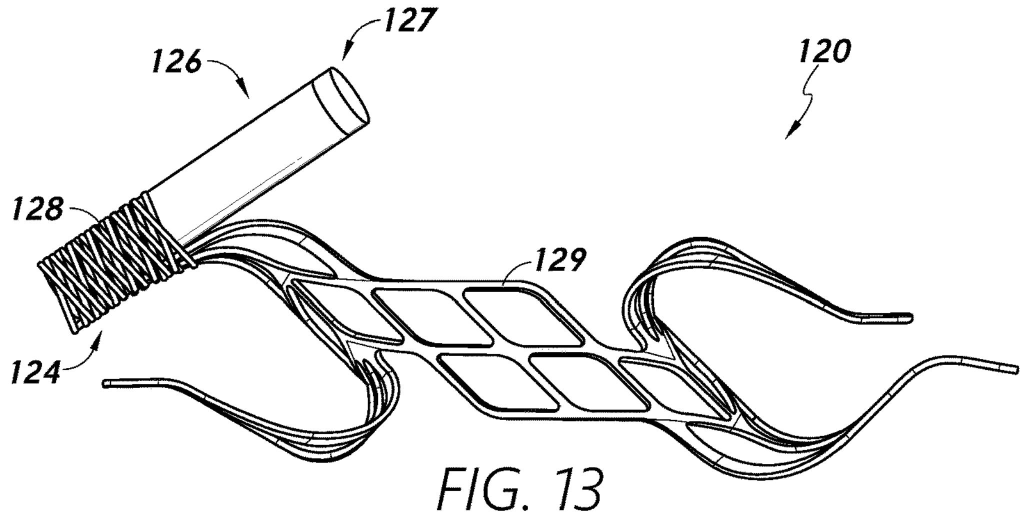
FIG. 13 shows a sensor implant device having a suture-wrapped sensor device associated therewith in accordance with one or more embodiments.

FIG. 13 shows a sensor implant device 120 having a suture-wrapped sensor device 126 associated therewith in accordance with one or more embodiments. The device 126 includes one or more wraps of suture 128 (e.g., PET stitching, or cloth strip(s) or the like) configured to at least partially secure the sensor device 126 to the anchor arm 124. In some embodiments, the wrap 128 is wrapped in strands circumferentially and/or axially on the sensor cylinder and around the anchor arm 124.

The suture wrap 128 can may be wrapped around the cylinder/sensor 126 in a circumferential fashion traversing at least a portion of the length of the sensor 126. In some embodiments, the suture wrap 128 has a sheet-like cover/wrap pulled or applied over the sensor 126 and/or the anchor arm 124. For example, sutures or other type of line or stitching may be wrapped around the cover/wrap to secure the cover/wrap to the sensor 126 and the arm 124. The suture(s)/line 128 may comprise ePTFE, PET, or the like. It may be desirable to protect suture features from tissue in-growth using an appropriate coating, covering, or similar. As with other embodiments of the present disclosure, the suture wrap 128 may be configured to hold the sensor device 126 at an orientation in which the sensor component 127 thereof is disposed in a channel area of the barrel 129 of the implant device 120, as shown (i.e., radially-inward with respect to the fluid conduit formed by the barrel 129).

Figure 14:
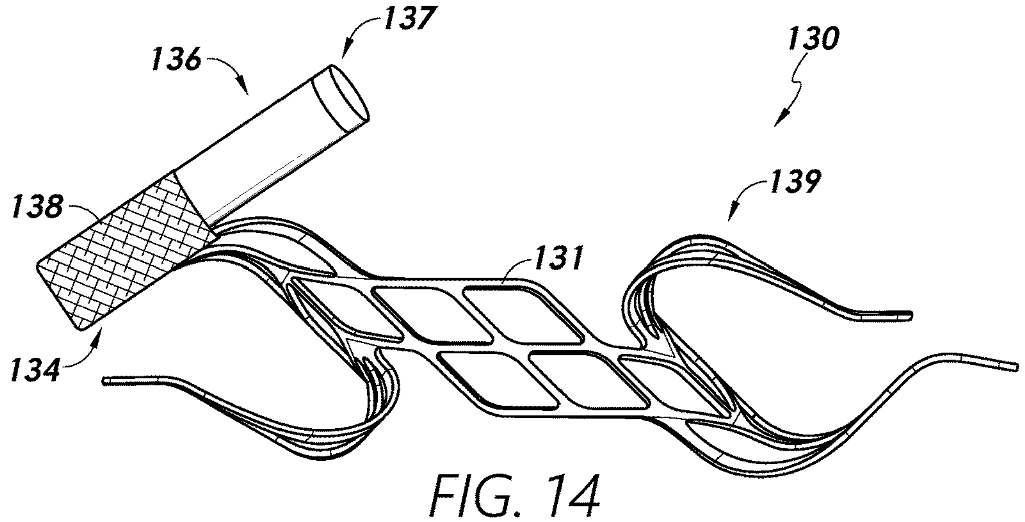
FIG. 14 shows a sensor implant device having a sensor-retention pouch in accordance with one or more embodiments.

FIG. 14 shows a sensor implant device 130 having a sensor-retention pouch 138 in accordance with one or more embodiments. The pouch 130 may comprise a membrane sock- or wrap-type retention means or feature configured to at least partially secure the sensor implant device 130 to the sensor-support strut/arm. The membrane pouch/wrap can comprise polytetrafluoroethylene (PTFE) and/or polyurethane (PU) (e.g., electrospun or rotary-jet-spun) membrane. The pouch or sock 138 can be attached to or otherwise associated with an anchor arm 134 or another portion of the shunt structure. For example, the pouch 138 may be a suture-based or cloth-based (e.g., fibrous and/or polymer cloth) pouch, wrapping, or other retention material and/or form.

The pouch 138 can comprise any suitable or desirable material, including polytetrafluoroethylene (PTFE), expanded polytetrafluoroethylene (ePTFE), polyurethane (PU), or the like and/or combinations of similar materials. Such material may be electrospun onto the sensor 136 in some implementations, or may be applied using rotary jet spinning.

In some embodiments, the sensor 136 is configured to be slidingly disposed within the pouch 138, wherein tension and/or compression of the pouch 138 serves to retain the sensor 136 in a fixed position within the pouch 138. Although a pouch/wrap is illustrated in FIG. 14 that envelops at least a portion of the sensor 136 in a sock-/tube-like manner, in some embodiments, the pouch 138 comprises a band or other non-enveloping retention means. In some embodiments, the sensor 136 may be sutured or otherwise attached or fixed to the pouch 138. Furthermore, the pouch 138 may be sutured or otherwise fixed or attached to the arm member 134 of the shunt structure 139. The pouch 138 may advantageously be open on one or both axial ends thereof to allow for fluid contact with the sensor element/transducer 137 associated with the sensor 136. That is, the sensor 136 may be exposed through an open portion on a distal or proximal end of the arm 134 and/or pouch 138.

In some embodiments, the pouch 138 comprises cloth. In some embodiments, the pouch 138 comprises polymer membrane that has certain heat and voltage characteristics with respect to application process(es) thereof that are such as to not result in undesirable effects/damage with respect to the sensor 137. Wraps, socks, sleeves, membranes, coatings, or similar types of features described herein in connection with the various disclosed embodiments may be applied to sensor-retention structures and/or sensors in any suitable or desirable manner. For example, such materials may be applied using electrospinning process(es) in some implementations. Certain methods, devices, and systems relating to electrospinning concepts that may be applicable to embodiments of the present disclosure are disclosed in U.S. Publication No. 2017/0325976, the disclosure of which is hereby incorporated by reference in its entirety. Electrospinning PTFE is described in U.S. Patent Publication No. 2010/0193999, which is incorporated herein by reference. Other processes that may be implemented to apply wrap, sock, sleeve, membrane, or similar features can include rotary jet spinning. Certain methods, devices, and systems relating to rotary jet spinning concepts that may be applicable to embodiments of the present disclosure are disclosed in U.S. Pat. No. 9,410,267, the disclosure of which is hereby incorporated by reference herein in its entirety. As with other embodiments of the present disclosure, the pouch 138 may be configured to hold the sensor device 136 at an orientation in which the sensor component 127 thereof is disposed in a channel area of the barrel 131 of the implant device 130, as shown (i.e., radially-inward with respect to the fluid conduit formed by the barrel 131).

Figure 15:
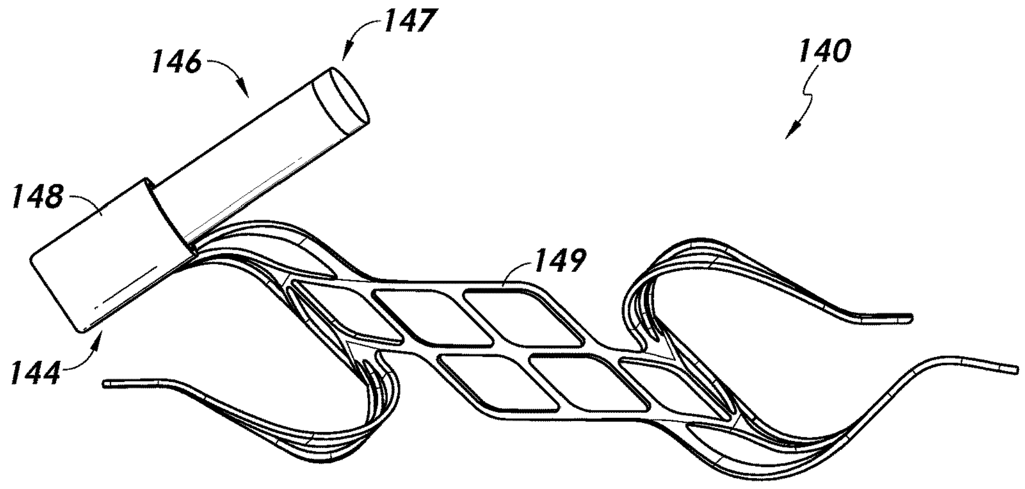
FIG. 15 shows a sensor implant device having a sensor-retention cup in accordance with one or more embodiments.

FIG. 15 shows a sensor implant device 140 having a sensor-retention cup 148 in accordance with one or more embodiments. The cup 148 may comprise an over-mold support form. A sensor 146 is nested at least partially within the cup form 148. The cup 148 may be rigid or flexible. In some embodiments, the cup 148 is bonded to the sensor 146 and/or anchor arm 144 through heat setting or other process. The sensor 146 may be inserted into the cup form 148, or the cup 148 may be applied over the sensor 146 and the anchor arm 144 after placement of the sensor 146 on the anchor arm 144. A polymer wrap may be applied over the cup 148 and sensor 146 to further secure the sensor 146 within the cup 148. As with other embodiments of the present disclosure, the cup 148 may be configured to hold the sensor device 146 at an orientation in which the sensor component 147 thereof is disposed in a channel area of the barrel 149 of the implant device 140, as shown (i.e., radially-inward with respect to the fluid conduit formed by the barrel 149).

FIGS. 16-1, 16-2, 16-3, and 16-4 a sensor implant device 70 implanted in a coronary sinus tissue wall 21 in various positions in accordance with one or more embodiments. The coronary sinus 16 is generally contiguous around the left atrium 2, and therefore there are a variety of possible acceptable placements for the implant device 70. The target site selected for placement of the implant device 70 may be made in an area where the tissue of the particular patient is less thick or less dense, as determined beforehand by non-invasive diagnostic means, such as a CT scan or radiographic technique, such as fluoroscopy or intravascular coronary echo (IVUS).

As with other embodiments, the sensor implant device 70 includes a sensor device 60 including a sensor transducer component 65 and certain connectivity component(s) (e.g., an antenna component and/or other control circuitry). In each of the implementations shown in FIGS. 16-1, 16-2, 16-3, and 16-4, the sensor device 60 is disposed, attached, and/or otherwise secured to or associated with the implant structure 90 (e.g., shunt structure) of the sensor implant device 70 in a manner such that the sensor transducer 65 is disposed within or near a channel area associated with the barrel/conduit portion 98 of the shunt structure 90. For example, the implant device 70 may be configured such that the sensor transducer component 65 is at least partially exposed on the atrial side of the tissue wall 21, as shown.

Figures 1, 16:
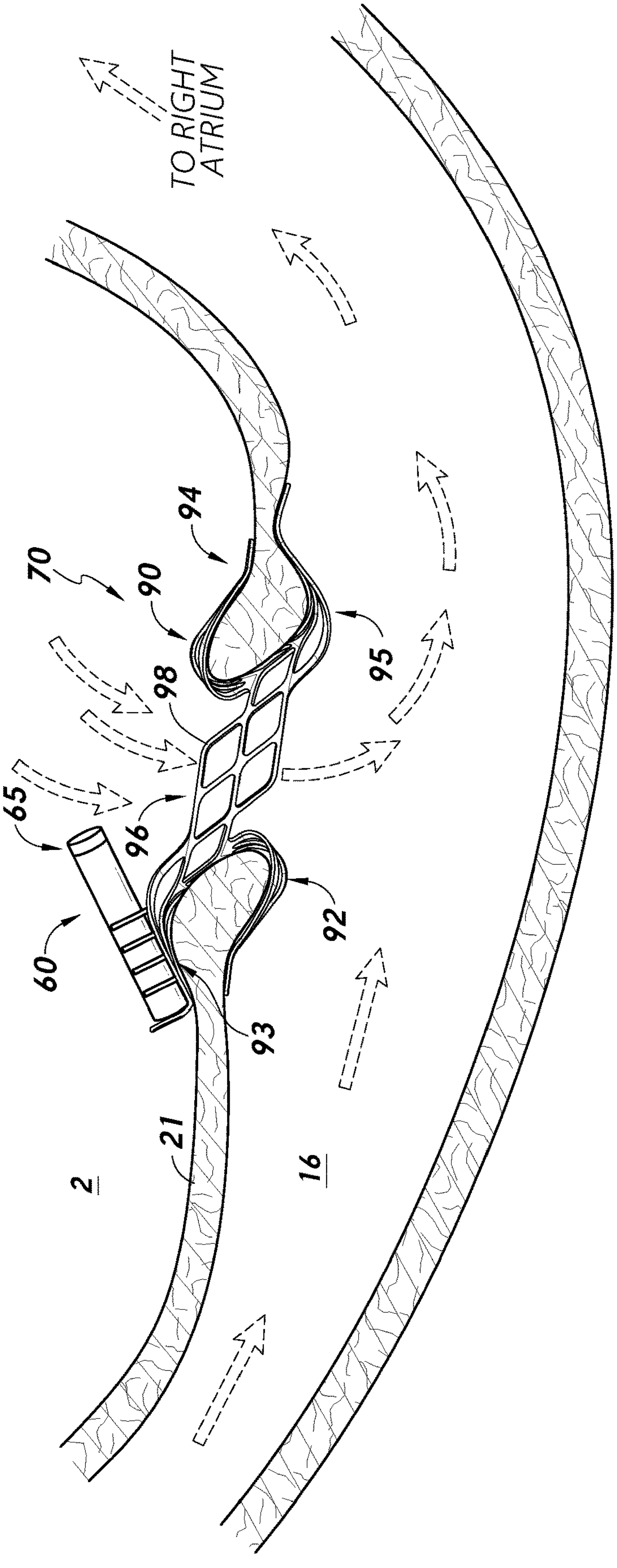
Figures 2, 16:
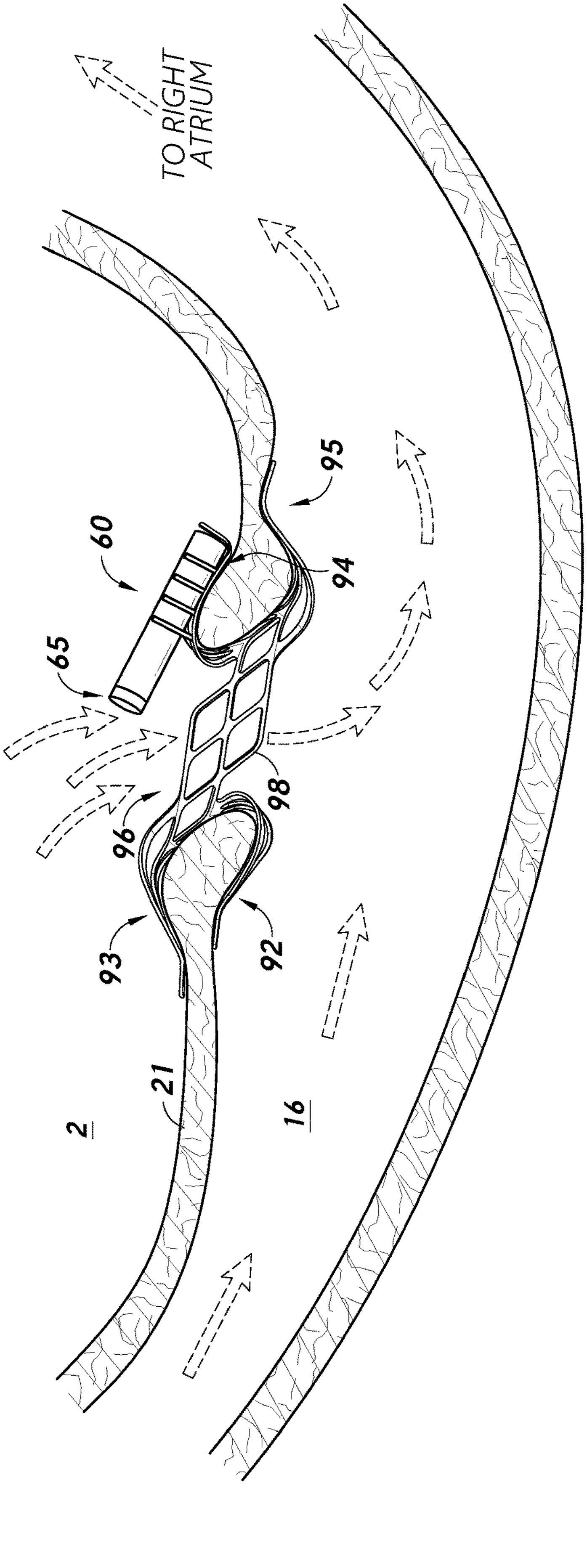
Figures 3, 16:
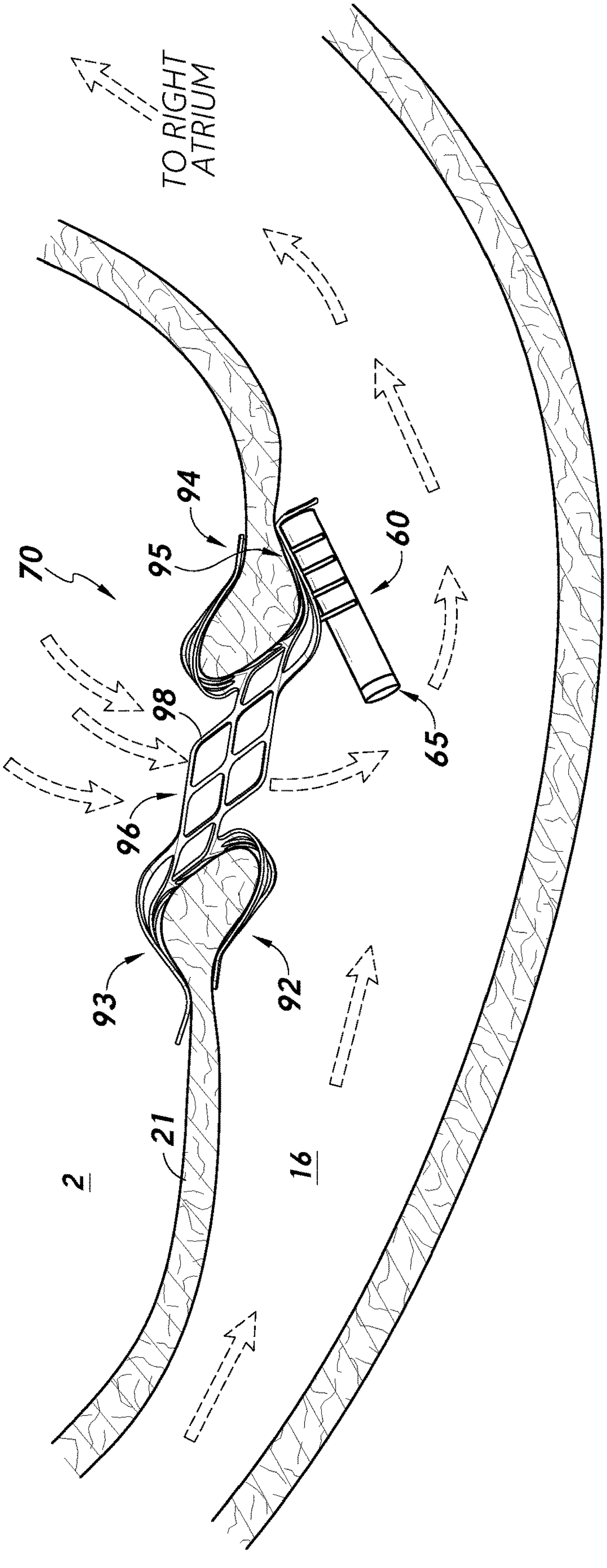
Figures 4, 16:
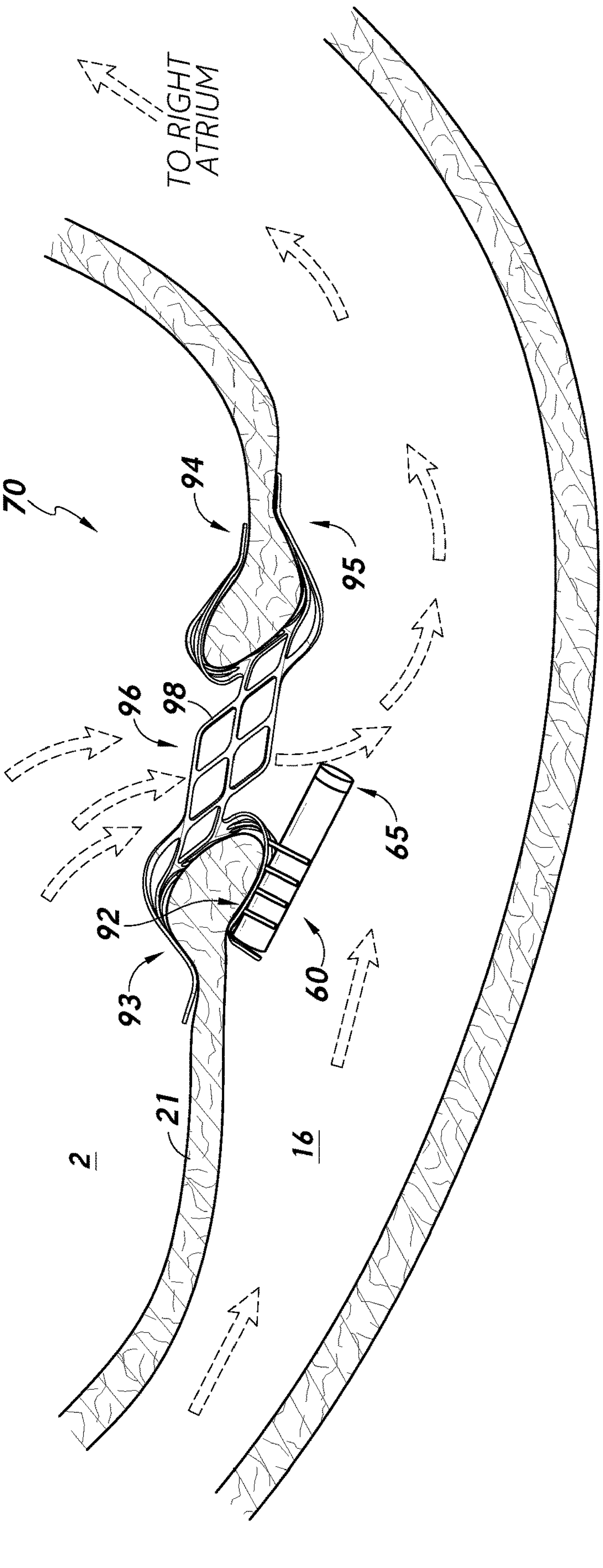

With respect to the particular implementation of FIG. 16-1, the sensor device 60 is associated with an arm 93 that is positioned on the atrial side of the tissue wall 21 and on a side of the shunt structure 90 that is distally positioned with respect to the right atrium. That is, the sensor device 60 is secured to an anchor arm 93 that is positioned generally away from the right atrium (e.g., in the generally narrower area of the coronary sinus 16). With the sensor transducer component 65 disposed in the channel area of the shunt conduit 98, the sensor transducer 65 may advantageously be disposed in an area of flow that is relatively high, thereby allowing for sensor readings to be generated indicating characteristics of the flow through the conduit 98 of the shunt structure 90. For example, the particular placement as shown in FIG. 16-1 with the sensor transducer 65 facing radially inward with respect to the axis of the conduit 98 may provide sensor readings that are more indicative of shunt flow characteristics compared to embodiments in which the sensor transducer is not disposed within the channel area of the conduit and/or is oriented/facing radially away from the conduit 98.

With respect to the particular implementation of FIG. 16-2, the sensor device 60 is associated with an arm 94 that is positioned on the atrial side of the tissue wall 21 and on a side of the shunt structure 90 that is proximally positioned with respect to the right atrium. That is, the sensor device 60 is secured to an anchor arm 94 that is positioned generally toward the right atrium (e.g., in the generally wider area of the coronary sinus 16). With the sensor transducer component 65 disposed in the channel area of the shunt conduit 98, the sensor transducer 65 may advantageously be disposed in an area of flow that is relatively high, thereby allowing for sensor readings to be generated indicating characteristics of the flow through the conduit 98 of the shunt structure 90. For example, the particular placement as shown in FIG. 16-2 with the sensor transducer 65 facing radially inward with respect to the axis of the conduit 98 may provide sensor readings that are more indicative of shunt flow characteristics compared to embodiments in which the sensor transducer is not disposed within the channel area of the conduit and/or is oriented/facing radially away from the conduit 98.

With respect to the particular implementation of FIG. 16-3, the sensor device 60 is associated with an arm 95 that is positioned on the coronary sinus side of the tissue wall 21 and on a side of the shunt structure 90 that is proximally positioned with respect to the right atrium. That is, the sensor device 60 is secured to an anchor arm 95 that is positioned generally toward the right atrium (e.g., in the generally wider area of the coronary sinus 16). With the sensor transducer component 65 disposed in the channel area of the shunt conduit 98, the sensor transducer 65 may advantageously be disposed in an area of flow that is relatively high, thereby allowing for sensor readings to be generated indicating characteristics of the flow through the conduit 98 of the shunt structure 90. For example, the particular placement as shown in FIG. 16-3 with the sensor transducer 65 facing radially inward with respect to the axis of the conduit 98 may provide sensor readings that are more indicative of shunt flow characteristics compared to embodiments in which the sensor transducer is not disposed within the channel area of the conduit and/or is oriented/facing radially away from the conduit 98. In addition, with the sensor 60 disposed in the coronary sinus 16, the sensor 60 may be used to generate signals indicative of flow within the coronary sinus, including flow distal to the implant device 70 within the coronary sinus 16. Due to size constraints within the coronary sinus, it may be preferable for the sensor 60 to be associated with an arm 95 in the wider area of the coronary sinus (e.g., in area generally toward the ostium of the coronary sinus and the right atrium), as shown in FIG. 16-3.

With respect to the particular implementation of FIG. 16-4, the sensor device 60 is associated with an arm 92 that is positioned on the coronary sinus side of the tissue wall 21 and on a side of the shunt structure 90 that is distally positioned with respect to the right atrium. That is, the sensor device 60 is secured to an anchor arm 92 that is positioned generally away from the right atrium (e.g., in the generally narrower area of the coronary sinus 16). With the sensor transducer component 65 disposed in the channel area of the shunt conduit 98, the sensor transducer 65 may advantageously be disposed in an area of flow that is relatively high, thereby allowing for sensor readings to be generated indicating characteristics of the flow through the conduit 98 of the shunt structure 90. For example, the particular placement as shown in FIG. 16-4 with the sensor transducer 65 facing radially inward with respect to the axis of the conduit 98 may provide sensor readings that are more indicative of shunt flow characteristics compared to embodiments in which the sensor transducer is not disposed within the channel area of the conduit and/or is oriented/facing radially away from the conduit 98. In addition, with the sensor 60 disposed in the coronary sinus 16, the sensor 60 may be used to generate signals indicative of flow within the coronary sinus, including flow distal to the implant device 70 within the coronary sinus 16. Due to size constraints within the coronary sinus, however, it may be undesirable for the sensor 60 to be associated with an arm 92 in the narrower area of the coronary sinus (e.g., in area generally away from the ostium of the coronary sinus and the right atrium), as shown in FIG. 16-4. Therefore, in such implementations, may be desirable for the sensor device 60 to be a relatively small device and/or to be oriented relatively close to parallel with the tissue wall 21 and/or the axis of the coronary sinus 16 to reduce or avoid contact with the coronary sinus walls and/or cause blockage or other issues.

Figure 17:
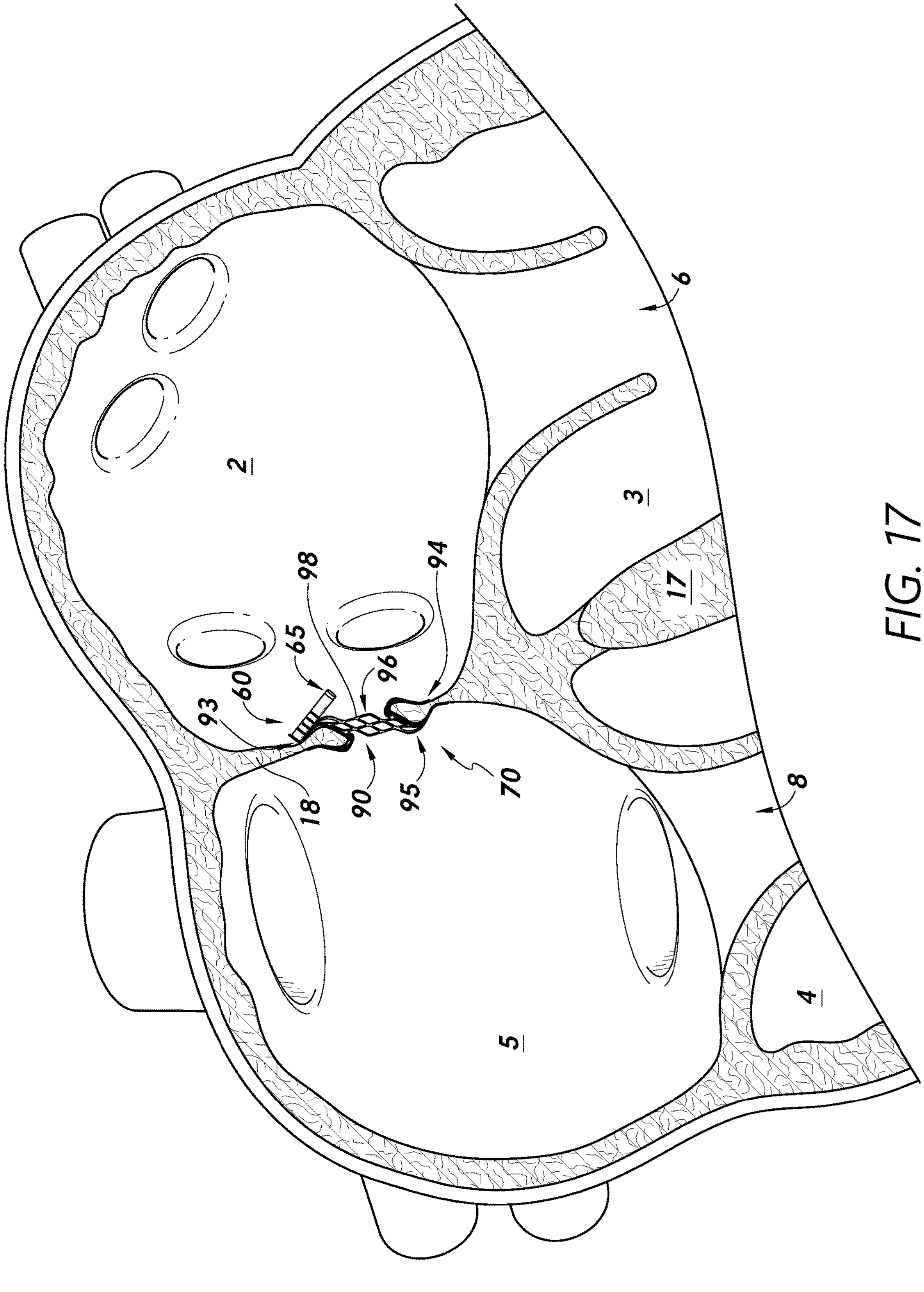
FIG. 17 shows a sensor implant device implanted in an atrial septum with a sensor of the device exposed in a left atrium in accordance with one or more embodiments.

FIG. 17 shows a sensor implant device 70 implanted in an atrial septum 18 with a sensor 60 of the device exposed in a left atrium 2 in accordance with one or more embodiments. As with other embodiments, the sensor implant device 70 shown in FIG. 17 includes a sensor device 60 including a sensor transducer component 65 and a cylindrical housing. The sensor device is disposed, attached, and/or otherwise secured or to or associated with the implant structure 90 (e.g., shunt structure) of the implant device 70 in a manner such that the sensor transducer 65 is disposed in a channel area associated with the barrel/conduit portion 98 of the shunt structure 90, the relevant channel area being within the left atrium.

Figure 18:
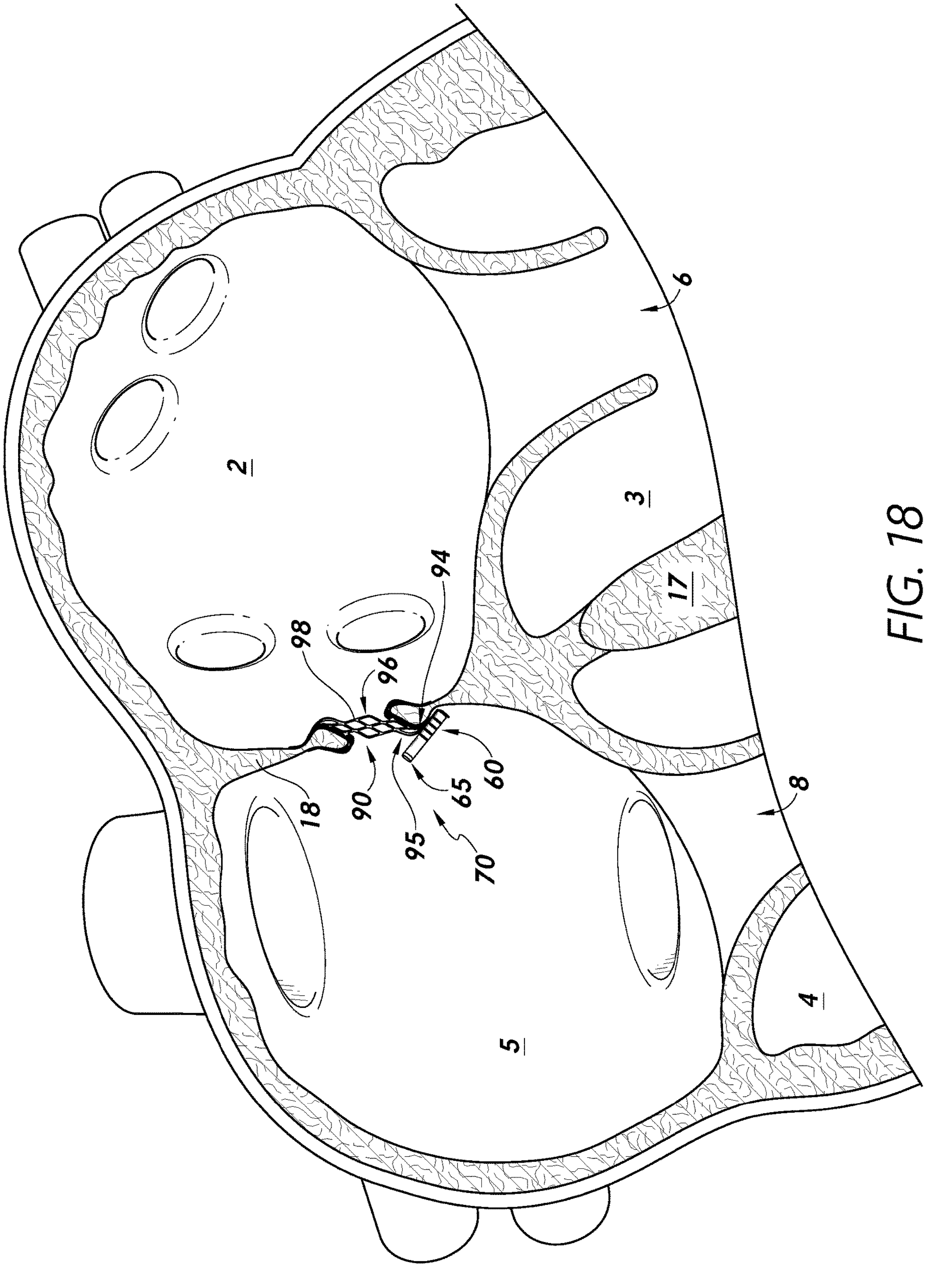
FIG. 18 shows a sensor implant device implanted in an atrial septum with a sensor of the device exposed in a right atrium in accordance with one or more embodiments.

FIG. 18 shows a sensor implant device 70 implanted in an atrial septum 18 with a sensor 60 of the device exposed in a right atrium 2 in accordance with one or more embodiments. As with other embodiments, the sensor implant device 70 shown in FIG. 18 includes a sensor device 60 including a sensor transducer component 65 and a cylindrical housing. The sensor device is disposed, attached, and/or otherwise secured or to or associated with the implant structure 90 (e.g., shunt structure) of the implant device 70 in a manner such that the sensor transducer 65 is disposed in a channel area associated with the barrel/conduit portion 98 of the shunt structure 90, the relevant channel area being within the right atrium.

Figure 19:
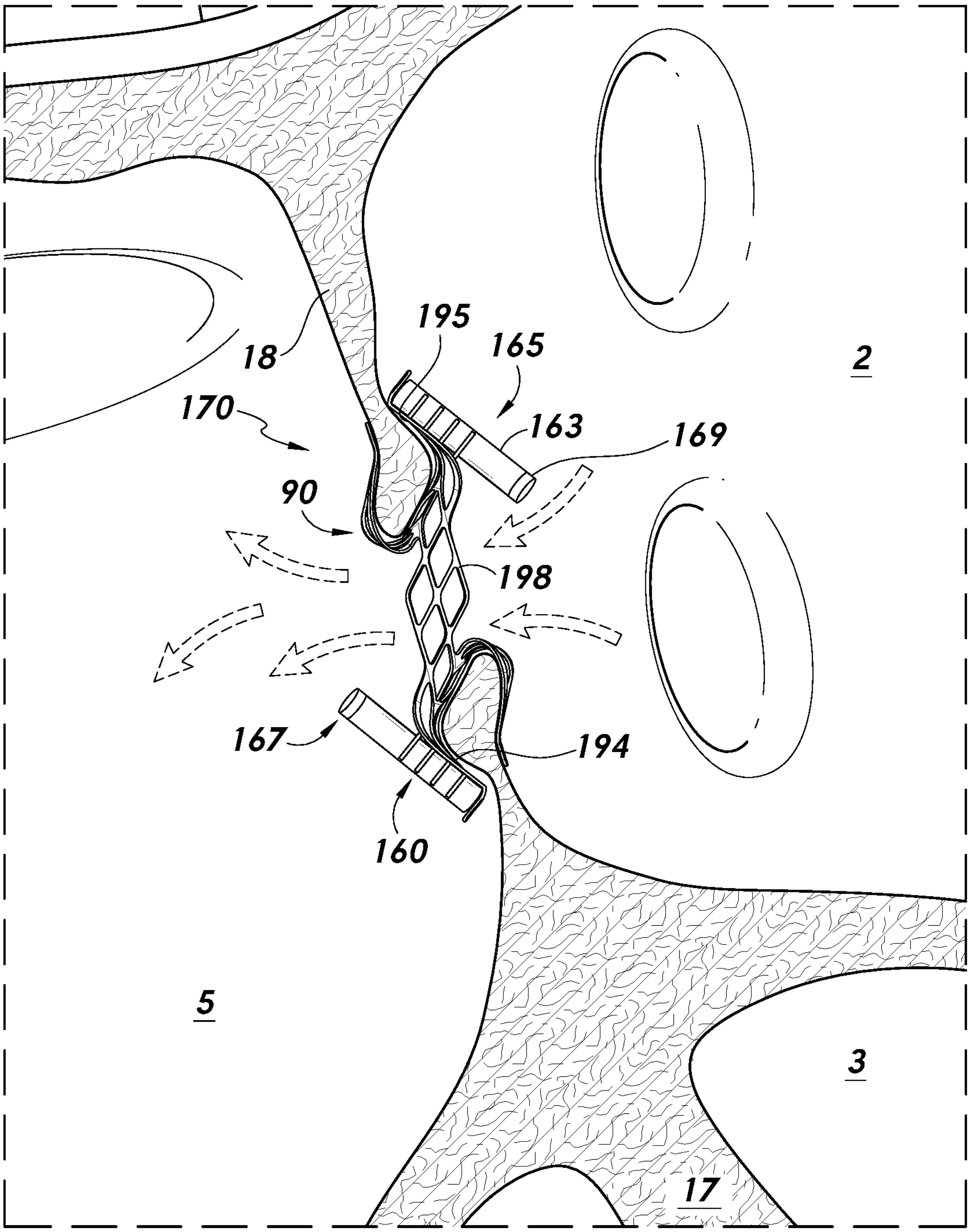
FIG. 19 shows a dual-sensor implant device implanted in an atrial septum in accordance with one or more embodiments.

FIG. 19 shows a dual-sensor implant device 170 implanted in an atrial septum 18 in accordance with one or more embodiments. Although certain embodiments are disclosed herein in the context of sensor implant devices including a single sensor device associated with a shunt structure, it should be understood that shunt sensor implant devices in accordance with aspects of the present disclosure may have any suitable or desirable number of sensor devices associated therewith. For example, the sensor implant device 170 shown in FIG. 19 includes two sensor devices 160, 165, wherein one of the sensor devices 160 is associated with a first sensor arm 194, whereas the other sensor device 165 is associated with a second sensor arm 195. The sensors 160, 165 are advantageously positioned, secured, and/or configured in a position/orientation such that respective sensor transducer components (167, 169) thereof are exposed in respective channel area(s) of the shunt structure 190 of the sensor implant device 170 on respective sides of the septum 18, as shown. Utilizing two or more sensors, with one or more sensors on each axial side/end of the relevant shunt structure, can provide improved shunt flow information in addition to atrial pressure information. Furthermore, where the sensor transducers face in opposite/opposing directions, as in the embodiment of FIG. 19, improved directional flow information may be derivable.

FIG. 19 shows the sensor implant device 170 implanted in an atrial septum wall 18, such that one sensor 160 and associated sensor transducer 167 are exposed in the right atrium 5, whereas another sensor 165 and associated sensor transducer 169 are exposed to the left atrium 2. In some embodiments of dual-sensor implant devices that may be similar in certain respects to the implant device 170, both the sensors may be exposed in the left atrium 2 or in the right atrium 5. With respect to multi-sensor shunt implant devices in accordance with aspects of the present disclosure, sensor transducers associated with at least one of the sensor devices may advantageously be disposed at least partially within a channel area associated with the relevant conduit/barrel structure. Furthermore, it should be understood that any description herein relating to the disposition/presence of a sensor transducer within a channel area associated with a shunt structure can be interpreted to mean that the sensor transducer is disposed wholly within the relevant channel area or partially within the channel area.

Although the illustration of FIG. 19 shows the two sensor devices 160, 165 being associated with retention arms emanating from opposite axial sides/ends of the fluid conduit/barrel structure 198, such that the sensor devices are exposed on opposite sides of the tissue wall 18, it should be understood that dual-sensor shunt implant devices in accordance with aspects of the present disclosure may have sensor devices associated with any anchor arm/feature. For example, as an alternative to the particular illustrated embodiment of FIG. 19, the sensor implant device 170 may include sensor devices associated with anchor arms associated with and/or emanating from a common axial side of the conduit/barrel structure 198, such that both sensors are exposed on a common side of a tissue wall in which the sensor implant device 170 is implanted.

Furthermore, although the illustrated embodiment of FIG. 19 shows the sensor devices 160, 165 associated with respective anchor arms 194, 195 that emanate from opposite circumferential sides/portions of the conduit/barrel structure 198, it should be understood that embodiments of the present disclosure may include multiple sensor devices associated with the same circumferential side/portion of the fluid conduit formed by the shunt structure.

Figure 20:
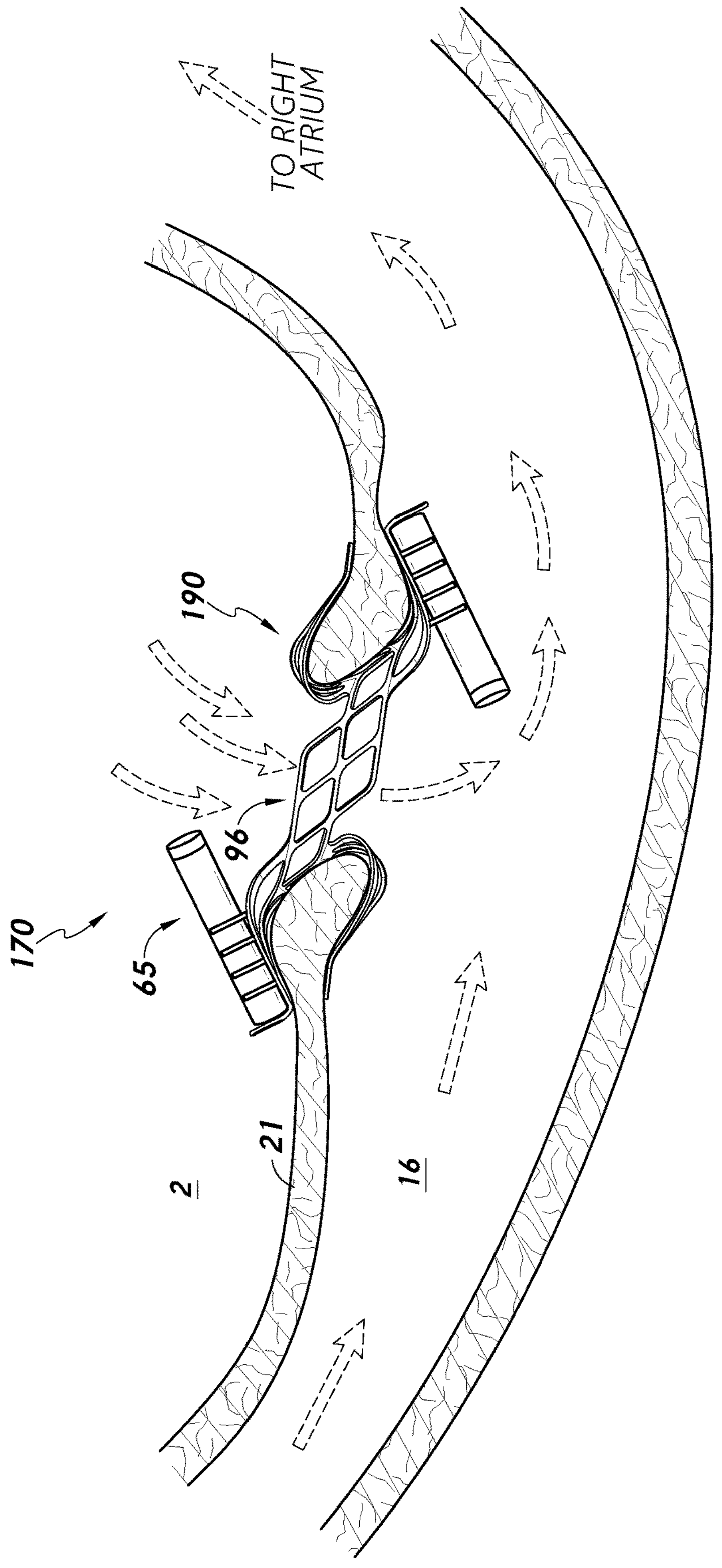
FIG. 20 shows a dual-sensor implant device implanted in a wall separating a coronary sinus from a left atrium in accordance with one or more embodiments.

FIG. 20 shows a dual-sensor implant device 170 implanted in a wall 21 separating a coronary sinus 16 from a left atrium 2 in accordance with one or more embodiments. As with the implementation of FIG. 19, the sensor implant device 170 may be implanted in the tissue wall 21 separating the coronary sinus 16 and the left atrium 2 in any configuration. For example, both the sensor devices 160, 165 and associated sensor transducers 167, 169 may be disposed on a coronary sinus side of the shunt structure 190 and tissue wall 21, the left atrium side of the shunt structure 190 and tissue wall 21, or may be on opposite axial sides as shown in FIG. 20. That is, the sensor devices 160, 165 and associated sensor transducers 167, 169 may be associated with the shunt structure 190 in any of the configurations described above in connection with FIGS. 16-1 through 16-4 and/or otherwise contemplated herein.

Figure 21:
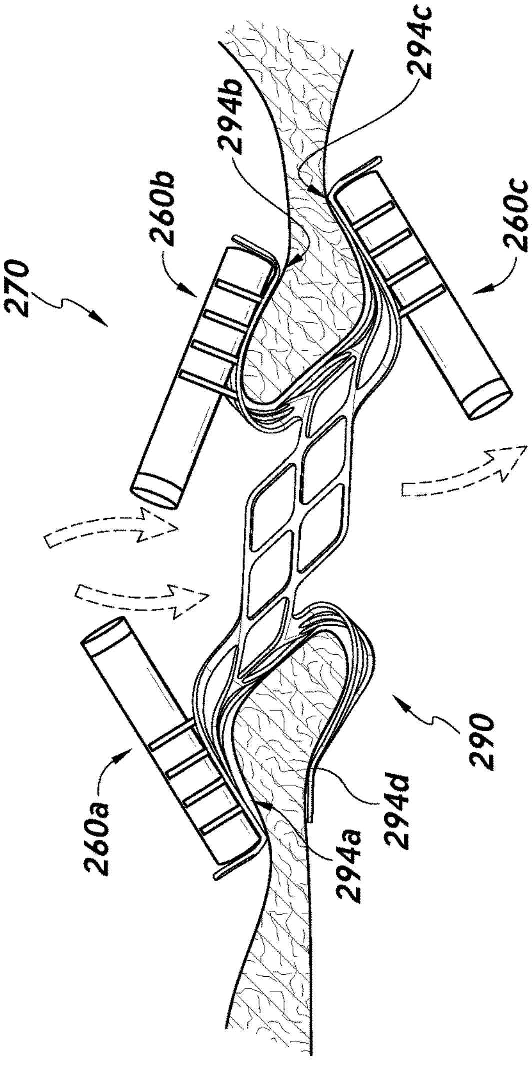
FIG. 21 shows a sensor implant device having three sensor devices associated therewith in accordance with one or more embodiments.

FIG. 21 shows a sensor implant device 270 having three sensor devices associated therewith in accordance with one or more embodiments of the present disclosure. The respective sensor devices 260*a*. 260*b*, 260*c* are associated with respective anchor arms 294*a*, 294*b*, 294*c*. Generally, in three-sensor embodiments, two of the sensor devices 260*a*, 260*b* may be associated with a first axial side/end of the shunt structure 290 of the implant device 170, whereas the third sensor 260*c* may be associated with an arm 294*c* associated with an opposite side/end of the shunt structure 290. For example, with respect to implementations in which the device 270 is implanted in an atrial septum wall, two sensor devices may be disposed on the left atrium side of the septal wall, whereas the third sensor device may be disposed on the right atrium side, or vice versa. Similarly, two sensors may be disposed on either the coronary sinus side or left atrium side of the wall separating the coronary sinus from the left atrium in implementations in which the device 270 is implanted in such wall. Although each of the respective sensor transducers is shown as being disposed in a channel area associated with the shunt structure 290, it should be understood that any of the sensor devices may be oriented in an orientation/configuration outside of a channel area. For example, with respect to multiple-sensor embodiments of the present disclosure, one or more of the sensor devices may be oriented such that a sensor transducer associated therewith faces generally radially outward with respect to the axis of the relevant conduit/barrel structure of the shunt structure, whereas at least one other sensor transducer may be configured/disposed within a channel area of the shunt structure, as described herein.

Figure 22:
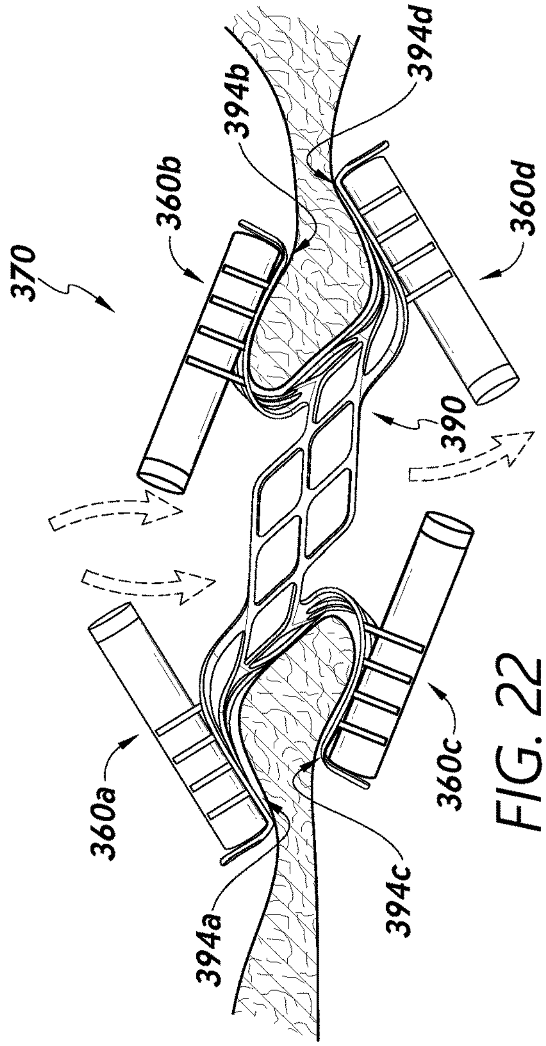
FIG. 22 shows a sensor implant device having four sensor devices associated therewith in accordance with one or more embodiments.
Figures 1, 23:
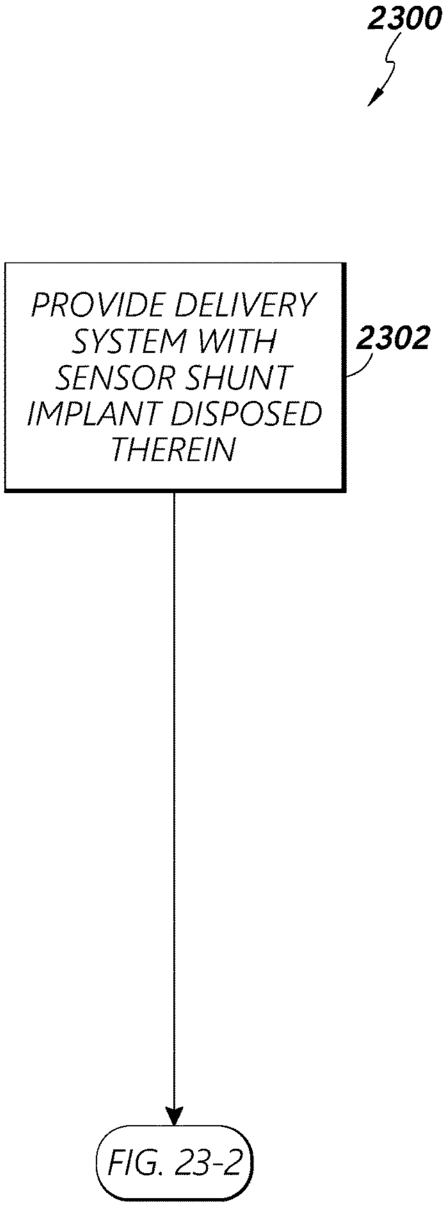

FIG. 22 shows a sensor implant device 370 having four sensor devices associated therewith in accordance with one or more embodiments. Specifically, the device 370 includes sensor devices 360*a*, 360*b*, 360*c*, and 360*d* associated with respective anchor arms 394*a*. 394*b*, 384*c*, and 394*d*. The sensor implant device 370 may be implanted in an atrial septum wall, a wall separating a coronary sinus from a left atrium, or any other tissue wall. Although the sensor implant device 370 is shown as having four sensor devices associated therewith, it should be understood that sensor implant devices in accordance with aspects of the present disclosure may have more than four sensor devices associated therewith, wherein each of the sensor transducers of the respective sensor devices may be disposed within a channel area and/or without a channel area. That is, the sensor devices may be in any suitable or desirable configuration or orientation with respect to the relevant shunt structure.

Left-to-right shunting in connection with physiological parameter (e.g., pressure) sensing functionality, as achieved in accordance with any of the devices and/or implantations associated with FIGS. 9-22, may advantageously be well-suited for patients that are relatively highly sensitive to atrial pressure increases. For example, as pressure increases in the ventricles and/or atria and is applied against the myocardial cells, the muscles of the heart may generally be prone to contract relatively harder according to process the excess blood. Therefore, as the ventricle dilates or stretches, for patients with compromised contractility of the ventricle, such patients may become more sensitive to higher pressures in the ventricle and/or atria because the heart may be unable to adequately respond or react thereto. Furthermore, increases in left-side (e.g., left atrial) pressure can results in dyspnea, and therefore reduction in left-side pressure to reduce dyspnea and/or reduce incidences of hospital readmission may be desirable through left-to-right shunting. For example, when the ventricle experiences dysfunction such that is unable to accommodate build-up in fluid pressure, such fluid may backup into the atria, thereby increasing atrial pressure. With respect to heart failure, minimization of left ventricular end-diastolic pressure may be paramount. Because left ventricular end-diastolic pressure can be related to left atrial pressure, backup of fluid in the atrium can cause backup of fluid in the lungs, thereby causing undesirable and/or dangerous fluid buildup in the lungs. Left-to-right shunting, such as using shunt devices in accordance with embodiments of the present disclosure, can divert extra fluid in the left side of the heart to the right side of the heart, which may be able to accommodate the additional fluid due to the relatively high compliance in the right atrium.

In some situations, left-to-right shunting may not be sufficiently effective due to the patient being subject to a drug regimen designed to control the patient's fluid output and/or pressure. For example, diuretic medications may be used to cause the patient to expel excess fluid. Therefore, use of pressure-sensor-integrated implants in accordance with embodiments of the present disclosure may provide a mechanism to inform technicians or doctors/surgeons with respect to how to titrate such medications to adjust/modify fluid status. Therefore, embodiments of the present disclosure may advantageously serve to direct medication intervention to reduce or prevent the undesirable increase in left atrial pressure.

FIGS. 23-1, 23-2, 23-3, 23-4, and 23-5 provide a flow diagram illustrating a process 2300 for implanting a sensor implant device in accordance with one or more embodiments. FIGS. 24-1, 24-2, 24-3, 24-4, and 24-5 provide images of cardiac anatomy and certain devices/systems corresponding to operations of the process 2300 of FIGS. 23-1, 23-2, 23-3, 23-4, and 23-5 in accordance with one or more embodiments.

Figures 1, 24:
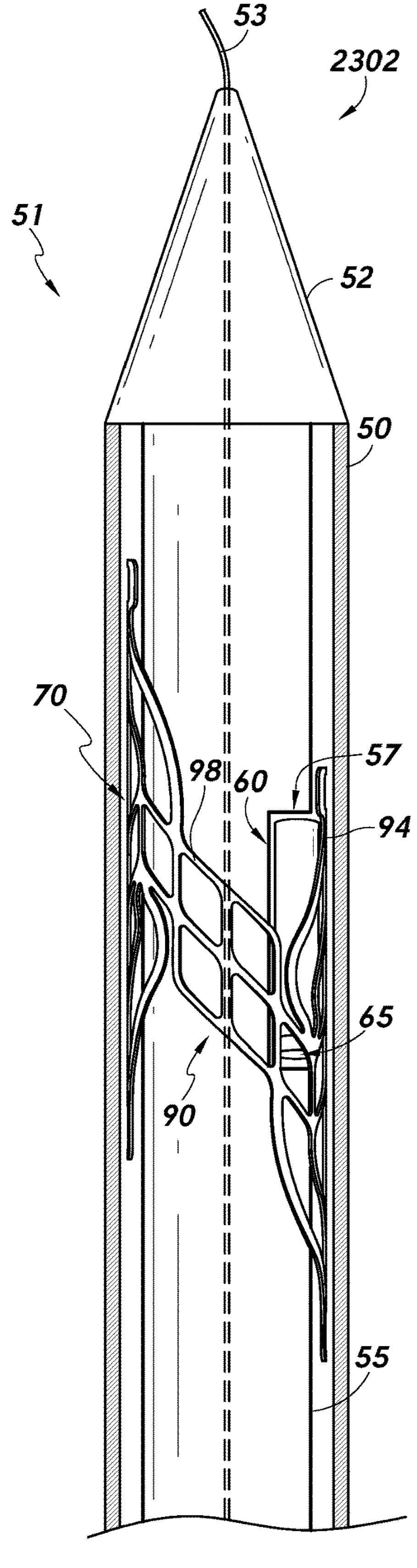
Figures 2, 23:
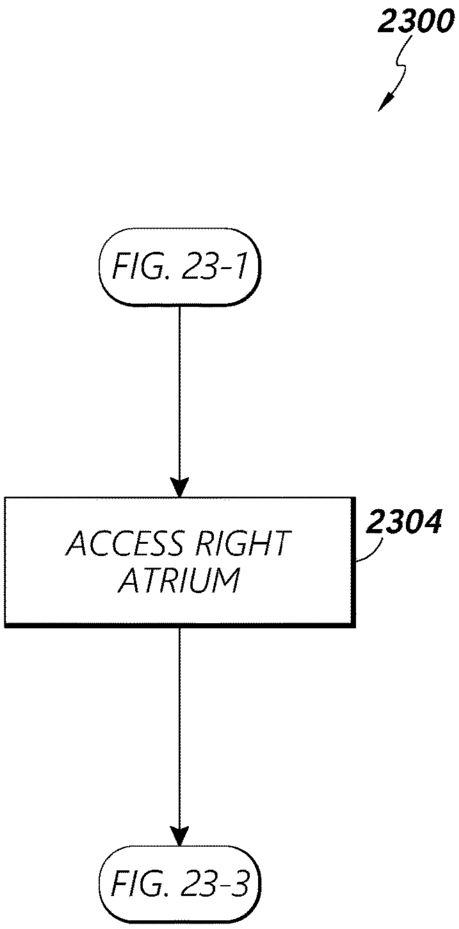
Figures 2, 24:
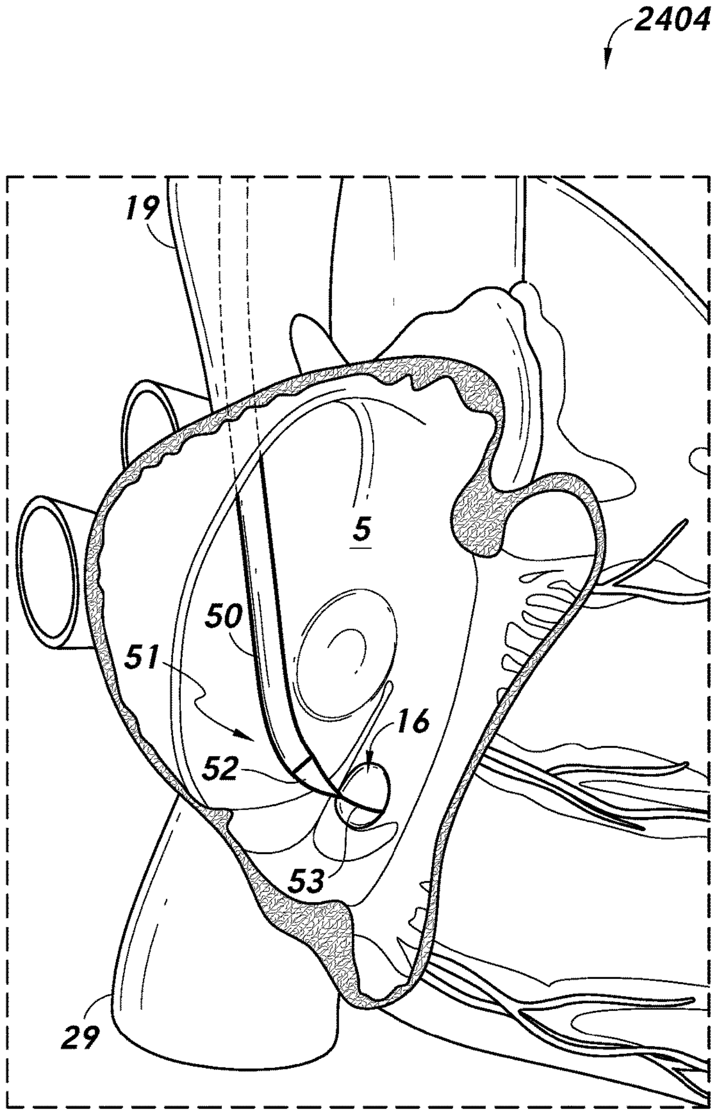
Figures 3, 23:
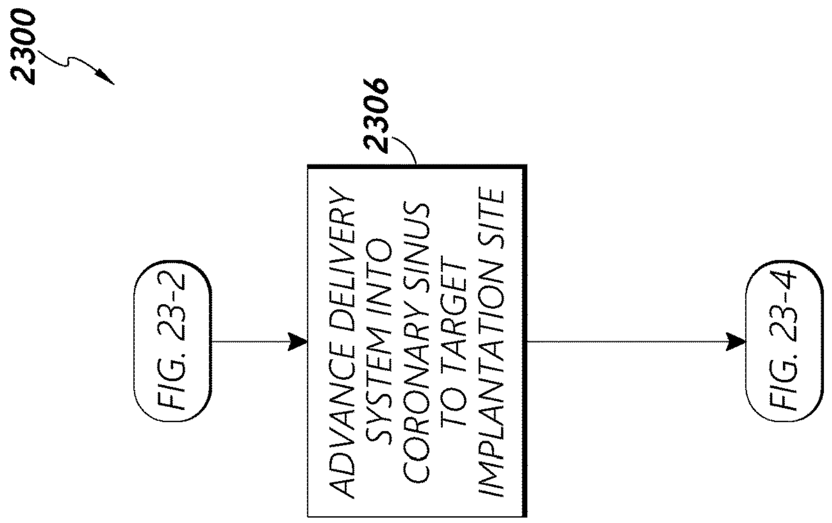
Figures 3, 24:
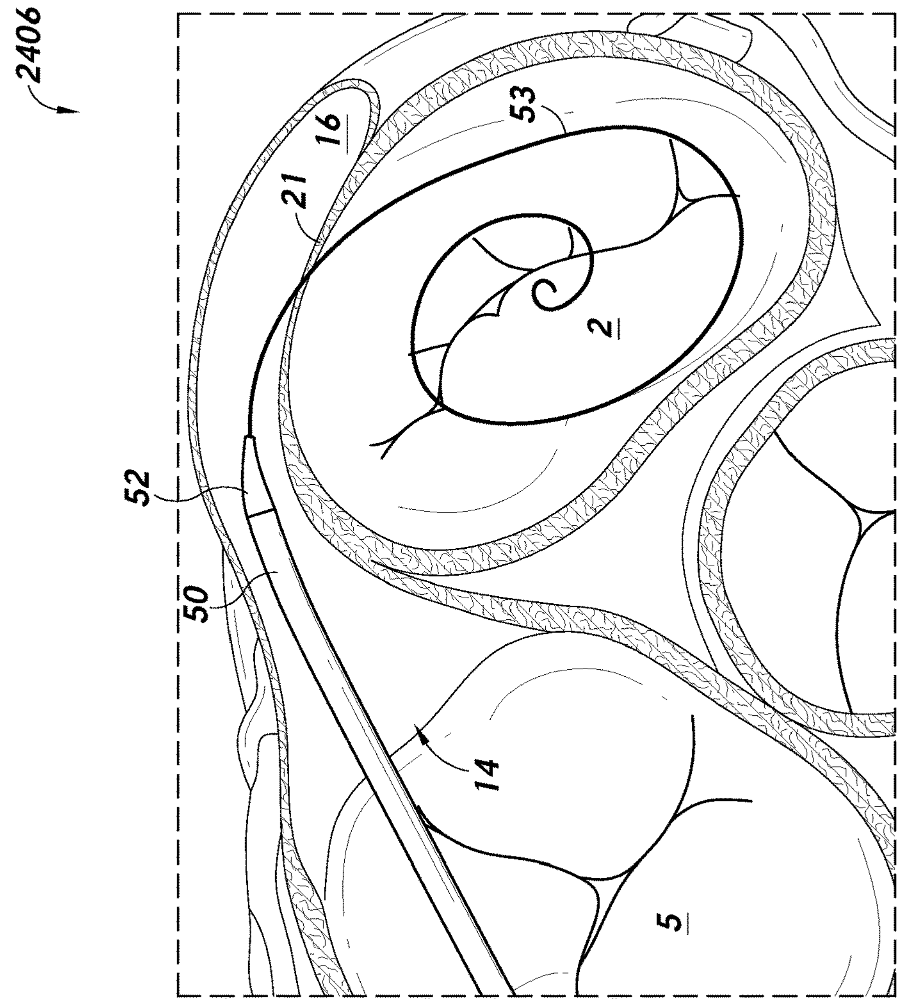
Figures 4, 24:
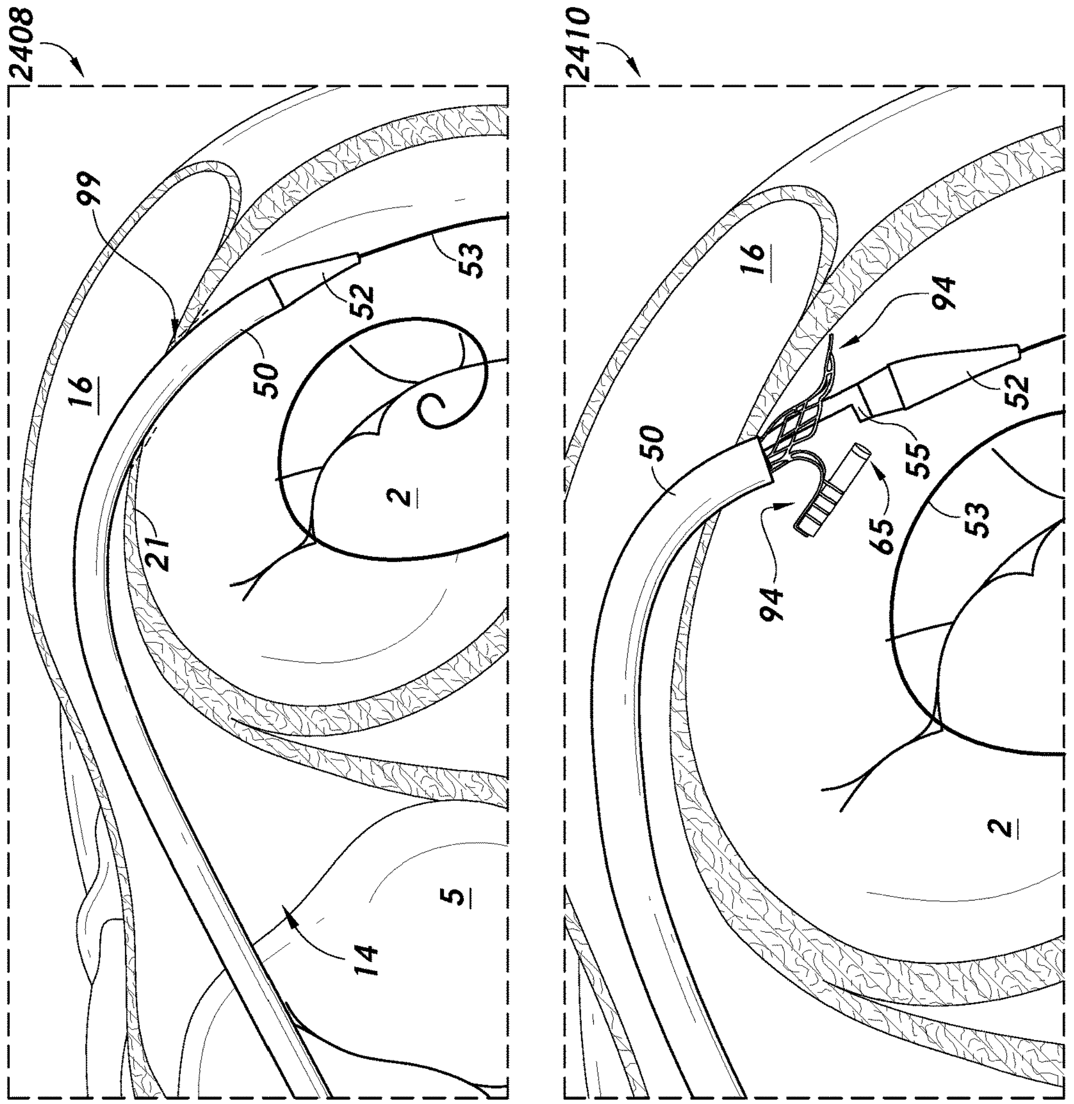
Figures 4, 23:
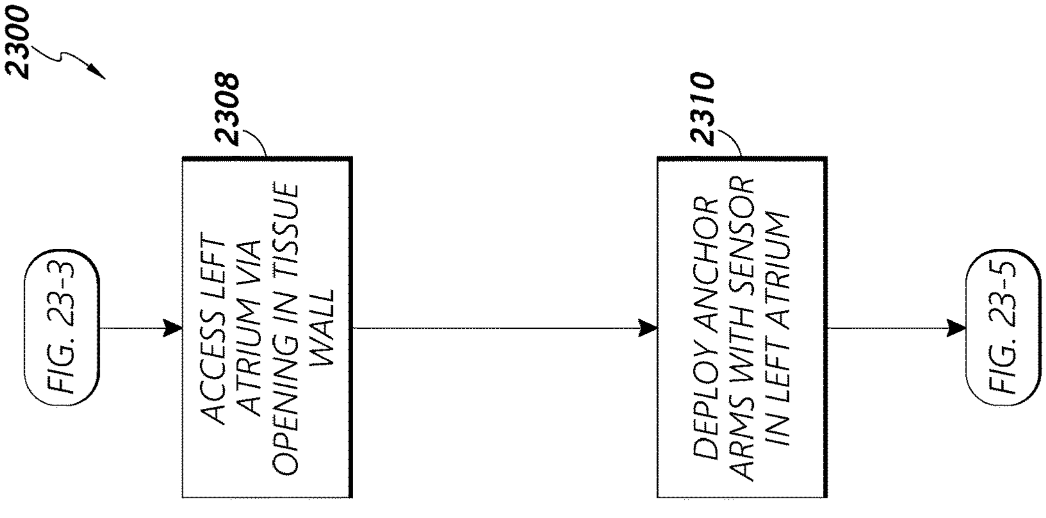
Figures 5, 24:
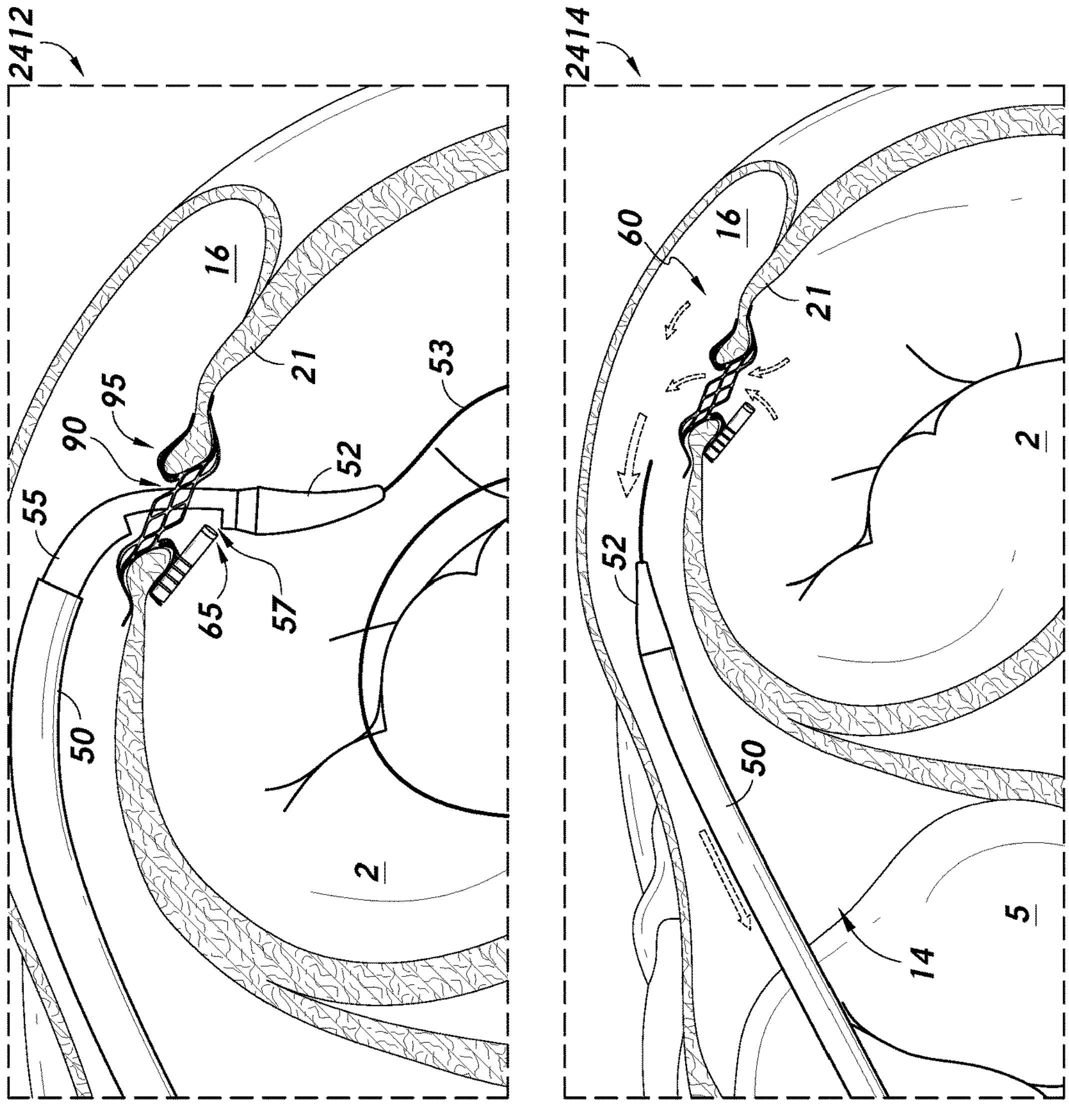
Figures 5, 23:
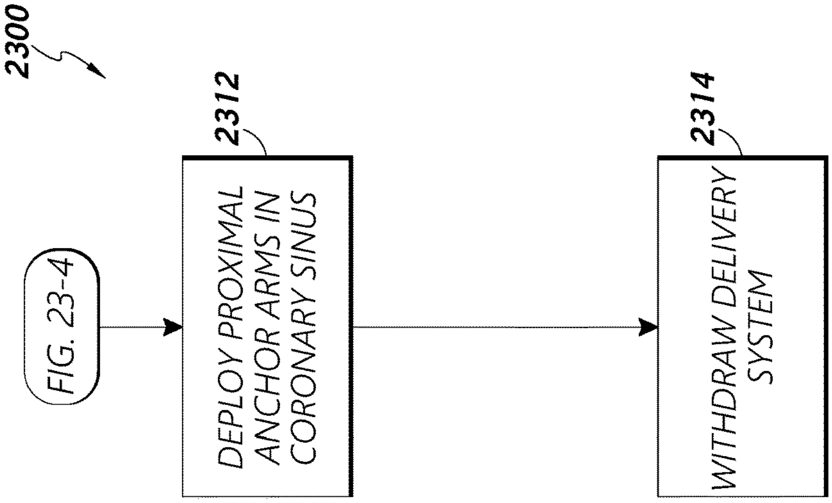

At block 2302, the process 2300 involves providing a delivery system 51 with a sensor implant device 70 disposed therein in a delivery configuration, such as a shunt-type sensor implant device as disclosed in detail herein. Image 2402 of FIG. 24-1 shows a partial cross-sectional view of a delivery system 51 for a sensor implant device 70 in accordance with one or more embodiments of the present disclosure. The image 2402 shows the sensor implant device 70 disposed within an outer sheath 50 of the delivery system 51. Although a particular embodiment of a delivery system is shown in FIG. 24-1, it should be understood that sensor implant devices in accordance with aspects of the present disclosure may be delivered and/or implanted using any suitable or desirable delivery system and/or delivery system components.

The illustrated delivery system 51 includes an inner catheter 55, which may be disposed at least partially within the outer sheath 50 during one or more portions of the process 2300. In some embodiments, the shunt structure 90 of the sensor implant device 70 may be disposed at least partially around the inner catheter 55, wherein the shunt structure 90 is disposed at least partially within the outer sheath 50 during one or more portions of the process 2300. For example, the inner catheter 55 may be disposed within the barrel portion 98 of the shunt structure 90, as shown.

In some embodiments, the delivery system 51 may be configured such that a guidewire 53 may be disposed at least partially therein. For example, the guidewire 53 may run in the area of an axis of the sheath 50 and/or inner catheter 55, such as within the inner catheter 55, as shown. The delivery system 51 may be configured to be advanced over the guidewire 53 to guide the delivery system 51 to a target implantation site.

In some embodiments, the delivery system 51 includes a tapered nosecone feature 52, which may be associated with a distal end of the sheath 50, catheter 55, and/or delivery system 51. In some implementations, the nosecone feature 52 may be utilized to dilate the opening in a tissue wall into which the sensor implant device 70 is to be implanted, or through which the delivery system is to be advanced. The nosecone feature 52 may facilitate advancement of the distal end of the delivery system 51 through the tortuous anatomy of the patient and/or with an outer delivery sheath or other conduit/path. The nosecone 52 may be a separate component from the catheter 55 or may be integrated with the catheter 55. In some embodiments, the nosecone 52 is adjacent to and/or integrated with a distal end of the catheter 55. In some embodiments, the nosecone 52 may comprise and/or be formed of multiple flap-type forms that can be urged/spread apart when the sensor implant device 70 and/or any portions thereof, the interior catheter 55, or other device(s) are advanced therethrough.

In some embodiments, the sensor implant device 70 may be disposed in the delivery system 51 with a sensor device 60, as described in detail herein, attached thereto or otherwise associated therewith. In some embodiments, the inner catheter 55 includes one or more cut-outs, indentations, recesses, gaps, openings, apertures, holes, slits, or other features configured to accommodate the presence of the sensor device 60 and/or other feature(s) or aspect(s) of the implant device 70. For example, the sensor device 60 may be disposed at least partially within an inner diameter of the shunt structure 90 in the delivery configuration shown in FIG. 24-1. In such configurations, the sensor assembly component(s) may create an interference with respect to the ability of the shunt structure 90 to be disposed relatively tightly around the inner catheter 55, thereby potentially increasing the profile of the delivery system and/or affecting the ability of the sensor implant device 70 to be delivered using the delivery system 51. Therefore, as shown in FIG. 24-1, the inner catheter 55 may include one or more sensor device accommodation features, such as a sensor cut-out or other accommodation feature 57. In some embodiments, the accommodation feature 57 may be longitudinal and circumferential cut-outs of the inner catheter 55. The accommodation feature 57 may advantageously be dimensioned to correspond to the size and/or profile of the sensor device, as shown, and may allow for the sensor device to radially project into an inner diameter/space of the inner catheter 55.

The sensor implant device 70 can be positioned within the delivery system 51 with a first end thereof (i.e., distal anchor arm(s) 94) disposed distally with respect to the barrel 98 of the shunt structure 90. A second end (i.e., proximal anchor arm(s)) is positioned at least partially proximally with respect to the barrel 98 of the shunt structure 90 and/or the sensor device 60.

The outer sheath 50 may be used to transport the sensor implant device 70 to the target implantation site. That is, the sensor implant device 70 may be advanced to the target implantation site at least partially within a lumen of the outer sheath 50, such that the sensor implant device 70 is held and/or secured at least partially within a distal portion of the outer sheath 50.

At block 2304, the process 2300 involves accessing a right atrium 5 of a heart of a patient using the delivery system 51 with the sensor implant device 70 disposed therein. In some implementations, accessing the cardiac anatomy with the delivery system 51 may be performed following one or more procedures or steps to place the guidewire 53 and/or form and/or dilate an opening between the left atrium 2 and coronary sinus 16 of the patient's heart, the details of which are omitted for convenience and clarity.

At block 2306, the process 2300 involves advancing the delivery system 51 into the coronary sinus 16 to a target implantation site adjacent a wall 21 separating the coronary sinus 16 from the left atrium 2. Access to the target wall 21 and left atrium 2 via the coronary sinus 16 may be achieved using any suitable or desirable procedure. For example, various access pathways may be utilized in maneuvering guidewires and catheters in and around the heart to deploy an expandable shunt integrated or associated with a pressure sensor in accordance with embodiments of the present disclosure. In some embodiments, access may be achieved through the subclavian or jugular vein into the superior vena cava (not shown), right atrium 5, and from there into the coronary sinus 16. Alternatively, the access path may start in the femoral vein and through the inferior vena cava (not shown) into the heart. Other access routes may also be used, each of which may typically utilize a percutaneous incision through which the guidewire and catheter are inserted into the vasculature, normally through a sealed introducer, and from there the system may be designed or configured to allow the physician to control the distal ends of the devices from outside the body.

In some implementations, the guidewire 53 is introduced through the subclavian or jugular vein, through the superior vena cava 19, and into the coronary sinus 16 via the right atrium 5. The guidewire 53 can be disposed in a spiral configuration within the left atrium 2, as shown in the image 24-6, which may help to secure the guidewire in place. Once the guidewire 53 provides a path, an introducer sheath may be routed along the guidewire 53 and into the patient's vasculature, such as with the use of a dilator. The delivery catheter may be advanced through the superior vena cava to the coronary sinus 16 of the heart, wherein the introducer sheath may provide a hemostatic valve to prevent blood loss. In some embodiments, a deployment catheter may function to form and prepare an opening in the wall 21 of the left atrium, and a separate placement delivery system 51, as shown, is used for delivery of the sensor implant device 70. In other embodiments, the deployment system 51 may be used as the both the puncture preparation and implant delivery catheter with full functionality. In the present application, the term "delivery system" is used to represent a catheter or introducer with one or both of these functions.

At block 2308, the process 2300 involves accessing the left atrium through an opening 99 formed in the wall 21. For example, the guidewire 53 may be disposed as running through the opening 99 prior to penetration thereof by the nosecone 52. The opening 99 may originally be formed using a needle (not shown) associated with the delivery system 51 or other delivery system implemented prior to block 2308. In some implementations, the nosecone feature 52 may be used to at least partially dilate the opening 99, which may have been previously dilated using a balloon dilator or other instrument.

At block 2310, the process 2300 involves deploying one or more anchor arms 94, which may be considered the distal anchor arm(s) of the sensor implant device 70, on the atrial side of the wall 21. The distal arm(s) 94 can have associated therewith a sensor device 60, such that a sensor transducer 65 of the sensor device 60 is exposed within the left atrium 2, such that the sensor transducer 60 can be used to obtain signals indicating physiological parameters associated with the left atrium, such as pressure.

At block 2312, the process 2300 involves deploying one or more proximal arms 95 of the sensor implant device 70 on a coronary sinus side of the tissue wall 21 to thereby sandwich portions of the wall 21 between the distal and proximal arms of the shunt structure 90. At block 2314, the process 2300 involves withdrawing the delivery system 51, leaving the sensor implant device 70 implanted in the tissue wall 21, thereby allowing blood flow to be shunted through the implant device 70 from the left atrium 2 into the right side of the heart via the coronary sinus 16.

Additional aspects and features of processes for delivering shunt structures that may be integrated with sensor devices/functionality in accordance with embodiments of the present disclosure for implantation in the wall between the coronary sinus and the left atrium are disclosed in U.S. Pat. No. 9,789,294, entitled "Expandable Cardiac Shunt," issued on Oct. 24, 2017, the disclosure of which is hereby expressly incorporated by reference in its entirety. Although the implant device 70 is shown in the left atrium/coronary sinus wall 21, the implant device 70 may be positioned between other cardiac chambers, such as between the left and right atria.

Figure 25:
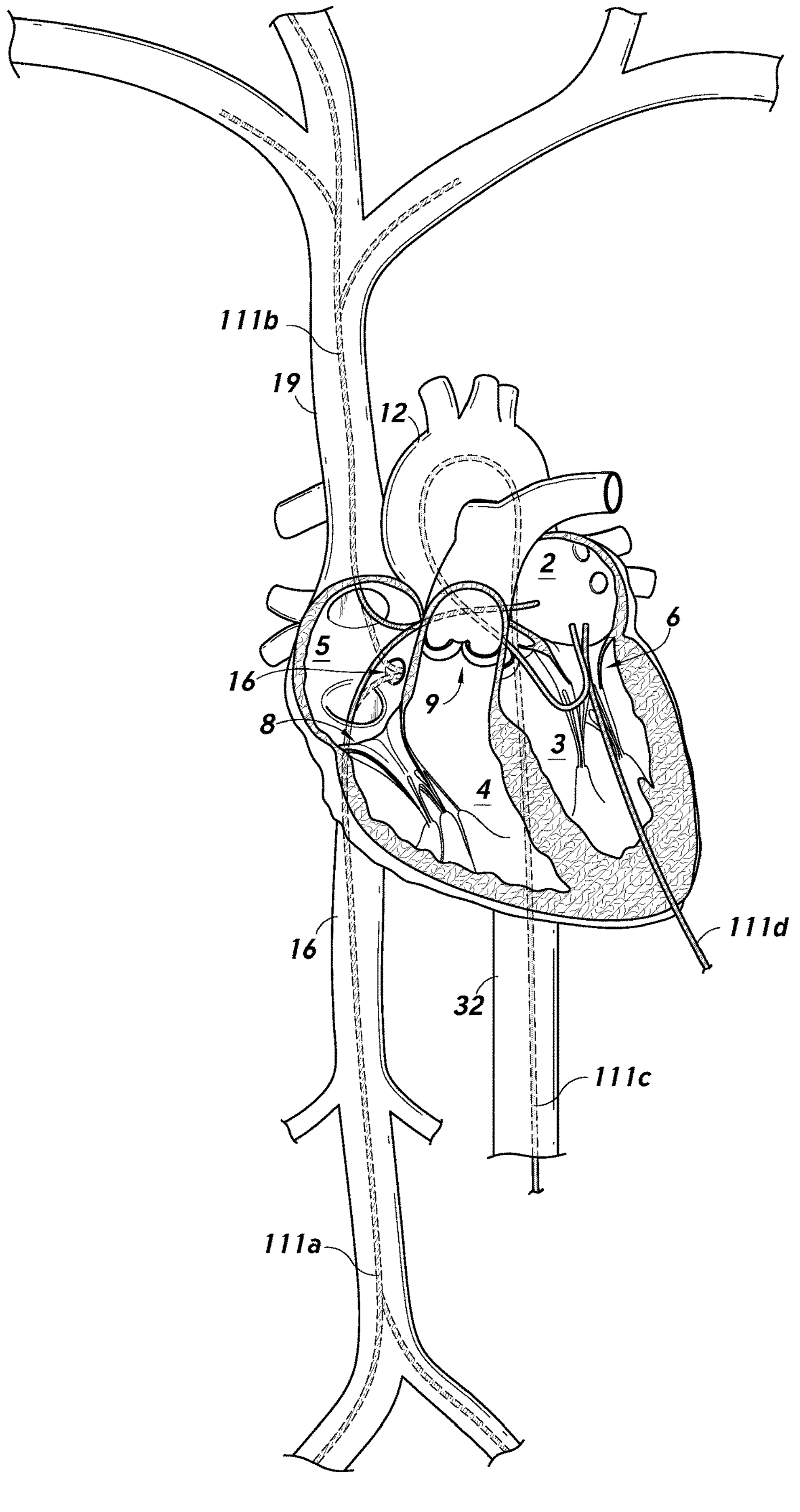
FIG. 25 is a cutaway view of a human heart and associated vasculature showing certain catheter access paths for pulmonary vein shunting procedures in accordance with one or more embodiments.

FIG. 25 is a cutaway view of a human heart and associated vasculature showing certain catheter access paths for implanting sensor implant devices in accordance with one or more embodiments. FIG. 25 shows various catheters 111 that may be used to implant sensor devices in accordance with aspects of the present disclosure. The catheters 111 can advantageously be steerable and relatively small in cross-sectional profile to allow for traversal of the various blood vessels and chambers through which they may be advanced en route to, for example, the right atrium 5, coronary sinus 16, left atrium 2 or other anatomy or chamber. Catheter access to the right atrium 5, coronary sinus 16, or left atrium 2 in accordance with certain transcatheter solutions may be made via the inferior vena cava 16 (as shown by the catheter 11*a*) or the superior vena cava 19 (as shown by the catheter 111*b*). Further access to the left atrium may involve crossing the atrial septum (e.g., in the area at or near the fossa ovalis).

Although access to the left atrium is illustrated and described in connection with certain examples as being via the right atrium and/or vena cavae, such as through a transfemoral or other transcatheter procedure, other access paths/methods may be implemented in accordance with examples of the present disclosure. For example, in cases in which septal crossing through the interatrial septal wall is not possible, other access routes may be taken to the left atrium 2. In patients suffering from a weakened and/or damaged atrial septum, further engagement with the septal wall can be undesirable and result in further damage to the patient. Furthermore, in some patients, the septal wall may be occupied with one or more implant devices or other treatments, wherein it is not tenable to traverse the septal wall in view of such treatment(s). As alternatives to transseptal access, transaortic access may be implemented, wherein a delivery catheter 111*c* is passed through the descending aorta 32, aortic arch 12, ascending aorta, and aortic valve 7, and into the left atrium 2 through the mitral valve 6. Alternatively, transapical access may be implemented to access the target anatomy, as shown by delivery catheter 111*d*.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A sensor implant device comprising:

a tubular frame having first and second diametrical sides and first and second axial ends;

a first anchor arm associated with the first side and the first end of the tubular frame;

a second anchor arm associated with the second side and the first end of the tubular frame;

a third anchor arm associated with the first side and the second end of the tubular frame;

a fourth anchor arm associated the second side and the second end of the tubular frame, each of the first, second, third, and fourth anchor arms having a base segment coupled to the tubular frame and a distal segment extending from the base segment, the distal segment having a tissue-contact end; and a first sensor device coupled to the first anchor arm, the first sensor device including a first end portion and a second end portion opposite the first end portion, wherein a sensor element is associated with the second end portion;

wherein the sensor element of the first sensor device is positioned by the first anchor arm over a flow channel of the tubular frame beyond the first end of the tubular frame and the first end portion of the first sensor device is associated with the tissue-contact end of the first anchor arm.

2. The sensor implant device of claim 1, wherein:

the sensor implant device is configured to assume a deployed configuration in which the first, second, third, and fourth anchor arms project radially away from the tubular frame;

the base segment of the first anchor arm projects axially and radially outward from the first side and the first end of the tubular frame;

the tissue-contact end of the first anchor arm deflects back toward an axial center of the tubular frame; and the first sensor device is mechanically coupled to the distal segment of the first anchor arm by a plurality of sensor-retention fingers.

3. The sensor implant device of claim 2, further comprising a second sensor device coupled to the fourth anchor arm, wherein the fourth anchor arm holds a sensor end of the second sensor device over the flow channel of the tubular frame beyond the second end of the tubular frame.

4. The sensor implant device of claim 1, wherein the first anchor arm includes a distal stopper tab that prevents the first sensor device from moving beyond a distal end of the first anchor arm.

5. The sensor implant device of claim 1, wherein the first anchor arm includes a sensor-retention cup that is open in a direction towards an axis of the tubular frame, the first end portion of the first sensor device being contained within the sensor-retention cup.

6. The sensor implant device of claim 1, wherein the sensor implant device is configured to assume a delivery configuration in which:

the first, second, third, and fourth anchor arms project axially away from the tubular frame; and the sensor element of the first sensor device is disposed within the tubular frame between the first and second axial ends of the tubular frame.

7. The sensor implant device of claim 6, wherein the first anchor arm comprises a plurality of struts, including a pair of outer side struts, the outer side struts extending toward the tissue-contact end of the first anchor arm and converging toward one another at the tissue-contact end of the first anchor arm.

* * * * *